(12) United States Patent
Popielarski et al.

(10) Patent No.: US 12,370,079 B2
(45) Date of Patent: Jul. 29, 2025

(54) APPARATUS AND METHOD FOR THERMAL BLOCKADE OF NERVES

(71) Applicants: Thermaquil, Inc., Philadelphia, PA (US); University of Pittsburgh—Of the Commonwealth System of Higher Education, Pittsburgh, PA (US)

(72) Inventors: Stephen R. Popielarski, Devon, PA (US); Changfeng Tai, Wexford, PA (US); Grant M. Chapman, Indianapolis, IN (US)

(73) Assignees: Thermaquil, Inc., Philadelphia, PA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 904 days.

(21) Appl. No.: 17/127,431

(22) Filed: Dec. 18, 2020

(65) Prior Publication Data
US 2021/0236328 A1    Aug. 5, 2021

Related U.S. Application Data

(63) Continuation of application No. PCT/US2020/065636, filed on Dec. 17, 2020, and a
(Continued)

(51) Int. Cl.
*A61F 7/00* (2006.01)
*A61N 1/40* (2006.01)
(Continued)

(52) U.S. Cl.
CPC ............ *A61F 7/007* (2013.01); *A61F 7/0085* (2013.01); *A61N 1/403* (2013.01); *A61N 5/025* (2013.01);
(Continued)

(58) Field of Classification Search
CPC .............. A61N 1/3605; A61N 1/36053; A61N 1/36057; A61N 1/3606; A61N 1/36062;
(Continued)

(56) References Cited

U.S. PATENT DOCUMENTS

| 4,585,002 A | 4/1986 | Kissin |
|---|---|---|
| 6,074,414 A | 6/2000 | Haas et al. |

(Continued)

FOREIGN PATENT DOCUMENTS

| CN | 106669027 A | 5/2017 |
|---|---|---|
| JP | 2010088914 A | 4/2010 |

(Continued)

OTHER PUBLICATIONS

Morgan et al. Thermal block of mammalian unmyelinated C fibers by local cooling to 15-25 after a brief heating at 45° C. J Neurophysiol. Jun. 1, 2020; 123(6): 2173-2179. Published online May 6, 2020. doi: 10.1152/jn.00133.2020: 10.1152/jn.00133.2020 (Year: 2020).*

(Continued)

*Primary Examiner* — Brian T Gedeon
(74) *Attorney, Agent, or Firm* — McNees Wallace & Nurick LLC

(57) ABSTRACT

Embodiments disclosed include systems, methods, and apparatuses, directed to administering thermal neural modulation to mammalian tissue to control nerve conduction. Embodiments disclosed include an apparatus comprising a thermal energy source, a first heat exchanger coupled to the thermal energy source and configured to receive thermal energy therefrom, a thermal applicator configured to be disposed and secured to the anatomy of a subject having a nerve therein, in contact with the skin on the anatomy and overlying a treatment portion of the nerve, the thermal applicator configured to transfer thermal energy to the skin to raise the temperature of the treatment portion of the nerve (Continued)

above a physiologic temperature, a second heat exchanger is coupled to the thermal applicator and configured to transfer thermal energy thereto, and a fluid conduit having a first portion coupled to the first heat exchanger and a second portion coupled to the second heat exchanger. The fluid conduit is configured to have fluid circulated therethrough to convey thermal energy from the thermal energy source via the first heat exchanger and to the thermal applicator via the second energy at a temperature.

13 Claims, 48 Drawing Sheets
(7 of 48 Drawing Sheet(s) Filed in Color)

Related U.S. Application Data continuation-in-part of application No. PCT/US2019/038065, filed on Jun. 19, 2019.

(60) Provisional application No. 62/949,969, filed on Dec. 18, 2019, provisional application No. 62/686,712, filed on Jun. 19, 2018.

(51) Int. Cl.
*A61N 5/02* (2006.01)
*A61N 5/06* (2006.01)

(52) U.S. Cl.
CPC ......... *A61N 5/0622* (2013.01); *A61N 5/0625* (2013.01); *A61F 2007/0007* (2013.01); *A61F 2007/0054* (2013.01); *A61F 2007/0056* (2013.01); *A61F 2007/0071* (2013.01); *A61F 2007/0075* (2013.01); *A61F 2007/0086* (2013.01); *A61F 2007/0096* (2013.01); *A61N 2005/0659* (2013.01)

(58) Field of Classification Search
CPC ............ A61N 1/36064; A61N 1/36067; A61N 1/36071; A61N 1/36075; A61N 1/36078; A61N 1/36087; A61N 1/36085; A61N 1/36089; A61N 1/36092; A61N 1/39096
See application file for complete search history.

(56) References Cited

U.S. PATENT DOCUMENTS

| | | |
|---|---|---|
| 6,375,674 B1 | 4/2002 | Carson |
| 7,789,202 B2 | 9/2010 | Lee et al. |
| 8,805,510 B2 | 8/2014 | Chancellor et al. |
| 8,876,815 B2 | 11/2014 | Coe et al. |
| 9,020,592 B2 | 4/2015 | Dacey, Jr. et al. |
| 9,878,154 B2 | 1/2018 | Tai |
| 10,322,293 B2 | 6/2019 | Chiel et al. |
| 11,051,975 B2 | 7/2021 | Tai |
| 11,826,572 B2 | 11/2023 | Tai |
| 11,865,346 B2 | 1/2024 | Tai |
| 2004/0127953 A1 | 7/2004 | Kilgore et al. |
| 2005/0039465 A1 | 2/2005 | Welch |
| 2006/0190053 A1 | 8/2006 | Dobak, III |
| 2007/0027486 A1 | 2/2007 | Armstrong |
| 2007/0135875 A1 | 6/2007 | Demarais et al. |
| 2007/0173908 A1 | 7/2007 | Begnaud |
| 2007/0225781 A1 | 9/2007 | Saadat et al. |
| 2008/0065158 A1 | 3/2008 | Ben-Ezra et al. |
| 2008/0228248 A1 | 9/2008 | Guyuron et al. |
| 2009/0036945 A1 | 2/2009 | Chancellor et al. |
| 2009/0149895 A1 | 6/2009 | Dacey, Jr. et al. |
| 2009/0149926 A1 | 6/2009 | Dacey, Jr. et al. |
| 2009/0187223 A1 | 7/2009 | Gross |
| 2009/0204173 A1 | 8/2009 | Fang et al. |
| 2010/0036454 A1 | 2/2010 | Bennett et al. |
| 2010/0222854 A1 | 9/2010 | Demarais et al. |
| 2010/0305632 A1 | 12/2010 | Maskara et al. |
| 2012/0310313 A1 | 12/2012 | Rogers et al. |
| 2013/0035740 A1 | 2/2013 | Sharma et al. |
| 2013/0158627 A1 | 6/2013 | Gozani et al. |
| 2013/0238049 A1 | 9/2013 | Simon et al. |
| 2013/0289369 A1* | 10/2013 | Margolis ............ A61B 18/1492 606/41 |
| 2013/0296977 A1 | 11/2013 | Chiu et al. |
| 2014/0228900 A1 | 8/2014 | Osorio |
| 2014/0276539 A1 | 9/2014 | Allison et al. |
| 2014/0277302 A1 | 9/2014 | Weber et al. |
| 2015/0032181 A1 | 1/2015 | Baynham et al. |
| 2015/0051637 A1 | 2/2015 | Osorio |
| 2015/0127077 A1 | 5/2015 | Ben Asher et al. |
| 2015/0265836 A1 | 9/2015 | Simon et al. |
| 2015/0366703 A1 | 12/2015 | Du |
| 2015/0374996 A1 | 12/2015 | Levin et al. |
| 2016/0022477 A1 | 1/2016 | Schaefer et al. |
| 2016/0066701 A1 | 3/2016 | Diller et al. |
| 2017/0095667 A1 | 4/2017 | Yakovlev et al. |
| 2017/0209333 A1 | 7/2017 | Shoup et al. |
| 2017/0280883 A1 | 10/2017 | Diller |
| 2017/0333708 A1 | 11/2017 | Conde et al. |
| 2017/0348540 A1 | 12/2017 | Doan et al. |
| 2017/0361091 A1 | 12/2017 | Tai |
| 2018/0042761 A1 | 2/2018 | Smith et al. |
| 2018/0085580 A1 | 3/2018 | Perez et al. |
| 2018/0207450 A1 | 7/2018 | Sanchez et al. |
| 2018/0344518 A1 | 12/2018 | Tai |
| 2020/0069940 A1 | 3/2020 | Tai |
| 2021/0106831 A1 | 4/2021 | Tai |
| 2021/0283401 A1 | 9/2021 | Tai |
| 2021/0290429 A1 | 9/2021 | Tai |

FOREIGN PATENT DOCUMENTS

| | | |
|---|---|---|
| JP | 2010540177 A | 12/2010 |
| JP | 2011502586 A | 1/2011 |
| JP | 2014018508 A | 2/2014 |
| JP | 2015500113 A | 1/2015 |
| JP | 2015531661 A | 11/2015 |
| JP | 2016501074 A | 1/2016 |
| JP | 2017526479 A | 9/2017 |
| JP | 2017527428 A | 9/2017 |
| WO | WO-03105736 A1 | 12/2003 |
| WO | WO-2009046044 A1 | 4/2009 |
| WO | WO-2009061813 | 5/2009 |
| WO | WO-2013087885 A1 | 6/2013 |
| WO | WO-2014043661 A2 | 3/2014 |
| WO | WO-2014078630 A1 | 5/2014 |
| WO | WO-2015142838 A1 | 9/2015 |
| WO | WO-2016039768 A1 | 3/2016 |
| WO | WO-2016040670 A1 | 3/2016 |
| WO | WO-2016040676 A1 | 3/2016 |
| WO | WO-2016072875 A1 | 5/2016 |
| WO | WO-2017096007 A1 | 6/2017 |
| WO | WO-2019204198 A1 | 10/2019 |
| WO | WO-2019246318 A1 | 12/2019 |
| WO | WO-2020006536 A1 | 1/2020 |
| WO | WO-2021127195 A1 | 6/2021 |

OTHER PUBLICATIONS

Extended European Search Report for European Application No. 19822441.2, mailed Jun. 20, 2022, 12 pages.
International Preliminary Report on Patentability for International Application No. PCT/US2020/065636 dated Jun. 30, 2022, 8 pages.
Office Action for European Application No. 16871478.0, mailed Jan. 5, 2023, 8 pages.
Office Action for European Application No. 19822441.2, mailed Feb. 8, 2023, 6 pages.
Office Action for U.S. Appl. No. 17/047,754, mailed Feb. 14, 2023, 10 pages.
Office Action for U.S. Appl. No. 17/047,754, mailed Mar. 29, 2022, 9 pages.
Office Action for U.S. Appl. No. 17/047,754, mailed Oct. 11, 2022, 10 pages.

(56) References Cited

OTHER PUBLICATIONS

Peng, C-W. et al., "Influence of stimulus waveforms of high-frequency electrical current on nerve conduction block," Proceedings of the 4th International IEEE EMBS Conference on Neural Engineering, Antalya, Turkey, Apr. 29-May 2, 2009, pp. 72-75; DOI: 10.1109/NER.2009.5109237.
Examination Report No. 1 for Australian Application No. 2021261887, dated Jan. 17, 2023, 3 pages.
Office Action for U.S. Appl. No. 17/330,883, mailed Mar. 9, 2023, 8 pages.
Office Action for U.S. Appl. No. 17/330,883, mailed Sep. 26, 2022, 8 pages.
Final Notice of Reasons for Rejection for Japanese Application No. 2020-570509, mailed Nov. 9, 2023, 11 pages.
Notice of Reasons for Rejection for Japanese Application No. 2020-570509, mailed Mar. 20, 2023, 11 pages.
Office Action for European Application No. 19822441.2, mailed Dec. 1, 2023, 6 pages.
Apovian, C. M. et al., "Two-Year Outcomes of Vagal Nerve Blocking (vBloc) for the Treatment of Obesity in the ReCharge Trial," Obes. Surg., vol. 27, No. 1, pp. 169-176 (Jan. 2017).
Aronov, D. et al., "Analyzing the dynamics of brain circuits with temperature: design and implementation of a miniature thermoelectric device," J Neurosci Methods, vol. 197, Issue 1, pp. 32-47 (Apr. 2011).
Baylor, K. et al., "Peripheral nerve at extreme low temperatures 2: Pharmacologic modulation of temperature effects," Cryobiology, vol. 59, Issue 1, pp. 12-18 (Aug. 2009).
Bhadra, N. et al., "High-Frequency Electrical Conduction Block of Mammalian Peripheral Motor Nerve," Muscle Nerve, vol. 32, No. 6, pp. 782-790 (Dec. 2005).
Bhadra, N. et al., "Temporary persistence of conduction block after prolonged Kilohertz Frequency Alternating Current (KHFAC) on rat sciatic nerve," J Neural Eng., vol. 15, No. 1, pp. 1-15 (Feb. 2018).
Cattell, M. et al., "'The Inhibitory' effect of high-frequency stimulation and the excitation state of nerve," J Physiol, vol. 83, No. 4, pp. 407-415 (Mar. 1935).
Clausen, T., "Quantification of Na+,K + pumps and their transport rate in skeletal muscle: Functional significance," J. Gen Physiol, vol. 142, No. 4, pp. 327-345 (Oct. 2013).
Cuellar, J. M. et al., "Effect of High-Frequency Alternating Current on Spinal Afferent Nociceptive Transmission," Neuromodulation, vol. 16, Issue 4, pp. 318-327 (Aug. 2013).
Examination Report No. 1 for Australian Application No. 2016364743, dated Sep. 30, 2020, 5 pages.
Examination Report No. 2 for Australian Application No. 2016364743, dated May 21, 2021, 4 pages.
Extended European Search Report for European Application No. 16871478.0, mailed Jun. 19, 2019, 9 pages.
Extended European Search Report for European Application No. 19788392.9, mailed Nov. 17, 2021, 9 pages.
Finch, P. et al., "High-Frequency (10 kHz) Electrical Stimulation of Peripheral Nerves for Treating Chronic Pain: A Double-Blind Trial of Presence vs Absence of Stimulation," Neuromodulation, vol. 22, No. 5, pp. 529-536 (Jul. 2019).
Floras, J. S., "Sympathetic Nervous System Activation in Human Heart Failure," Journal of the American College of Cardiology, vol. 54, No. 5, pp. 375-385 (Jul. 2009).
Frankenhaeuser, B. et al., "The Action Potential in the Myelinated Nerve Fibre of Xenopus Laevis as Computed on the Basis of Voltage Clamp Data," J. Physiol., vol. 171, Issue 2, pp. 302-315 (Jun. 1964).
Franz, D. N. et al. "Mechanisms for differential block among single myelinated and non- myelinated axons by procaine," J Physiol., vol. 236, No. 1, pp. 193-210 (Jan. 1974).
Fudim, M. et al., "Splanchnic Nerve Block for Acute Heart Failure," Circulation, vol. 138, No. 9, pp. 951-953 (Aug. 2018).
Gaunt, R. A. et al., "Transcutaneously Coupled, High-Frequency Electrical Stimulation of the Pudendal Nerve Blocks External Urethral Sphincter Contractions," Neurorehabilitation and Neural Repair, vol. 23, No. 6, pp. 615-626 (Jul./Aug. 2009).
Hodgkin, A. L. et al., "A Quantitative Description of Membrane Current and Its Application to Conduction and Excitation in Nerve," J. Physiol., vol. 117, Issue 4, pp. 500-544 (Aug. 1952).
Hoogeveen, J. F. et al., "Ultrastructural changes in the rat sciatic nerve after local hyperthermia," International Journal of Hyperthermia, vol. 9, Issue 5, pp. 723-730 (Sep.-Oct. 1993).
Imoto, H. et al., "Use of a Peltier chip with a newly devised local brain-cooling system for neocortical seizures in the rat." Technical note. J. Neurosurg., vol. 104, Issue 1, pp. 150-156 (Jan. 2006).
International Search Report and Written Opinion for International Application No. PCT/US2016/064364, mailed Mar. 17, 2017, 12 pages.
International Search Report and Written Opinion for International Application No. PCT/US2019/027471, mailed Jul. 2, 2019, 14 pages.
International Search Report and Written Opinion for International Application No. PCT/US2019/038065, mailed Oct. 31, 2019, 9 pages.
International Search Report and Written Opinion for International Application No. PCT/US2020/065636, mailed Mar. 24, 2021, 12 pages.
Jia, J. et al., "Cold Nerve Injury is Enhanced by Intermittent Cooling," Muscle and Nerve, vol. 22, Issue 12, pp. 1644-1652 (Dec. 1999).
Klumpp, D. et al., "Irreversible Differential Block of A- and C-Fibres Following Local Nerve Heating in the Cat," J. Physiol., vol. 298, pp. 471-482 (1980).
Leuchtag, H. R., "Fit of the dielectric anomaly of squid axon membrane near heat-block temperature to the ferroelectric Curie-Weiss law," Biophysical Chemistry, vol. 53, Issue 3, pp. 197-205 (Feb. 1995).
Liu, B. et al., "Use Dependence of Heat Sensitivity of Vanilloid Receptor TRPV2," Biophysical Journal, vol. 110, Issue 7, pp. 1523-1537 (Apr. 2016).
Liu, H. et al., "Post stimulus effects of high frequency biphasic electrical current on a fibre's conductibility in isolated frog nerves," Journal of Neural Engineering, vol. 10, No. 3, May 2013, 36024, 14 pages.
Liu, H. et al., "The role of slow potassium current in nerve conduction block induced by high-frequency biphasic electrical current," IEEE Transactions on Biomedical Engineering, vol. 56, No. 1, pp. 137-146 (Jan. 2009).
Long, M. A. et al., "Using temperature to analyze temporal dynamics in the songbird motor pathway," Nature, vol. 459, Issue 7219, pp. 189-194 (Nov. 2008).
Luzzati, V. et al., "Structural and Electrophysiological Effects of Local Anesthetics and of Low Temperature on Myelinated Nerves: Implication of the Lipid Chains in Nerve Excitability," J. Mol. Biol., vol. 286, pp. 1389-1402 (Jan. 1999).
Miles, J. D. et al., "Effects of ramped amplitude waveforms on the onset response of high-frequency mammalian nerve block," J. Neural. Eng., vol. 4, No. 4, pp. 390-398 (Dec. 2007).
Office Action for U.S. Appl. No. 15/780,748, mailed Aug. 6, 2020, 15 pages.
Paintal, A. S., "Block of Conduction in Mammalian Myelinated Nerve Fibres by Low Temperatures," J. Physiol., vol. 180, No. 1, pp. 1-19 (Sep. 1965).
Pertusa, M. et al., "Mutagenesis and Temperature-Sensitive Little Machines," Chapter 11 In: Mutagenesis, InTech, pp. 221-246 (Aug. 2012).
Reboul, J. et al., "The action of alternating currents upon the electrical excitability of nerve," The American Journal of Physiology, vol. 125, No. 2, pp. 205-215 (Feb. 1939).
Rosenblueth, A. et al., "The blocking and deblocking effects of alternating currents on nerve," Am J Physiol, pp. 251-264 (Nov. 1938).
Rothman, S. et al., "Local Cooling: A Therapy for Intractable Neocortical Epilepsy," Epilepsy Currents, vol. 3, No. 5, pp. 153-156 (Sep./Oct. 2003).
Sarr, M. G. et al., "The Empower Study: Randomized, Prospective, Double-Blind, Multicenter Trial of Vagal Blockade to Induce Weight

(56) References Cited

OTHER PUBLICATIONS

Loss in Morbid Obesity," Obes. Surg., vol. 22, No. 11 pp. 1771-1782 (Nov. 2012); published online Sep. 2012.

Schumacher, S. et al., "Extradural Cold Block for Selective Neurostimulation of the Bladder: Development of a New Technique," The Journal of Urology, vol. 161, No. 3, pp. 950-954 (Mar. 1999).

Soin, A. et al., "High-Frequency Electrical Nerve Block for Postamputation Pain: A Pilot Study," Neuromodulation: Technology at the Neural Interface, vol. 18, Issue 3, pp. 197-206 (Apr. 2015).

Stecker, M. M. et al., "Peripheral nerve at extreme low temperatures 1: Effects of Temperature on the action potential," Cryobiology, vol. 59, No. 1, pp. 1-11 (Aug. 2009).

Tai, C. et al., "Block of External Urethral Sphincter Contraction by High Frequency Electrical Stimulation of Pudendal Nerve," The Journal of Urology, vol. 172, No. 5, Pt. 1, pp. 2069-2072 (Nov. 2004).

Tai, C. et al., "Simulation of Nerve Block by High-Frequency Sinusoidal Electrical Current Based on the Hodgkin-Huxley Model," IEEE Transactions on Neural Systems and Rehabilitation Engineering, vol. 13, No. 3, pp. 415-422 (Sep. 2005).

Van Buyten. J-P. et al., "High-Frequency Spinal Cord Stimulation for the Treatment of Chronic Back Pain Patients: Results of a Prospective Multicenter European Clinical Study," Neuromodulation, vol. 16, Issue 1, pp. 59-66 (Feb. 2013).

Vujaskovic, Z. et al., "Effects of intraoperative hyperthermia on peripheral nerves: Neurological and electrophysiological studies," International Journal of Hyperthermia, vol. 10, Issue 1, pp. 41-49 (Jan.-Feb. 1994); published online Jul. 2009.

Waataja, J. J. et al., "Effects of high-frequency alternating current on axonal conduction through the vagus nerve," Journal of Neural Engineering, vol. 8, No. 5, pp. 1-7 (Sep. 2011).

Yang, G. et al., "Post-Stimulation Block of Frog Sciatic Nerve by High-Frequency (kHz) Biphasic Stimulation," Med. Biol. Eng. Comput., vol. 55, No. 4, pp. 585-593 (Apr. 2017).

Yang, G. et al., "Pudendal nerve stimulation and block by a wireless-controlled implantable stimulator in cats," Neuromodulation, vol. 17, No. 5, pp. 490-496 (Jul. 2014).

Zhang, X. et al., "Mechanism of Nerve Conduction Block Induced by High-Frequency Biphasic Electrical Currents", IEEE Trans Biomed Eng., vol. 53, No. 12, Pt. 1, pp. 2445-2454 (Dec. 2006).

Zhang, Z. et al., "Conduction block of mammalian myelinated nerve by local cooling to 15-30° C. after a brief heating," J Neurophysiol, vol. 115, Issue 3, pp. 1436-1445 (Mar. 2016).

Extended European Search Report for European Application No. 24156128.1 mailed Jul. 19, 2024, 7 pages.

Office Action and Search report for Chinese Application No. CN201980054662.8 dated Nov. 11, 2023, 14 pages.

Office Action for Australian Patent Application No. AU2019288384 dated Mar. 14, 2024, 3 pages.

Office Action for Canadian Patent Application No. CA3161124 dated Mar. 6, 2024, 5 pages.

Office Action for Japanese Patent Application No. 2022-527142 mailed Jul. 2, 2024, 8 pages.

* cited by examiner

| Distance | Temperature |
|----------|-------------|
| 0mm      | 45.1C       |
| 5mm      | 44.2C       |
| 10mm     | 43.6C       |
| 15mm     | 43.1C       |

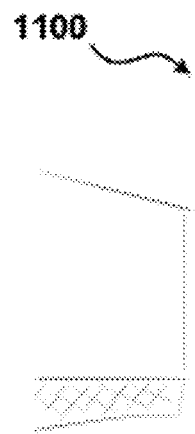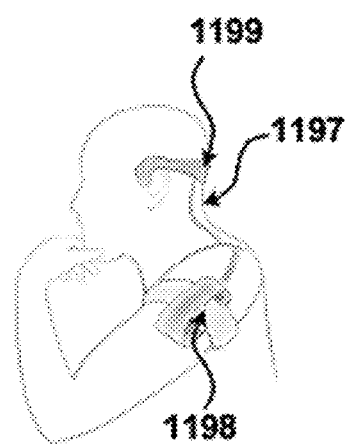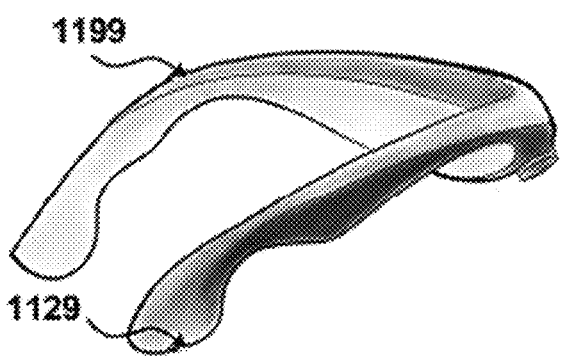
FIG. 11A
FIG. 11B
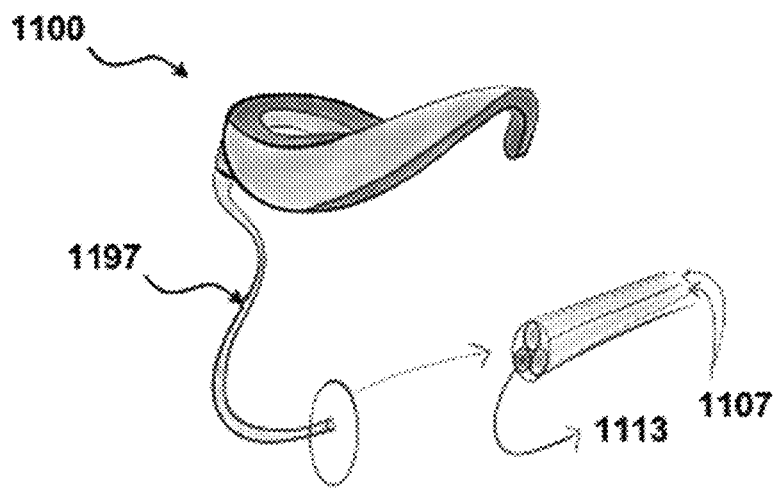
FIG. 11C

1570

1570

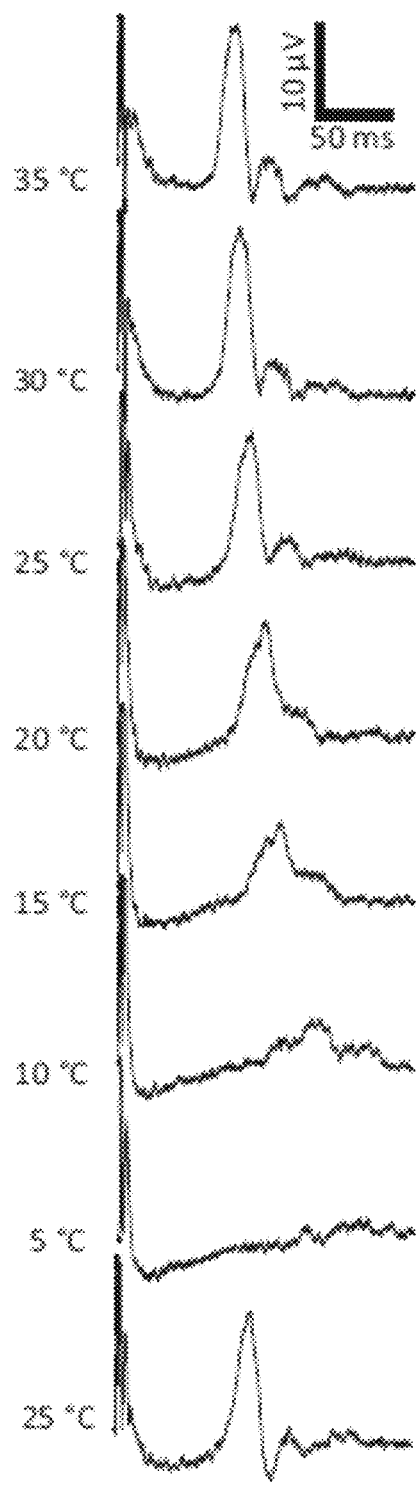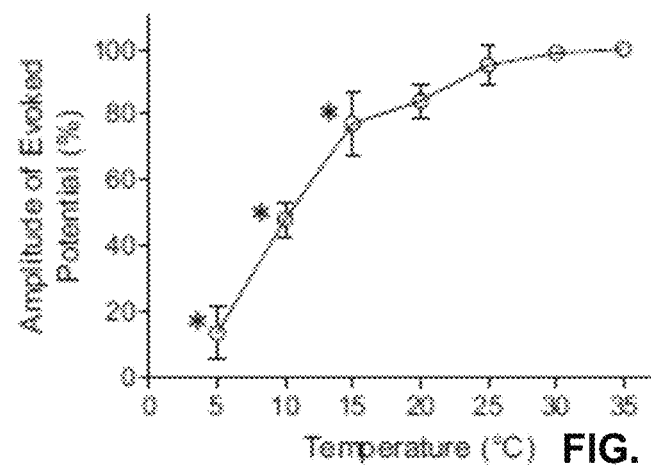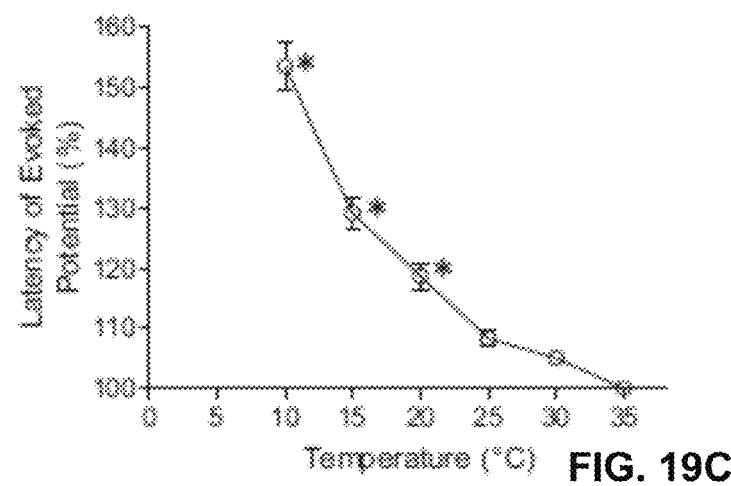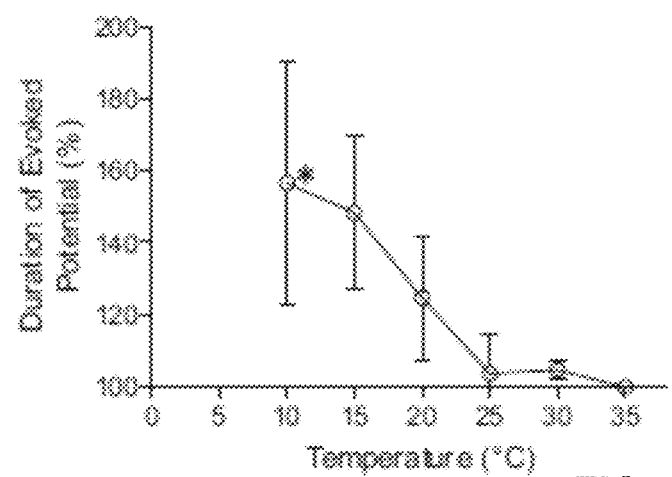
FIG. 19A
FIG. 19B
FIG. 19C
FIG. 19D

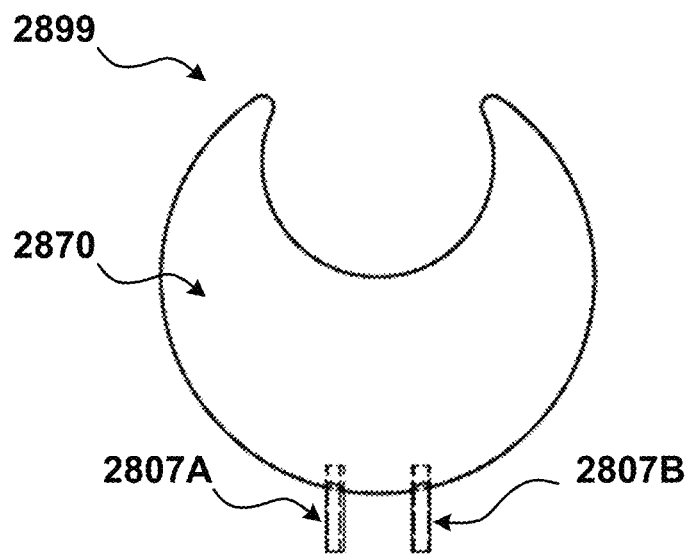
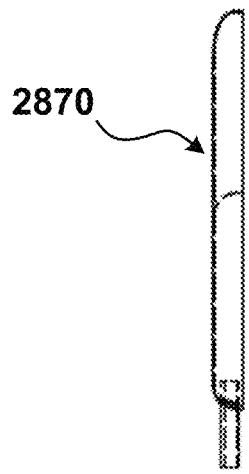
FIG. 28A
FIG. 28B
FIG. 28C
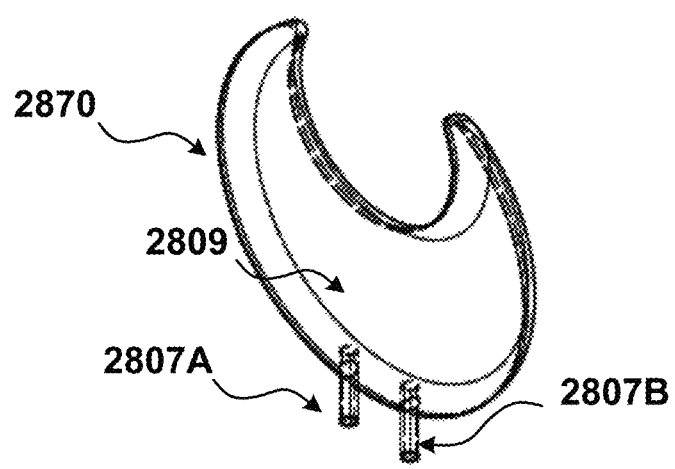
FIG. 28D

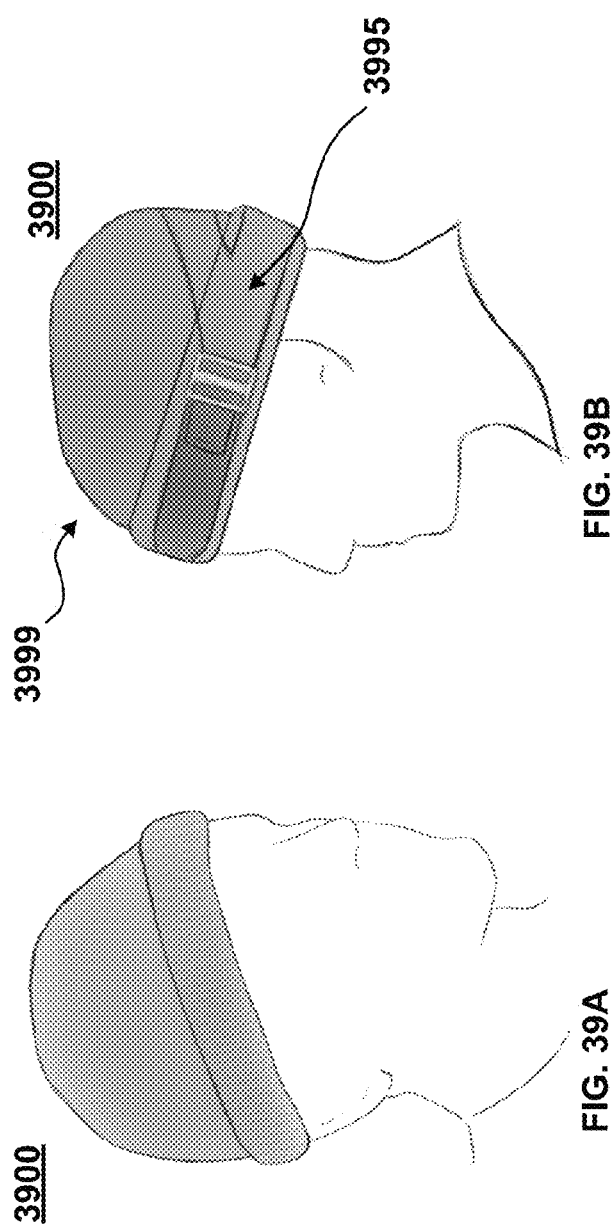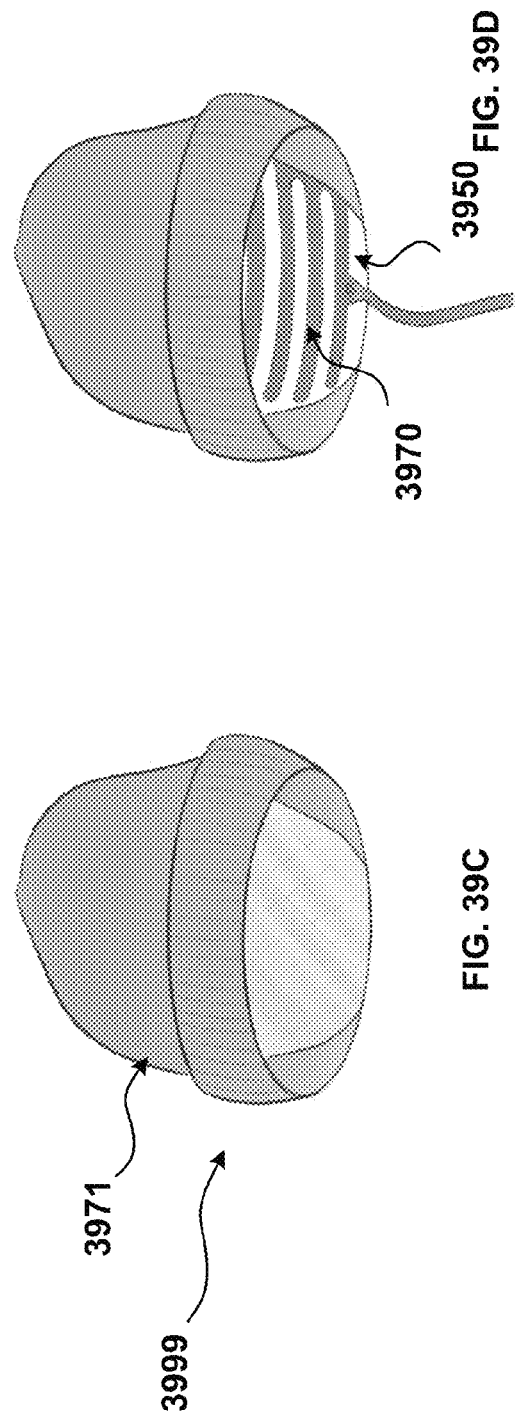

APPARATUS AND METHOD FOR THERMAL BLOCKADE OF NERVES

CROSS REFERENCE TO RELATED APPLICATIONS

The present application is a continuation-in-part of and claims priority to PCT Application Number PCT/US2019/38065, entitled "Systems and Methods for Thermal Blockade of Nerves," filed Jun. 19, 2019, which claims priority to and the benefit of U.S. Provisional Pat. App. No. 62/686,712, entitled "Devices, Uses and Methods for Reversible Nerve Block at Moderate Temperatures," filed Jun. 19, 2018. The present application is a continuation of and claims priority to PCT Application No. PCT/US2020/065636, entitled "Apparatus and Method for Thermal Blockade of Nerves," filed Dec. 17, 2020, which claims priority to U.S. Provisional Pat. App. Ser. No. 62/949,969, filed Dec. 18, 2019, entitled "Apparatus and Method for Thermal Blockade of Nerves." The present application is also related to PCT Application No. PCT/US2016/064364, entitled "Device and Method for Nerve Block by Local Cooling to Room Temperature," filed Dec. 1, 2016, which claims priority to and the benefit of U.S. Provisional Pat. App. No. 62/262,445, entitled "Nerve Block by Local Cooling to Room Temperature," filed Dec. 3, 2015. The entire disclosure of each of the foregoing is hereby incorporated herein by reference in its entirety.

STATEMENT REGARDING FEDERALLY SPONSORED RESEARCH OR DEVELOPMENT

This invention was made with Government support under grants DK-094905, DK-102427, and DK-111382 awarded by the National Institutes of Health, National Institutes of Diabetes and Digestive and Kidney Diseases. This invention was also made with Government support under grant R41NS115460 awarded by the National Institutes of Health, National Institute of Neurological Disorders and Stroke, as well as under grants 1913403 and 2026112 awarded by the National Science Foundation. The Government has certain rights in the invention.

BACKGROUND

The present disclosure relates generally to methods and apparatuses for manipulating temperature of a tissue of a mammal to control nerve conduction. Thermal modulation of nerves may be useful in the treatment of many conditions. There is a need for flexibly and/or efficiently implemented methods and/or apparatuses for delivering controlled thermal modulation to mammalian tissue.

SUMMARY

Embodiments disclosed include an apparatus, comprising an energy source, a controller, a first heat exchanger, a thermal applicator, a second heat exchanger, and a fluid conduit. The first heat exchanger is coupled to the thermal energy source and configured to receive thermal energy therefrom. The thermal applicator is configured to be disposed and secured to the anatomy of a subject having a nerve therein, in contact with the skin of the anatomy and overlying a treatment portion of the nerve. The thermal applicator is configured to transfer thermal energy to the skin or tissue to raise the temperature of the treatment portion of the nerve above a physiologic temperature. The second heat exchanger is coupled to the thermal applicator and configured to transfer thermal energy thereto. The fluid conduit has a first portion coupled to the first heat exchanger and a second portion coupled to the second heat exchanger. The fluid conduit is configured to have fluid circulated therethrough to convey thermal energy from the thermal energy source via the first heat exchanger and to the thermal applicator via the second energy at a temperature. The fluid is circulated at a thermal energy delivery rate and/or power sufficient to raise the temperature of the treatment portion of the nerve to a predetermined temperature above the physiologic temperature and maintain the temperature for a predetermined time. In some embodiments the fluid temperature is then adjusted at a predetermined rate to a predetermined subsequent temperature, for example below the physiologic temperature, and maintained for a predetermined time. All predetermined times and temperatures are based on algorithms that can be adapted based on user inputs.

Embodiments disclosed include a method comprising delivering thermal energy to a treatment portion of a target nerve in the body of a subject mammal via a thermal applicator disposed in operative relationship with the treatment portion. The delivery thermal energy is to increase a temperature of the treatment portion to a first desired temperature above a physiologic temperature of the nerve. The method includes continuing to deliver thermal energy to the treatment portion via the thermal applicator to maintain the temperature of the treatment portion at the first desired temperature for a sufficient time to achieve a first desired thermal modulation of the target nerve. The method further includes, after the continuing to deliver thermal energy, withdrawing thermal energy from the treatment portion via the thermal applicator to decrease a temperature of the treatment portion to a second desired temperature below the physiologic temperature of the nerve. The method further includes continuing to withdraw thermal energy from the treatment portion via the thermal applicator to maintain the temperature of the treatment portion at the second desired temperature for a sufficient time to achieve a second desired thermal modulation of the target nerve. Repeated cyclic thermal modulation may maintain the desired modulation effect and increase the post-therapeutic durability of the effect.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 11A-B are schematic illustrations of use and implementation of a thermal neural modulation system, according to an embodiment.

FIG. 11C is an illustration of a coupling portion of the system of FIGS. 11A-B.

FIGS. 19A-D show physiological traces and analyses measuring effects of temperature on nerve conduction, using a thermal modulation system according to an embodiment.

FIGS. 28A-D are schematics of top view, side view, orthogonal side view, and a perspective view of an applicator portion of a thermal modulation system, according to an embodiment.

FIGS. 39A-39D are illustrations of the applicator portion of a thermal modulation system for treatment of a head, according to an embodiment . . .

DETAILED DESCRIPTION

Figure 1:
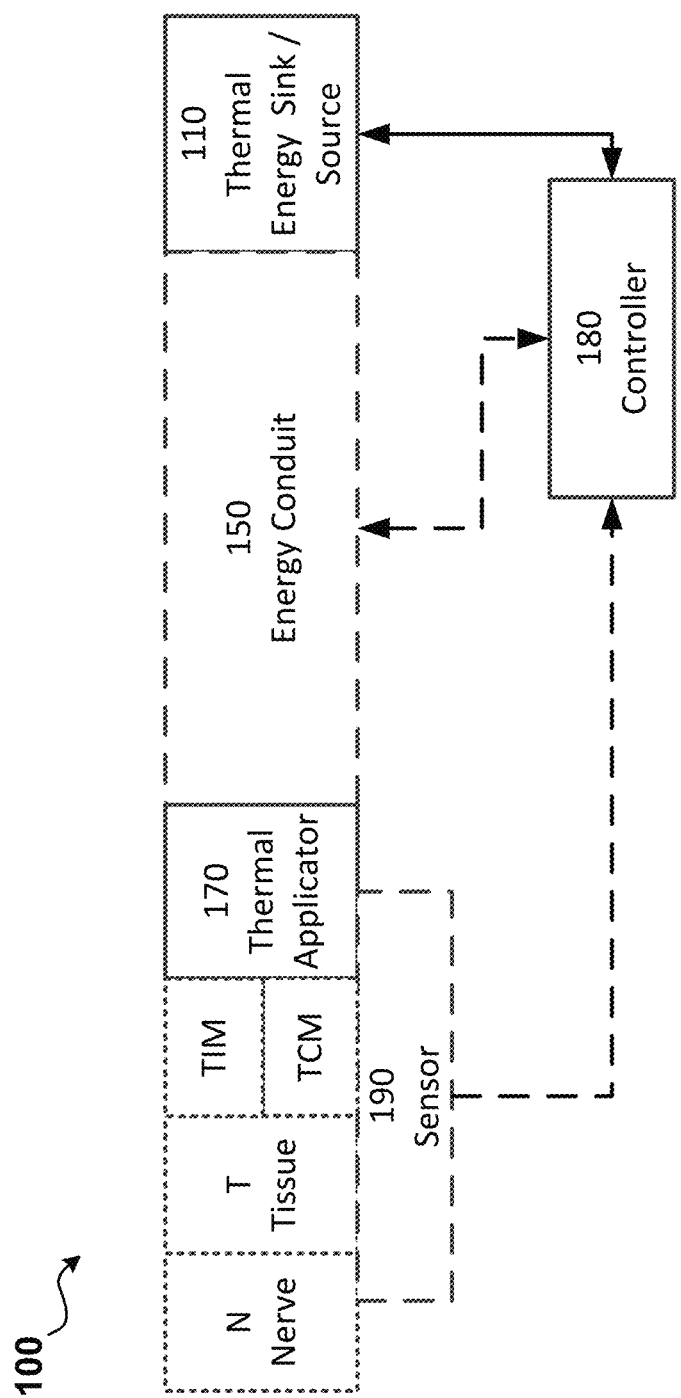
FIG. 1 is a schematic illustration of a thermal neural modulation system, according to an embodiment.

Devices and methods are described herein for modulating, i.e. stimulating and/or blocking, transmission of signals in one or more nerves in the body of a human or other mammal by thermal mechanisms.

Such thermal modulation of nerves may be useful in the treatment of many conditions. As used herein, the terms "treatment" or "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof.

A non-limiting list of example conditions and associated nerves, nerve groups/types, and treatment locations is shown below in Table 1.

TABLE 1

| Condition | Nerve(s) | Nerve Group(s) [A, B, C]/ Type(s) [α, β, γ, δ] | Treatment Location |
|---|---|---|---|
| Head and/or neck pain with or without migraine or associated neuralgia | Occipital, trigeminal, supraorbital, nerves including surface/superficial branches and larger named branches, as well as vestibulcochlear, glossopharyngeal, olfactory, optic, vagus, accessory, hypoglossal oculomotor, trochlear, abducent, facial, and trigeminal nucleus caudalis, trigeminal ganglion, C1-C2-C3 dorsal root ganglia | Primarily likely Aδ, C | Head and/or neck |
| Chronic knee pain following total knee replacement surgery | Saphenous, femoral, common peroneal, tibial, obturator, and genicular nerves | Primarily likely Aδ, C | knee |
| Pain associated with osteoarthritis | Nerves in intra-articular region of knee | Primarily likely Aδ, C | knee |
| Severe chronic pain | Spinal cord, e.g. dorsal root ganglion and/or dorsal nerve roots. | Sensory, A and C fibers | Spinal column |
| Wound or surgical site | Associated nerve(s) in proximity to the break in the skin | Primarily likely Aδ, C | Local to IV, wound, puncture or surgical site |
| Obesity | Vagus nerve abdominal branch | For instance largely Aδ | A-δ (internal orders) |
| Heart failure | Sympathetic, greater splanchnic, lesser splanchnic, sympathetic trunks | May or may not require selective targeting of specific nerve types | Intravascular stimulation of nerve /Implantable stimulator |
| Urinary retention | Pudendal | May or may not require selective targeting of specific nerve types | Implantable device close to target nerve |
| Muscle spasms | Nerve innervating muscle | Primarily Aα and β fibers | Implantable device close to target nerve |
| Cardiovascular disease | Vagus | May or may not require selective targeting of specific nerve types | Implantable device close to target nerve |
| Pelvic and other conditions | Median, ilioinguinal, tibial, sciatic, intercostal, peroneal, femora, axillary, supracapular, sura, ulnar, radial, lateral femoral cutaneous | Primarily likely Aδ, C | Wrist, elbow, finger, hand, thoracic, abdominal, back, shoulder, hip, leg, ankle, finger and/or toes, etc |

The disclosed devices and methods are contemplated for use in the monitoring, diagnosis, or treatment of any such conditions or diseases wherein a nerve stimulation or block is suitable for the analysis.

As used herein, the "blockade" of a nerve refers to situations where the neurons do not propagate action potentials or have reduced amplitudes of evoked action potentials. A blockade of a nerve may be partial, where a lower percentage of neurons propagate action potentials than do neurons which are not blocked or when amplitudes of evoked action potentials are reduced relative to amplitudes of action potentials evoked by neurons, which are not blocked.

As used herein, the "stimulation" of a nerve refers to situations in which the nerve's functional behavior, for example extent of nerve conduction, is altered as a result of temperature modulation of the nerve.

Thermal modulation may refer to heating only, cooling only, alternation of heating and cooling, or simultaneous heating and cooling of a treatment portion of the nerve. It is well known that extreme heating or cooling of a nerve over relatively long durations of time may lead to irreversible damage to that nerve. For instance, temperatures greater than or equal to about 50° C. and less than or equal to about 5° C. have been used in methods known in the art for single-temperature nerve blocks. However, applying these extreme temperatures to a nerve may cause permanent damage within minutes or hours.

In contrast, the thermal modulation (stimulation and/or blockade) produced by the devices and methods disclosed herein is reversible. As used herein, "reversible" means the ability for a nerve with a partial or complete blockade to regain the majority of useful nerve function within a period of about one to three months following the blockade-inducing treatment. By this definition of "reversible," ablation is not considered to be reversible.

Reversible thermal modulation according to disclosed embodiments may include moderately heating and/or moderately cooling a defined section (e.g. treatment portion) of a nerve. As used herein, "moderate cooling" means cooling below body temperature to a level and for a duration in which any nerve damage that may occur is considered to be reversible. As used herein, "moderate heating" means heating above body temperature to a level and for a duration in which any nerve damage that may occur is considered to be reversible.

In some embodiments, complete or partial nerve blockade may be achieved by one or more moderate heating steps. In other embodiments, an initial moderate heating step may be followed by one or more moderate cooling steps, and the previous moderate heating step may allow for higher cooling temperatures to be applied to generate a more complete or partial nerve blockade than would otherwise be possible or acceptable without the initial heating step. This may avoid the use of potentially permanent damage-inducing extreme temperatures by the combination of the initial moderate heating and optional subsequent moderate cooling steps.

Thus, for example, a treatment method may include first heating a treatment portion of a nerve at a moderate temperature for a duration of time at a temperature above body temperature but below a temperature in which irreversible damage may be done to the nerve over the duration. During moderate heating, nerve conduction may be partially or completely reduced and nerves may be observed to have a partially or completely reduced evoked action potential or signal. Following moderate heating of the treatment portion of the nerve, moderate cooling may optionally be administered for a duration of time at a temperature below body temperature but above a temperature in which irreversible damage may be done to the treatment portion of the nerve over the duration.

During moderate cooling, the temperature of the target portion of the target nerve may be held at a cooling temperature or may be reduced in a series of steps of decreasing cooling temperatures. The cooling steps may be of equal or unequal duration and may be of equal or unequal magnitude of temperature.

The transition between heating and cooling phases may occur in less than about one minute, between about one minute and about three minutes, or between about three minutes and about five minutes. In some embodiments, the transition in temperature between heating and cooling phases may occur between about five minutes and about 25 minutes. In other embodiments, the transition in temperature between heating and cooling phases may occur between about 25 minutes and about 60 minutes.

For example, moderate cooling includes cooling a treatment portion of nerve to a temperature ranging from about 10-15° C. to about 30° C. for a duration of at least about 2-5 minutes to about 90 or 120 minutes or more. For example, moderate heating may include heating a treatment portion of nerve to a temperature ranging from about 39° C. to about 50° C. for a duration of not less than about 2-10 minutes to about 90 or 120 minutes or more.

In some embodiments, a cooling phase may be within a range of about −5° C. to about (C. In other embodiments, the cooling phase may be within a range of about 0° C. to about 15° C. In other embodiments, the cooling phase may be within a range of about 15° C. to about 35° C. In some embodiments, a heating phase may be within a range of about 40° C. to about 51° C. In other embodiments, the heating phase may be within a range of about 40° C. to about 49° C. In other embodiments, the heating phase may be within a range of about 40° C. to about 45° C.

Reversible thermal modulation or blockade according to disclosed embodiments can produce preferential and/or selective blockade of different types of nerve fibers. For example, blockade of myelinated, A-β fibers and A-δ fibers, and unmyelinated, C-fibers can be achieved. In some instances, preferential partial and/or complete blockade of smaller-diameter nerve fibers including pain (or other undesirable sensory signals, such as those resulting from thermal, mechanical or chemical noxious stimulation) signalling C-fibers and/or A-δ fibers can be achieved while less significantly or not effecting blockade of larger-diameter motor signalling A-β and A-α fibers. In some instances, application of moderate heating and/or moderate cooling to a treatment portion of a target C-fiber and/or a A-δ fiber nerve that is sufficient to blockade C-fibers and/or A-δ fibers may be desirable to produce relief from pain (or other undesirable sensory signals), but that same level, duration, and/or sequence of moderate heating and/or moderate cooling may also be sufficient to blockade motor A-β and/or A-α fibers that are adjacent to, or otherwise in the thermal treatment zone of, the pain signalling C-fibers and/or A-δ fibers. However, in many clinical applications blocking painful sensations without blocking motor function may be preferred, which requires selective blockade of the C-fibers and/or A-δ fibers without blockading the motor A-β and/or A-α fibers.

This selectivity can be achieved by taking advantage of the different temperatures at which moderate heating of a treatment portion of a target nerve can produce blockade upon moderate cooling of A-α, A-β, A-δ fibers and C-fibers, i.e. C-fibers and/or A-δ fibers can be blockaded with moderate cooling after moderate warming at a lower temperature than A-β fibers. Thus, according to disclosed embodiments a treatment region of a subject's body can be subjected to moderate heating to a temperature sufficient to initiate room-temperature (greater than or equal to about 15° C.) blockade of a treatment portion of target C-fibers and/or target A-δ fibers but below the temperature required to produce room-temperature blockade of A-β fibers upon moderate cooling. This selectivity can be achieved by taking advantage of the different temperatures at which moderate heating of a treatment portion of a target nerve can produce blockade upon moderate cooling of any and all nerve fiber types including for example A-α, A-β, A-δ fibers and C-fibers, i.e. C-fibers and/or A-δ fibers can be blockaded with moderate cooling after moderate warming at a lower temperature that A-β fibers. Thus, according to disclosed embodiments a treatment region of a subject's body can be subjected to moderate heating to a temperature sufficient to initiate room-temperature (greater than or equal to about 15° C.) blockade of a treatment portion of target C-fibers and/or target A-δ fibers but below the temperature required to produce room-temperature blockade of A-β fibers upon moderate cooling.

In some implementations, selectivity can be achieved by using a thermal modulation system to achieve a first temperature for a duration that is sufficient to initiate partial or complete blockade, and/or to pre-condition without necessarily initiating partial or complete blockade, a target portion of C-fibers and/or A-δ fibers, but insufficient to initiate blockade or have any pre-conditioning effect on A-β fibers, such that following the initiation of blockade at warm temperatures or pre-conditioning without initiating blockade, thermal modulation can be administered at a relatively smaller degree of temperature shift and thus reduce impact of thermal modulation on the A-β fibers carrying motor signals. For example, in some instances, a portion of C-fibers and/or A-δ fibers that carry pain signals can be primed or pre-conditioned or pre-warmed or warmed to a temperature of about ≤45° C. by heating and then thermally modulated by cooling. Such a pre-warming can aid in thermal modulation of the pre-conditioned C-fibers and/or A-δ fibers by enabling cooling to a higher temperature than would have been required without the pre-conditioning or pre-warming. For example, non pre-conditioned C-fibers and/or Aδ fibers may have to be thermally modulated at temperatures colder than 15° C., 10° C. or 5° C. to initiate and/or achieve blockade of pain signalling, whereas pre-conditioned C-fibers and/or A-δ fibers may be thermally modulated at higher temperatures, for example, room temperature, or at or near 25° C. or 20° C. or 15° C. to initiate and/or achieve blockade of pain signalling. The pre-warming may selectively prime or pre-condition C-fibers and/or A-δ fibers and may have a lesser or no pre-conditioning effect on A-β fibers. The pre-conditioning of C-fibers and/or A-δ fibers may be such that the thermal modulation at higher temperatures following pre-warming (e.g., room temperature, or at or near 25° C. or 20° C. or 15° C.) can selectively initiate and/or achieve partial or complete blockade of C-fibers and/or A-δ fibers while the more heavily myelinated A-β fibers lying adjacent are largely unaffected in their motor signalling.

Desired selectivity can also be achieved by taking advantage of the different durations over which A-β fibers, C-fibers and A-δ fibers recover from the pre-heating effect (by application of appropriate moderate heating). It has been shown that A-β fibers recover function more quickly than C-fibers and/or A-δ fibers. Thus, according to other disclosed embodiments, a treatment region of a subject's body may be subjected to moderate heating to a temperature sufficient to raise the temperature of a treatment portion of a target C-fiber and/or a target A-δ fiber nerve to a temperature for a duration sufficient to pre-condition the C-fiber and/or A-δ fibers, and an adjacent A-β fiber, but not subjected to moderate cooling until after the A-β fibers lose their pre-conditioning but before the target C-fibers and/or the target A-δ fibers have lost their pre-conditioning. Alternately the treatment portion of the target nerve in this example could be cooled immediately after warming to continue block of A-δ fibers, C-fibers, and the A-β fibers. The signalling via A-β fibers and associated motor function may return for example within about 10-60 minutes while pain signalling via C-fiber and/or A-δ fiber transmission may remain blocked for an extended period while held at moderate cool temperatures. Warming the treatment portion of the target nerve to 45° C. or another temperature below that which is required to initiate or maintain A-β fiber nerve block will then perpetuate the C-fiber and/or the A-δ fiber nerve block without blocking motor (A-β fiber) function.

In some implementations, a relatively lesser degree of delivery (shorter times and/or temperatures closer to body temperature) of thermal energy may be sufficient to pre-condition or initiate partial or complete blockade of C-fibers, compared to a degree of delivery of thermal energy that may be sufficient to pre-condition or initiate partial or complete blockade of A-δ fibers. In turn, a relatively lesser degree of delivery of thermal energy may be sufficient to pre-condition or initiate partial or complete blockade of A-δ fibers, compared to a degree of delivery of thermal energy that may be sufficient to pre-condition or initiate partial or complete blockade of A-β fibers. In some implementations, a relatively lesser degree of withdrawal of thermal energy (e.g., following a pre-condition or moderate warming) may be sufficient to blockade C-fibers compared to a degree of withdrawal of thermal energy that may be sufficient to blockade A-δ fibers. In turn a relatively lesser degree of withdrawal of thermal energy may be sufficient to blockade A-δ fibers compared to a degree of withdrawal of thermal energy that may be sufficient to blockade A-β fibers.

Figure 2:
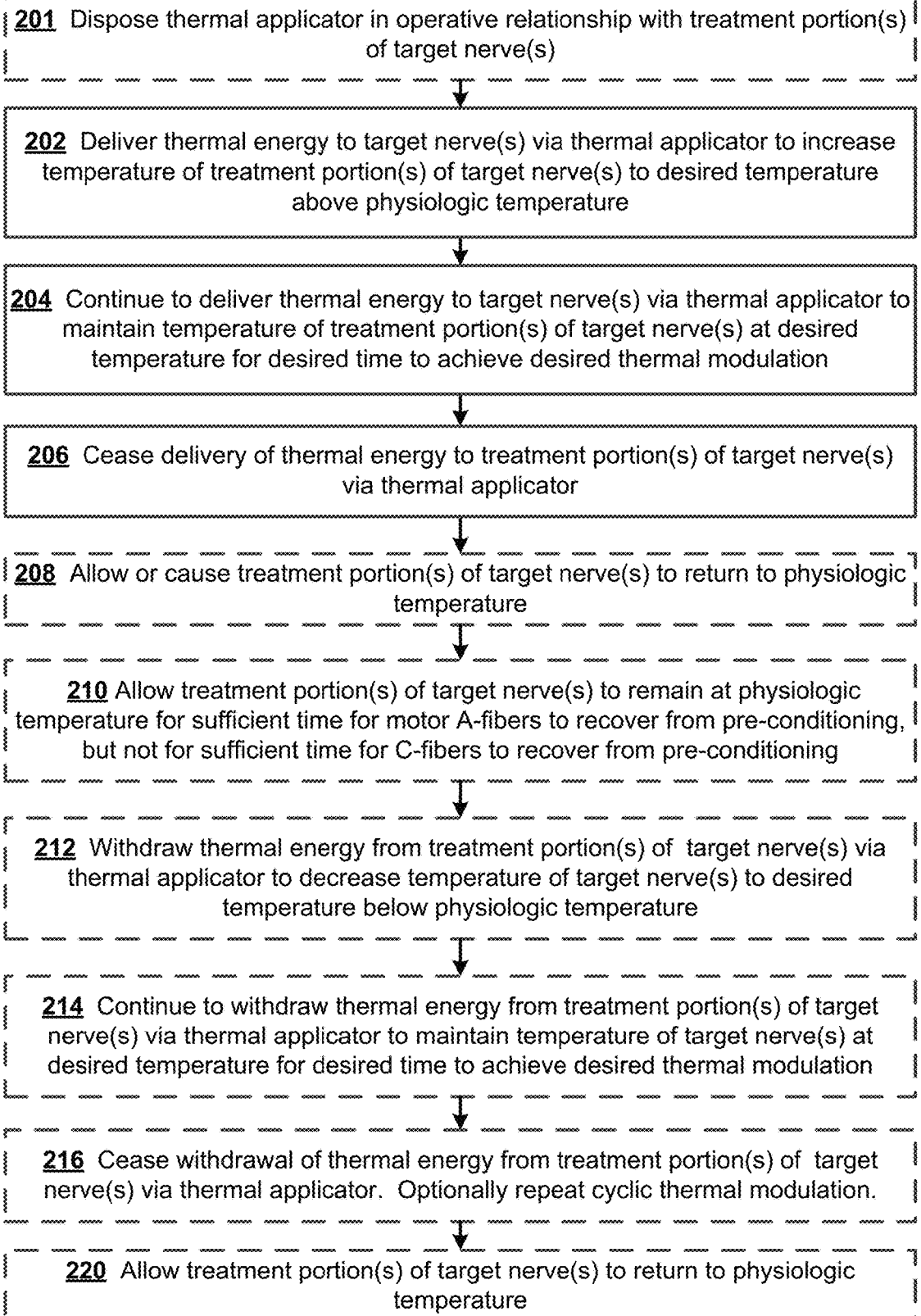
FIG. 2 is a flowchart illustrating a method of using a thermal neural modulation system, according to an embodiment.

A method of thermal neural modulation of one or more nerves is illustrated in FIG. 2.

In some implementations, the method 200 of FIG. 2 can optionally include step 201 to dispose a thermal applicator in operative relationship with one or more treatment portions of the target nerve(s). The treatment portions and/or the nerve types can include those listed in Table 1 as well as any other overactive nerve whose reversible block could be expected to be beneficial. In some instances, the thermal applicator can be disposed on the treatment portions based on any number of suitable parameters including the condition being treated, accessibility of the target nerve(s), amount, degree, and/or nature of thermal neural modulation desired, temporal features of thermal neural modulation of the target nerve(s) (e.g., speed of modulation). The thermal applicator can be disposed in any suitable manner such that thermal energy can be efficiently transferred from the thermal applicator to the target nerve(s). For example, the thermal applicator can be disposed via placement on a surface of a patient's body at or adjacent to a portion of the body through which a treatment portion(s) of the target nerve(s) are expected to traverse. In some instances, for example, the thermal applicator can be disposed via implantation at or adjacent to the treatment portion(s) of the target nerve(s). In some instances, the thermal applicator can be disposed at a predetermined location with respect to the treatment portion(s) of the target nerve(s) (e.g., at a predetermined distance from the treatment portion(s) of the target nerve(s)) to effect a predefined thermal neural modulation of the target nerve(s).

The method 200 includes, at 202, a step to deliver thermal energy to the target nerve(s) via the thermal applicator to increase the temperature of the treatment portion(s) of the target nerve(s) (i.e., heating the target nerve(s)) to a desired temperature above physiologic temperature. For example, the delivery of thermal energy can be targeted to raise the temperature of the treatment portion(s) of the target nerve(s) to a temperature of about 40-55° C. to achieve a desired thermal neural modulation of the target nerve(s).

In some instances, the thermal energy can be delivered via a thermal applicator disposed in operative relationship with the treatment portion of the target nerve(s) as described above. The delivery of thermal energy can be performed using any suitable method of transfer of thermal energy. In some instances, the delivery of thermal energy can be from a source of thermal energy. The source of thermal energy can be any suitable element at a temperature higher than the physiologic temperature from which thermal energy can be extracted. In some instances, the source of thermal energy can be an element that can be maintained at a suitable temperature (e.g., heated and/or cooled) in a controlled manner to deliver the thermal energy to the treatment portion(s) of the target nerve(s) and to increase the temperature of the treatment portion(s) of the target nerve(s) to a desired temperature. In some instances, the thermal applicator to deliver thermal energy may include an electrical resistive heating element, an inductive heating element, a Peltier heater, microwave heating elements, radio frequency heating elements, ultrasound emitters, infrared emitters, a tube containing temperature-controlled fluid, or any other suitable heating means capable of providing the desired heating temperatures and durations. In some instances, the thermal applicator may receive energy from a separate energy source that is converted to heat. For example, an implanted element may receive inductive energy from the energy source that is converted into heat by the implanted element.

In some instances, energy can be directed from the source to be delivered to the treatment portion of the target nerve(s) via an energy conduit. In some instances, the energy delivered can be thermal energy, and the delivery of thermal energy can be via a thermally conductive medium. In some instances, the delivery of thermal energy can be controlled using any suitable mechanism to control the transfer of thermal energy from the source of thermal energy to the treatment portion of the target nerve(s). For example, the thermal energy can be delivered at a controlled rate (e.g., rate of heat transfer) for a controlled period of time such that the treatment portion(s) of the target nerve(s) and/or an associated region (e.g., tissue adjacent to the treatment portion(s) of the target nerve(s)) reaches a desired temperature. In other instances, the energy can be delivered in non-thermal form, and can be converted to thermal energy near the treatment portion of the target nerve(s). For example, energy can be conveyed by a wireless inductive energy transfer mechanism (magnetic fields) that is converted to heat by inductive heating (eddy currents in a conductive material that is part of or thermally coupled to the thermal applicator), or can be conveyed by wired conduction of electrical energy and converted to thermal energy by a resistive heater that is part of or thermally coupled to the thermal applicator.

The desired temperature can be selected using any suitable method. In some instances, the desired temperature can be determined based on one or more parameters such as location of delivery (e.g., distance between the applicator and the treatment portion(s) of the target nerve(s)), nature of intermediary tissue or biological structures between the applicator and the treatment portion(s) of the target nerve(s). In some instances, the desired temperature can be selected using computational fluid dynamic and/or statistical analysis of thermal energy delivery required to achieve a desired thermal modulation of a desired type of nerve fiber, for example, from tests conducted on thermal energy delivery to sample nerve(s). As an example, thermal modulation of certain A-fibers can be achieved at a specified temperature that is different from the temperature required for thermal modulation of C-fibers. For example, in some instances, reversible, thermal blockade of A-fibers can be conducted by delivering thermal energy to achieve a temperature of 50-54° C. for less than 1 minute or a temperature of 46-48° C. for 10-20 minutes followed by cooling. As another example, in some instances, reversible, thermal blockade of C-fibers can be selectively conducted without a blockade of A-fibers by delivering thermal energy to achieve a temperature of less than or equal to about 45° C. Said another way, by never exceeding 45° C. nerve temperature, reversible, thermal blockade in C-fibers can be effectively initiated at a temperature that does not initiate blockade in A-fibers. In some implementations, this method can be used to selectively block pain signal transmission while allowing motor signals to proceed. In some instances, a desired temperature can be selected such that it reduces risk of nerve damage by maintaining motor function activity and/or by increasing chances of a reversible nerve block. In some instances, one or more physiological signals can be recorded from tissue associated with the target nerve(s) (e.g., action potentials evoked in the target nerve(s)) or deduced (e.g., via reduction in perception of pain) and the delivery of thermal energy can be based on the recorded physiological signals or meeting predefined criteria (e.g., decrease in rate of action potentials below a threshold value or reduction of pain to below a certain level).

At 204, the method 200 includes a step to continue to deliver thermal energy to the target nerve(s) via the thermal applicator to maintain temperature of the treatment portion(s) of the target nerve(s) at the desired temperature for a desired time to achieve thermal modulation. In some instances, the continued delivery of thermal energy can be controlled in any suitable manner to achieve the desired thermal modulation. In some instances, the continued delivery of thermal energy to the target nerve(s) can be extended for the desired time based on suitable parameters of delivery including mode of delivery (e.g., delivered via a thermally conducting medium, directed via thermally non-conductive medium, etc.). In some instances, the desired time of delivery of thermal energy can be based on one or more parameters including efficiency and/or rate of transfer of thermal energy using the applicator and/or the delivery method, rate of delivery. In some instances, the desired time of delivery of thermal energy may depend on location of delivery (e.g., distance between the applicator and the treatment portion(s) of the target nerve(s)), nature of intermediary tissue between the applicator and the treatment portion(s) of the target nerve(s), statistical analysis of a time duration of thermal energy delivery required to achieve desired thermal modulation (e.g., from tests conducted on thermal energy delivery to sample nerve(s)) etc. In some instances, the continued delivery of thermal energy can be based on the physiological signals recorded from tissue associated with the target nerve(s) meeting predefined criteria. In some instances, the continued delivery and extent of nerve block (0-100%) can be based on input provided by the user or another participant or an automated learning system or other intra-system or digital input. In some instances, the selection of which type of nerve fibers to selectively or preferentially block may be made based on input received. In some instances, the continued delivery of thermal energy can be based on input provided by the user or another participant. In some instances, the continued delivery of thermal energy can take into consideration a rate of transfer of thermal energy from the source to the target nerve(s) and a rate of change of temperature of the target nerve(s) upon delivery of thermal energy. For example, in some instances the continued delivery of thermal energy can be based on a ramp up period involving gradual change in temperature of the target nerve(s) with delivery of thermal energy. In some instances, the continued delivery of thermal energy for a desired time period can be based on one or more properties of the target nerve(s) and/or associated tissue related to retention of thermal energy. For example, the desired time period of continued delivery of thermal energy can be based on an expected and/or measured rate of dissipation of heat from the treatment portion(s) of the target nerve(s) and/or tissue associated with the treatment portion(s) of the target nerve(s).

At 206, the method 200 incudes a step to cease delivery of thermal energy to the treatment portion(s) of the target nerve(s) via the thermal applicator. In some implementations, the ceasing of delivery of thermal energy can be based on the duration of delivery reaching a predetermined time interval. In some instances, the ceasing of delivery of thermal energy can be based on physiological state of the patient and/or the target nerve(s) of the patient. For example, in some instances the delivery of thermal energy can be ceased based on a feedback (e.g., extent of pain relief) from the patient. In some instances, the delivery of thermal energy can be ceased based on the physiological signals recorded from tissue associated with the target nerve(s) meeting predefined criteria.

The method 200 includes, at 208, an optional step to allow or cause the treatment portion(s) of the target nerve(s) to return to a physiological temperature. In some instances, a baseline temperature associated with the target nerve(s) may be recorded before thermal modulation and stored such that the target nerve(s) can be returned to the baseline temperature.

In some instances, the thermal neural modulation can be targeted to deliver thermal energy, as described above, to effect a reversible, thermal blockade of specific types of nerve fibers by adapting the method 200. At 210, the method 200 includes optionally to allow the treatment portion(s) of target nerve(s) to remain at physiologic temperature for sufficient time for A-fibers to recover from pre-conditioning, but not for sufficient time for C-fibers to recover from pre-conditioning. In some instances, A-fibers can be found to recover from reversible, thermal blockade at a faster rate than C-fibers. In such instances, the desired time that the treatment portion(s) of the target nerve(s) is allowed to remain at physiologic temperature can be based on a desired preferential and/or extended thermal modulation of C-fibers over A-fibers.

At 212, the method 200 includes an optional step to withdraw thermal energy from the treatment portion(s) of target nerve(s) (i.e., cooling the target nerve(s)) via a thermal applicator, which may or may not be the same thermal applicator that is used to deliver thermal energy, to decrease the temperature of target nerve(s) to a desired temperature below physiologic temperature. In some embodiments, the withdrawal of thermal energy can be carried out in a passive manner. For example, thermal energy can be passively withdrawn from the target nerve(s) by placing the target nerve(s) under conditions conducive to heat dissipation and/or dissipation of thermal energy in order to reach a thermal equilibrium at a lower temperature. In some instances, the withdrawal of thermal energy can be carried out actively by drawing or extracting thermal energy from the target nerve(s) by using a thermal sink as described herein. In some instances, the withdrawal of thermal energy can be via a combination of active and passive methods.

In some instances, the withdrawal of thermal energy can be via a thermal applicator disposed in operative relationship with the treatment portion of the target nerve(s) as described above. The withdrawal of thermal energy can be using any suitable method of transfer of thermal energy. In some instances, the withdrawal of thermal energy can be from the target nerve(s) and to a sink of thermal energy. The sink of thermal energy can be any suitable element at a temperature lower than the physiologic temperature such that the sink absorbs the thermal energy extracted from the target nerve(s). In some instances, the sink of thermal energy can be an element that can be maintained at a suitable temperature (e.g., heated and/or cooled) in a controlled manner to withdraw the thermal energy from the treatment portion(s) of the target nerve(s) and to decrease the temperature of the treatment portion(s) of the target nerve(s) to a desired temperature lower than the physiologic temperature. In some instances, thermal energy can be directed from the target nerve(s) to the sink via a thermal energy conduit. In some instances, the withdrawal of thermal energy can be via a thermally conductive medium. In some instances, the thermal applicator to remove thermal energy may include a coolant tube, a thermoelectric cooler, a refrigeration system, a Peltier cooler, ice or any other suitable cooling means capable of providing the desired temperatures and durations.

In some instances, the withdrawal of thermal energy can be conducted at a controlled rate (e.g., rate of heat transfer) for a controlled period of time such that the treatment portion(s) of the target nerve(s) and/or an associated region (e.g., tissue adjacent to the treatment portion(s) of the target nerve(s) reaches a desired temperature lower than the physiologic temperature. The desired temperature can be selected using any suitable method. In some instances, the desired temperature can be determined based on one or more parameters such as location of delivery (e.g., distance between the applicator and the treatment portion(s) of the target nerve(s)), nature of intermediary tissue between the applicator and the treatment portion(s) of the target nerve(s). In some instances, the desired temperature can be selected using statistical analysis of thermal energy delivery required to achieve a desired thermal modulation of a desired type of nerve fiber, for example, from tests conducted on thermal energy delivery to sample nerve(s).

At 214, the method 200 optionally incudes continued withdrawal of thermal energy from the treatment portion(s) of the target nerve(s) via the thermal applicator to maintain the temperature of target nerve(s) at the desired temperature for a desired time to achieve desired thermal modulation.

In some instances, the continued withdrawal of thermal energy can take into consideration a rate of transfer of thermal energy and/or a rate of change of temperature of the target nerve(s) upon cessation of delivery of thermal energy. For example, in some instances the continued withdrawal of thermal energy can be based on a ramp down period and ramp down rate involving gradual change in temperature of the target nerve(s) with cessation of delivery of thermal energy and/or withdrawal of thermal energy. The rate of ramp down can be different from a rate of ramp up of temperature of the target nerve(s) and or associated tissue. For example, the ramp up rate of increase in temperature of an example target nerve and/or tissue adjacent to the target nerve can be higher or lower than the rate of ramp down of temperature.

In some instances, the continued withdrawal of thermal energy can take into consideration a second ramp up rate associated with the target nerve(s) and/or the associated tissue, the first ramp up rate being a rate of heating and the second ramp up rate being a rate of cooling. The first ramp up rate (e.g., rate of heating) and the second ramp up rate (e.g., rate of cooling) can each have a corresponding first and second ramp down rate associated with the rate at which the target nerve(s) and/or the associated tissue returns to a physiologic temperature following the delivery of thermal energy (e.g., heating) and the withdrawal of thermal energy (e.g., cooling), respectively.

In some instances, the continued withdrawal of thermal energy for a desired time period can be based on one or more properties of the target nerve(s) and/or associated tissue related to retention of thermal energy. For example, the desired time period of continued delivery of thermal energy can be based on an expected and/or measured rate of dissipation of heat from the treatment portion(s) of the target nerve(s) and/or tissue associated with the treatment portion(s) of the target nerve(s).

At 216, the method 200 optionally includes ceasing the withdrawal of thermal energy from treatment portion(s) of target nerve(s) via the thermal applicator. In some instances, the ceasing of withdrawal of thermal energy can be based on receiving a feedback signal (e.g., via a temperature sensor) indicating the temperature of the treatment portion(s) of the target nerve(s) to have reached a threshold value. In some instances, the ceasing of withdrawal of thermal energy can be based on a lapse of a predefined time period. In other instances, the ceasing of withdrawal of thermal energy can be based on input provided by the user or physiologic measurements or other participants or digital systems. Withdrawal of thermal energy may optionally be followed by delivery of thermal energy to the treatment portion(s) of target nerve(s) and continued cyclic thermal modulation by repeated warming and cooling.

At 220, the method 200 optionally includes allowing the treatment portion(s) of target nerve(s) to return to a physiologic temperature. In some instances, the allowing to return to a physiologic temperature can be based on parameters including ambient temperature, health indicators of the patient (e.g., heart rate, breathing), demographic information associated with each patient (e.g., age, species, genetics, etc.).

The moderate heating and/or moderate cooling of treatment portions of nerves required to achieve the desired thermal modulation described above can be achieved by a variety of techniques and apparatus. One embodiment of a thermal neural modulation system is shown schematically in FIG. 1. Thermal neural modulation system 100 includes a thermal energy sink and/or source ("TESS") 110, a thermal applicator 170, and a controller 180. System 100 may also include one or more feedback sensors 190. TESS 110 may receive thermal energy from and/or provide thermal energy to, respectively, a thermal applicator 170. Optionally, energy may be transferred between TESS 110 and thermal applicator 170 by an energy conduit 150. The operation of system 100 may be controlled by controller 180, which may be, for example, operatively coupled to TESS 110 and/or energy conduit 150. The control of system 100 by controller 180 may be based in part on signals received from one or more feedback sensor(s) 190, TESS 110 and/or energy conduit 150.

Some or all of the components of system 100, e.g. TESS 110, thermal applicator 170, controller 180, optional energy conduit 150, and/or sensor(s) 190, may be implanted in the body of the patient or may be external to the patient.

System 100 may thermally modulate a nerve N by raising or lowering the temperature of a portion of the nerve N, directly or by raising or lower the temperature of adjacent tissue T and/or thermally conductive material TCM (described in more detail below) by delivering thermal energy to, or receiving thermal energy from, nerve N and/or tissue T and/or thermally conductive material TCM with thermal applicator 170. Thus, thermal applicator 170 may be in direct contact with nerve N, i.e. may be implanted in the body of the patient. Alternatively, thermal applicator 170 may be separated from nerve N by some amount of tissue T, and/or by some amount of thermally conductive material TCM. In that case, thermal applicator 170 may be implanted in the body of the patient, i.e. in tissue T and/or in thermally conductive material TCM near nerve N tissue. Alternatively, thermal applicator 170 may be external to the patient in contact with tissue T (e.g. in contact with the skin of the patient) directly and/or through thermally conductive material TCM. Optionally, a thermally insulating material TIM (described in more detail below) may be interposed between some portion of thermal applicator 170, thermally conductive material TCM, tissue T, and/or nerve N.

The TCM can be any suitable thermally conductive material located between the thermal applicator 170 and target tissue T or nerve N. In some instances, the TCM can be a conductive gel or solid configured to aid in transfer of thermal energy. The TCM may be used to cushion the nerve within the thermal applicator 170 and may promote thermal energy transfer from the thermal applicator 170 to the nerve N. The TCM may further act to maintain a low level of temperature variance throughout the targeted portion of a nerve. Higher thermal conductivities of the TCM may result in more efficient thermal energy transfer from the thermal applicator 170. The TCM may be biocompatible for implantation at or near a nerve. Other thermally conductive materials may be contemplated for use under various implementations based on dimensions of target tissue, target nerve, and/or characteristics of thermal energy transfer desired, among other parameters.

The TIM can be made of any suitable material to be thermally insulating and biocompatible For example the TIM may be solid, liquid, gel, or foam. In some embodiments, the TIM can be implemented as an insulation backing that conforms to the features of the thermal applicator 170 and is insulating with a low thermal conductivity. The TIM may be configured with respect to the thermal applicator 170 and may conform to features, such as a fluid channel that may be defined in the thermal applicator 170, and reduce the loss of thermal energy from the thermal applicator 170.

In some implementations, the TIM or portions of the TIM may be injected in a roughly spherical shape around the targeted section of nerve and thermal applicator 170 and may involve one or more injections to apply it to the desired location. In some embodiments, the TIM may be injected in a sphere with approximately a 10 mm diameter. The TIM can have a viscosity that is low enough to allow for injection to the site but high enough to prevent it from leaving the target area after installation for some amount of time. An example TIM may be a self-setting material that is injected as a liquid and then undergoes a chemical reaction to solidify and set up to maintain its shape and location, such as CryoLife's BioFoam Surgical Matrix. In some embodiments, the TIM may be polyurethane foam with a low thermal conductivity of about 0.027 W/mK. The TIM may thus prevent the spread of thermal energy over an area than it would otherwise be spread, which may allow more targeted use of thermal modulation or use of thermal modulation near an area where it is undesirable to thermally modulate.

The containment of thermal energy using TIM may be useful in locations such as specifically targeting nerves in a joint that are causing discomfort without affecting nerves that control motion or sensation that are not causing pain. Thermally insulating gels, foams, or other carrier materials can be made by combining a base polymer with a thermally insulating filler. Base polymers may include hydrogels and silicones, including gels that may be injected at room temperature and that set to their final shape in situ at body temperature. Fillers may include polyurethane foams, polystyrene, glass fibers, and aerogels, as are commonly used to create thermally insulating polymers with thermal conductivities in the range of 0.1-0.01 W/mK, such as polystyrene, Cabot's aerogel, and General Plastics' polyurethane foam.

As described herein, thermal modulation of a nerve N can be guided by a predetermined temperature at which a portion of the nerve N is desired to be maintained for a defined period of time. In some implementations, the thermal applicator 170 may have to be set to a different temperature than the temperature that a portion of the nerve N is to be raised to in order to account for undesired loss and/or dissipation of thermal energy. For example, in some instances when the nerve N is to be heated by delivery of thermal energy via the thermal applicator 170, the first temperature to which the thermal applicator 170 is to be raised may be lower than the second temperature to which the nerve N is to be heated. As another example, in some instances when the nerve N is to be cooled by withdrawal of thermal energy via the thermal applicator 170, the first temperature to which the thermal applicator 170 is to be cooled may be higher than the second temperature to which the nerve N is to be cooled.

As described above, in some implementations, the thermal applicator 170 may be placed at any suitable location and/or with any suitable separation from the nerve N (e.g., a treatment portion of the nerve N). In some such implementations, a thermal gradient may be established between the first temperature of the thermal applicator 170 and the second temperature of the nerve N. The thermal gradient may be defined by a first temperature at which the thermal applicator 170 is to be set in order to achieve a desired second temperature at the nerve N. The thermal gradient may be established across intervening portions between the thermal applicator and the nerve N, such as for example, a TCM, tissue T, etc. The thermal gradient can be of any suitable form depending on the thermal conducting/insulating properties of the media lying between the thermal applicator 170 and the nerve N (e.g., TCM, tissue, etc.).

The thermal gradient, the first temperature of the thermal applicator and/or the second temperature may be determined based on parameters including the degree of separation or distance between the thermal applicator 170 and the nerve N and/or the mode of delivery or withdrawal of thermal energy. In some instances, the thermal gradient and/or the first temperature of the thermal applicator 170 can be determined and/or implemented based on the desired second temperature of the nerve N. In some embodiments, the system 100 can include pre-set temperature limits within which the thermal applicator 170 can be operated. Thus, the first temperature of the thermal applicator 170 can be partially based on the preset limits. In some instances, the first temperature of the thermal applicator 170 can be set taking into account the TCM. In some instances, the thermal gradient can be implemented at least partially via the TCM and/or tissue T such that thermal energy is delivered to and/or received from the nerve N via the tissue T and/or thermally conductive material TCM.

The range of temperatures over which the thermal gradient extends may increase with increasing distance between the thermal applicator 170 and the nerve N. In some implementations, for example, the thermal applicator 170 can be implanted in direct contact or in proximal juxtaposition with the nerve N such that there is minimal physical separation between the nerve N and the thermal applicator 170. Under such implementations, a thermal gradient may be established between the thermal applicator 170 and the nerve N over a small range of temperatures and over a small physical distance. In some implementations, the thermal applicator 170 can be placed at a greater separation from the nerve N (e.g., external to the patient and in contact with the skin of a patient) such that there is considerable physical separation between the nerve N and the thermal applicator 170.

Figures 3A, 3B:
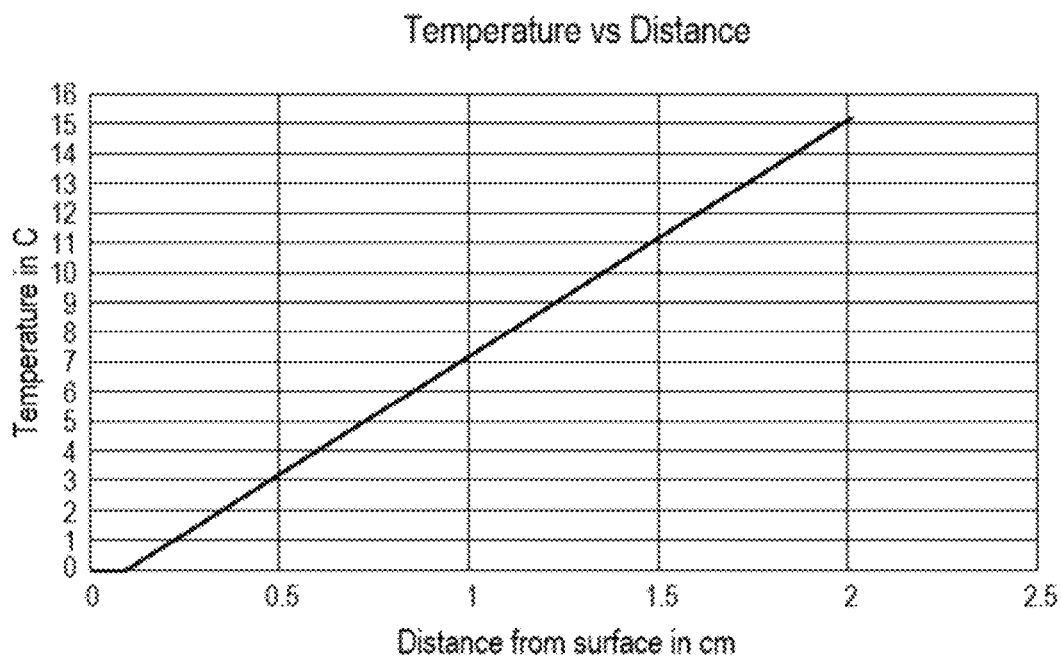
FIG. 3A is a graph illustrating the change in tissue temperature as a function of depth within the tissue upon application of moderate cooling.
FIG. 3B is a table illustrating the change in tissue temperature as a function of depth within the tissue upon application of moderate heating.

FIG. 3A shows an illustration of an example thermal gradient between a portion of tissue adjacent to a thermal applicator (e.g., skin surface) and a target nerve. In the example shown in FIG. 3A, the temperature of the target nerve is shown at different distances from a 0° C. cold element. The target nerve is expected to be about 15° C. at a distance of 2 cm from the 0° C. cold element. In some instances, occipital scalp thickness including skin and underlying soft tissues may be less than 3 mm or more than 7 mm thick. To achieve target nerve temperatures in the range of 10-55° C. including 15-45° C., skin surface temperatures in the range of −5-55° C. when held for less than or about 5 minutes or more than 90 minutes may be required to achieve the target nerve block or modulation temperature. The temperatures and durations are a function of individual patient factors including thickness of the scalp, and skin and nerve sensitivity to temperature.

In some instances, an initiation phase followed by a thermal modulation phase could be implemented including a sequence of increasing and/or decreasing temperatures (e.g., 42-45° C., 0° C., 44-48° C., 8° C., etc.) each maintained for a specific period of time (e.g., 90 min period, 60 min period, 30 min period, 20 min period, 10 min period, etc.) in specific configuration (e.g., thermal modulation delivered via an occipital pad placed on hair/skin or any other place on the body), possibly including use of a thermally conductive gel between the pad and the skin. The initiation phase and/or the thermal modulation phase can include any number of cycles (e.g., a warm cycle including a protocol of sequence of warm temperature, a cold cycle including a protocol of sequence of cold temperature) in any suitable order. The specific sequence of temperatures, time period of delivery and/or maintenance of a temperature, the configuration and/or mode of delivery, number of cycles, order of cycles, and other related parameters of a protocol of thermal modulation may be set and/or modified based on statistical and/or mathematical and/or computational fluid dynamics modeling of thermal modulation as well as based on user input regarding for instance the extent of nerve block or a desired change in temperature or time held at a given temperature. In some instances, based on modeling and/or other empirical results, patients may be advised to apply therapy on a recommended schedule. For example, patients may be advised to use therapy daily (e.g., once at night or in the morning, 1-4 warm/cool cycles per treatment) or twice a day (e.g., 1-4 warm/cool cycles in the morning and 1-4 cycles at night, or as needed), or more often including up to full-time-use 24 hours per day, or less often such as every-other day or less frequently as the cumulative benefits of room-temperature nerve block may be realized.

In some instances, the relationship between a desired temperature of the nerve N and the temperature of the thermal applicator 170 can be understood using experimental and simulation studies of thermal modulation using a set of experimental and/or simulated thermal systems and anatomical systems. For example, experimental studies can be conducted using sample tissue (e.g., tissue T) including a sample nerve (e.g., nerve N), and a sample thermal modulation system, with known placement and/or separation of a sample thermal applicator (e.g., thermal applicator 170) and a portion of the sample nerve. The sample tissue, sample nerve and/or the sample thermal applicator can be coupled to temperature sensors to record temperature levels associated with each. During an experimental study, the sample thermal modulation system can be operated over various regimes such that the sample thermal applicator can be set to a variety of temperatures and the resulting temperature in the sample tissue and the sample nerve can be recorded. In some instances, statistical analysis of several such experimental studies can be conducted to guide the operation of thermal modulation system 100.

In some instances, the operation of a sample thermal modulation system can be simulated to obtain results regarding expected performance of the system 100. Simulation models of thermal modulation systems can be constructed using thermal data related to sample specifications of thermal modulation systems. The simulation models can be tested for operation in simulated environments of use constructed using anatomical data associated with the expected environments for specific use cases. For example, thermal modulation systems used for treating conditions associated with occipital nerves (e.g., least, greater and lesser occipital nerves), can be simulated using simulation models of thermal modulating systems for administering therapy (e.g., based on thermal data obtained from experimental studies) in combination with models of user anatomy built using anatomical data (e.g., scalp thickness, gender, age, weight, BMI, etc.) In some instances, simulations can be used to calibrate components of a thermal modulation system, select components for a thermal modulation system (based on specifications and interaction of modelled components), and/or set system parameters (e.g., required fluid pump, heater, cooler (e.g. thermoelectric cooler TEC), heatsink, and fan parameters for use of a thermal modulation system. Simulations can also be used to confirm operation dynamics of systems.

FIGS. 3A-3B illustrate the effects of distance on heating and cooling of tissue, and target nerves disposed within the tissue, obtained using simulations. In FIG. 3A, a cooling step requiring a target nerve to be cooled to about 15° C. at a distance of 2 cm is demonstrated using a simulation. In the simulation, it was determined that chilling fluid may provide a temperature of 0° C. to the skin of a patient at a target location (corresponding to a treatment portion of a target nerve) for about 10 minutes to effect a 15° C. temperature for the target portion of a target nerve within 8 mm of the surface of the skin, while chilling fluid may provide a temperature of 0° C. to the skin of a patient at a target location for about 20 to about 30 minutes to effect a 15° C. temperature for a treatment portion of a target nerve within 20 mm of the surface of the skin. Beyond a depth of about 20-25 mm from the surface of the skin, complete nerve block may not be attainable as it may be impractical to externally cool a nerve to the desired temperature without causing discomfort or intolerability for a patient and may require extraneous energy to produce. It was determined that, once a 15° C. nerve cooled temperature is achieved, it may be possible to maintain the 15° C. cooled temperature at the treatment portion of the target nerve with a chilling fluid at the skin surface of a patient with a temperature ranging from about 8° C. to about 10° C.

In FIG. 3B, a, resistively heated element is heated to 45° C. at a depth of 20 mm within tissue, and the temperature of the tissue is monitored at varying distances from the resistively heated implanted element. While the surface of the resistively heated implant remains at 45° C. (distance of 0 mm), the temperature of the tissue decreases by several degrees with distance.

Figure 3C:
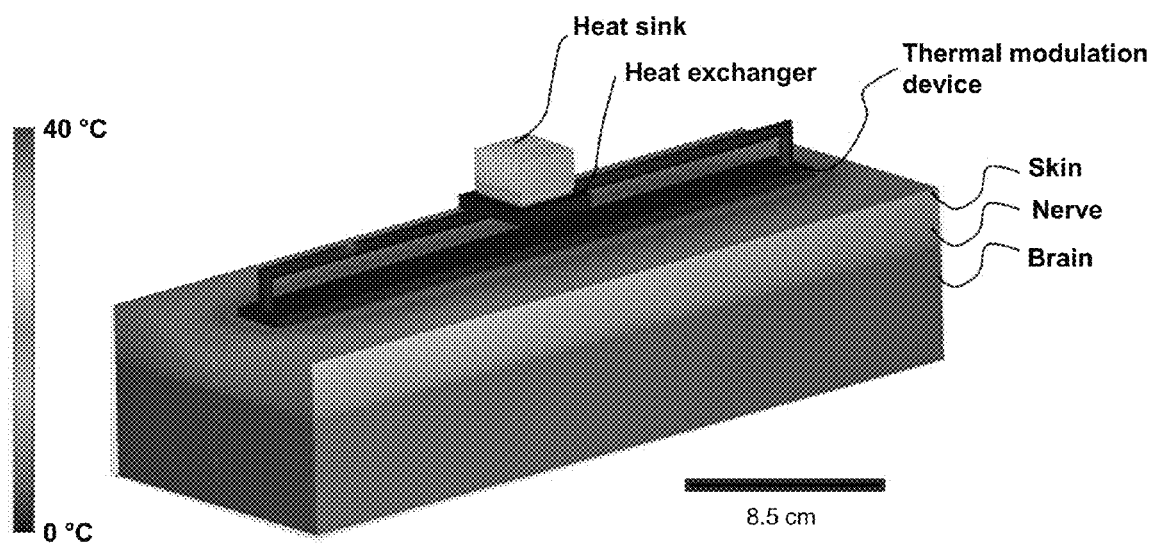
FIGS. 3C-3D are example results from simulations of thermal modulation applied to modelled tissue using a simulated thermal modulation system, according to an embodiment.
Figure 3D:
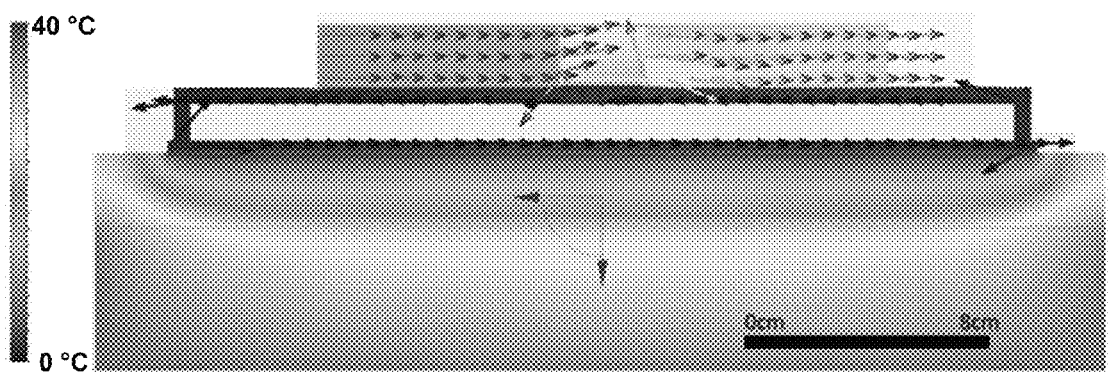

As an example, model simulations can include isothermal and kinetic simulations to assess temperature as a function of depth through tissue layers. Example outputs of simulations of thermal modulation systems and sample environments of use are shown in FIGS. 3C and 3D. The example outputs in FIGS. 3C and 3D depict the equilibrium (steady state) system and tissue temperatures resulting from 0° C. on the skin surface. In this simulation the circulating fluid (e.g., water) was modeled to be heated and cooled by a thermoelectric cooler (TEC) (e.g., model 12711-9L31-05CL from Custom Thermoelectronics) that pumps the fluid (e.g., water) to a skin-surface contact pad. The TEC and external heater/cooler/pump/power unit was modeled to be raised from the skin surface as shown in FIG. 3C. Modeling the TEC to cool the circulating water was found to generate significant heat on the contact side of the TEC that was dissipated through the heatsink (e.g., fins) shown on the top of the modeled arrangement.

In some embodiments, the thermal modulation system 100 may include a feedback sensor 190 for monitoring the biological signals such as temperature associated with the thermal applicator 170, ambient temperature, temperature of a tissue (e.g., skin) of a patient, pressure, and chemical levels on or near a nerve. In some embodiments, feedback sensor 190 is a temperature sensor, such as a thermocouple, a thermistor or any other suitable device or material capable of monitoring the changes in temperature of a nerve before, during, and after thermal modulation to block or partially block the nerve. The feedback sensor may be placed in or near the vicinity of the at least one heat source/sink or thermal applicator, or at other locations in or on the body or elsewhere within the device. In some embodiments, an optional at least one echogenic guide or other such suitable guiding material or device is located within an implantable portion of a system 100 to aid in placement of the thermal applicator 170.

In some embodiments, a thermal energy system may comprise a feedback sensor for monitoring the biological signals selected from a group consisting of body temperature, blood pressure, heart rate, time, perspiration, oxygen saturation, electrocardiogram signal, nerve conduction signal or any other such useful and suitable parameter of a patient's health, symptoms, or comfort. The thermal modulation system 100 may be capable of communicating the parameters detected by the feedback sensor 190 with the system controller 180.

In some embodiments, a user may control communication with the system controller 180 via one or more user feedback sensors 190 (e.g., a dial, knob, button, user interactive panel, and/or the like) wherein a user may select input factors from a group consisting of pain level, extent of motor function, sensory sensitivity including pain, touch, sharpness, temperature, and stress level. The user may also control the system by turning it "on" or "off" or by varying the operation at any level or for any duration. In other embodiments, the user feedback sensors 190 may also be implemented in software, such as an application running on a compute device such as a smart phone or tablet, and the user feedback sensor 190 can provide feedback to the controller via wirelessly, e.g. via communicator 186, as discussed in more detail below.

In some embodiments, the thermal modulation system may provide information to assist in the acceptable placement of the thermal modulation system. In some embodiments, the thermal modulation system 100 may provide information to assist in the acceptable placement of the thermal energy system 100 or a portion of the system 100

(e.g., the thermal applicator 170) based on the relative location of two or more portions of the system. In some embodiments, the thermal energy system 100 may determine the acceptable placement of the thermal energy system 100 based on effects on a patient selected from a group comprising sensation, organ function, pain level, extent of motor function, temperature, sharpness, blood pressure, time, flow rate, heart rate, perspiration, stress level, or any other such useful and suitable parameter of a patient's health, symptoms, or comfort. In some embodiments, the placement of the system 100) may be further guided by user input factors from a group consisting of pain level, extent of motor function, sensory sensitivity including pain touch, sharpness, temperature, and stress level. In some embodiments, a feedback loop may be utilized to control power delivered to the system 100 based on temperatures detected by the feedback sensor 190.

TESS 110 in system 100 can be implemented in many different ways, as a source of thermal energy and/or as a sink for thermal energy.

As a source of thermal energy to be delivered to thermal applicator 170, TESS 110 can generate the thermal energy through a variety of approaches. One approach involves direct conversion of electrical energy to thermal energy. For example, TESS 110 can generate thermal energy by passing electric current through an electrical resistance, i.e. by resistive heating. Electrical heating can also be produced by induction heating, e.g. by passing alternating electric current through an electromagnet to produce alternating magnetic fields that produce eddy currents in a conductor, heating the conductor by Joule heating. TESS 110 can also be implemented with one of more techniques for using electromagnetic radiation to transfer heat energy to thermal applicator 170, or to use thermal applicator 170 as the delivery device for the electromagnetic radiation. For example, tissue can be heated with electromagnetic radiation in the microwave, radio frequency (RF), and/or infrared (IR) portions of the frequency spectrum. Ultrasound may also be used to heat tissue. As another example, electrical heating/cooling can be produced by generating an electrical potential by passing electrical current across a thermoelectric material to generate a temperature differential. Using the temperature differential TESS 110 can also be implemented as a heat pump, to transfer thermal energy from a source and deliver it to thermal applicator 170. One implementation of a heat pump is a thermoelectric cooler (TEC) or Peltier device, i.e. a solid-state heat pump, in which passage of a DC electric current through the device moves thermal energy from one side of the device to the other. Some implementations of such a system can be similar to the device available from Embr Labs, for delivering/receiving thermal energy using thermoelectric material via the Peltier effect. Implementations of such a device are described in U.S Patent Publication No. 2018/0042761, incorporated by reference in its entirety herein. The source of thermal energy can be implemented in any suitable manner. For example, the source of thermal energy can be heated fluid, ambient air, a portion of a body of a patient that is at a higher temperature than another portion, etc. Another implementation of a heat pump is a vapor compression refrigeration system, which circulates a refrigerant through a compressor, condenser, expansion valve, and evaporator. Some implementations of such a thermal modulation system can be similar to the vapor-compression refrigeration systems available from Aspen Systems. Some such implementations of a system delivering/receiving thermal energy using vapor compression refrigeration systems are described in U.S. Pat. No. 7,789, 202, incorporated by reference in its entirety herein.

TESS 110 can also be implemented by conversion of chemical energy to thermal energy, such as an oxidation reaction (e.g. air-activated, iron-based chemistry used in hand warmers), a crystalline phase change reaction (e.g. sodium acetate), or a combustion reaction (e.g. charcoal or lighter fluid). TESS 110 can also be implemented with a reservoir of material (gas, liquid, or solid) with a relatively high specific heat that is at a suitable temperature above the desired temperature for the nerve. For example, a reservoir of hot water can be used as the source of thermal energy.

As a sink for thermal energy to be received from thermal applicator 170, TESS 110 can receive the thermal energy through a variety of approaches. TESS 110 can be implemented as a heat pump, to transfer thermal energy from thermal applicator 170 and deliver it to a suitable heat sink. The same heat pump approaches described above for the TESS 110 as a source of thermal energy can be used, e.g. Peltier device and/or vapor compression refrigeration cycle. The heat pump used for cooling can be different from the heat pump used for heating. Optionally, with such heat pump implementations, the heat pump can be reversible so that it can operate alternatively to deliver thermal energy to, and receive thermal energy from, thermal applicator 170. Similarly, TESS 110 can also be implemented by conversion of thermal energy to chemical energy, such as the reverse of the crystalline phase change reaction described above. TESS 110 can also be implemented with a reservoir of material (gas, liquid, or solid) with a relatively high specific heat that is at a suitable temperature below the desired temperature for the nerve. For example, a reservoir of cold water (including a mixture of water and ice) can be used as the sink for thermal energy. Any other suitable substance that can retain a cold temperature (e.g., dry ice) can be suitably used as a sink.

In some implementations, the exchange of thermal energy between TESS 110 and the nerve N, or between the nerve and/or TESS 110 and the ambient environment, can be via pumping fluid (e.g., air, water, etc.) that may act as an agent to transfer the thermal energy. The system 100 may implement fluid movers to move the fluid to transfer the heat. For example, the system 100 may implement fluid movers or flow controllers such as fans (e.g., to flow air across heat exchangers), pumps (e.g., to flow fluid past TESS 110 and the thermal applicator 170), valves (e.g., to direct the flow of fluid), etc.

TESS 110 may function only to deliver thermal energy to thermal applicator 170, may function only to receive thermal energy from thermal applicator 170, or may function both to deliver and to receive thermal energy. Although shown in FIG. 1 as having a single TESS 110, thermal neural modulation system 100 may have more than one TESS 110. For example, system 100 may have one TESS 110 to deliver thermal energy and another TESS 110 to receive thermal energy, both for application to the same treatment area. In another example, system 100 may have a separate TESS 110 to treat each of two or more treatment areas. In some implementations, TESS 110 can include a network of interconnected sink(s) and source(s) each accessible and available to a network of heat pumps and/or thermal applicators 170 via a network of thermal conduits TC to deliver thermal modulation to multiple treatment areas or an expansive treatment area.

Depending on the approach used to provide or receive thermal energy, TESS 110 may require a source of power. For example, if TESS 110 provides thermal energy by resistive heating, or if it provides or receives thermal energy by a Peltier device, it will require a source of electrical energy. Such electrical energy source may be incorporated into, or part of, TESS 110, or may be separate from but coupled to TESS 110, and still be part of system 100, such as a primary or secondary battery, or capacitor. Alternatively, the electrical energy source may be separate from TESS 110 and system 100, but TESS 110 and/or system 100 may be have interface to receive electrical energy from the source. Such sources may include DC or AC power (e.g. from a household electric source) with a direct connection, or an indirect connection such as inductive coupling, microwave transfer, laser power transfer, etc.

Thermal applicator 170 in system 100 can also be implemented in many different ways appropriate to the corresponding implementation of the system 100. For example, thermal applicator 170 can be implemented based on the distance between the placement of the applicator and the target nerve N and the nature of the tissue and/or other material lying between the thermal applicator 170 and the target nerve. The thermal applicator 170 can be of any suitable shape depending on the target anatomy and implementation. For example, in some implementations the thermal applicator 170 can be a pad to interface with a portion of a patient's body. The thermal applicator 170 can be modeled to conform to a suitable shape (e.g., to interface with a surface of a patient's body) to receive thermal energy from the TESS 110 and deliver the thermal energy to the target nerve N or vice versa. In some implementations, the thermal applicator 170 can be implantable and constructed in any suitable shape including the shape of a thin strip, horseshoe, a C-shape, a U-shape, a bowl, a butterfly, a horseshoe and/or a semi-circle, to interface with the target nerve N and/or tissue adjacent to a treatment portion of the target nerve N (e.g., the thermal applicator can be U-shaped and it can extend around a portion of the nerve N or the opening of the U can be aimed in the direction of the nerve N). The thermal applicator 170 can be implanted at or near the target nerve N to provide heating and/or cooling by receiving and/or delivering thermal energy from and/or to the TESS 110, such that the nerve may experience reversible blockade.

Figures 17A, 17B:
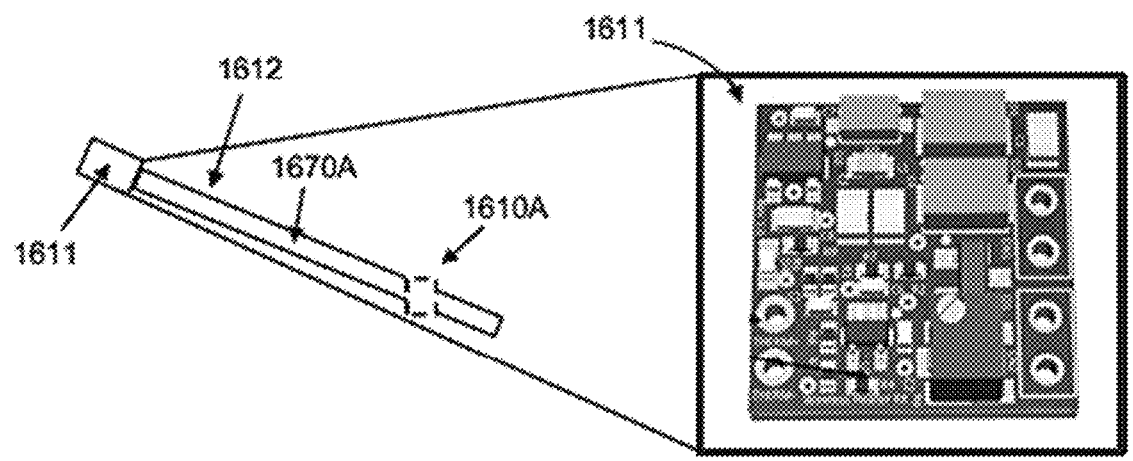
FIGS. 17A-C are illustrations of a hybrid wearable and implanted implementation of a thermal neural modulation system, according to an embodiment.
Figure 17C:
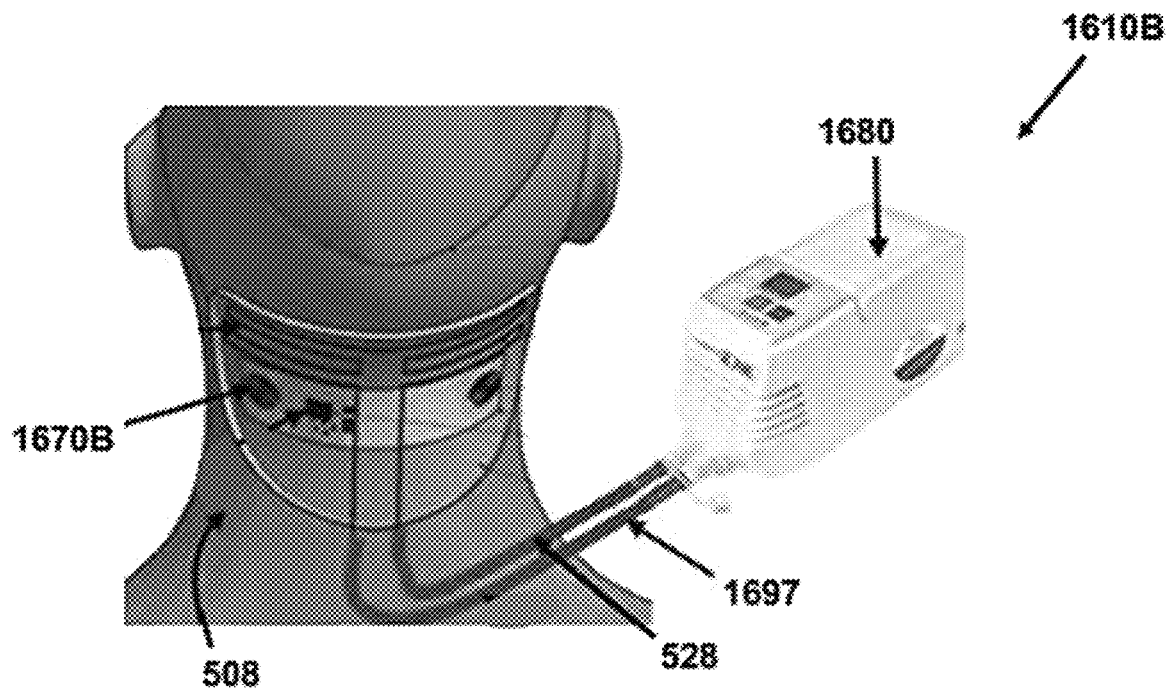

In some implementations, the thermal applicator 170 can be implanted at or near the target nerve N to provide heating by directly receiving thermal energy or by receiving non-thermal energy that is converted to heat by the thermal applicator. For example, as depicted in FIGS. 17A-C, a minimally-invasive wireless heating element 1612 can be inserted at ~C2 near the top of the neck and/or between the ears across the occipital nerves. An externally worn headband 508 can inductively power the implanted heating element to provide heating near the nerve, and the external headband can also cool the scalp with cold water pumped from a small external cooling system through a fluid path within the headband. The headband can contain a microprocessor that controls inductive power transfer coils that power the implanted heating element. The wireless heating system provides precisely-controlled heat to the occipital nerves without limitations related to skin sensitivity to temperature or scalp thickness. Thermistors can be embedded in the implant to provide feedback to ensure sufficient cooling reaches the nerve during cool cycles. Alternately, in another implementation, the implanted heating element may be used without external cooling.

The thermal applicator 170 can be made of any suitable size. For example, in some implementations, the thermal applicator 170 to be used as an interface on a surface of a patient's body can be made to have a desired surface area (e.g., defining an area of contact of a square inch) suited for efficient transfer of thermal energy between the TESS 110 and the body of the patient. In some implementations, the thermal applicator 170 to be implanted proximal to a treatment portion of the target nerve N can be sized such that it scales with the diameter of the nerve, such that the thermal applicator 170 may extend around the nerve or extend a particular distance along the nerve, as desired for reversible blockade of the nerve. In some embodiments, for example, a U-shaped thermal applicator 170 can surround a nerve or neurovascular bundle on three out of four sides from a planar on-axis view.

The thermal applicator 170 can be made with any suitable material that is thermally conductive and biocompatible when placed on a surface and/or when implanted at or near a nerve N (e.g., silver, gold, stainless steel, and/or the like). Alternately the thermal applicator 170 can be made with any suitable material that is sufficiently thin in the desired direction of thermal energy flow that it does not significantly absorb thermal energy. The thermal applicator 170 may be produced by 3D printing, injection molding, commercial casting processes, or any other suitable production technique.

In some implementations, the thermal applicator 170 can include portions made of thermally insulating material configured to direct flow of thermal energy along a predetermined path. For example, thermally conductive portions and thermally insulating portions can be used to direct thermal energy to flow preferentially to a particular portion of tissue and/or the target nerve N. Optionally, the thermal applicator 170 can be used to transfer thermal energy via an energy conduit, as described herein.

Optional energy conduit ("TC") 150 can also be implemented in many different ways, appropriate to the corresponding implementations of TESS 110 and thermal applicator 170, to provide a path for energy to move between TESS 110 and thermal applicator 170, in a single direction or bi-directionally (depending on whether the particular implementation of TESS 110 is as a source, sink, or both source and sink for thermal energy). In some implementations, TC can be conductive, convective, forced convective, via fluid tubing, via heat pipe, via directed flow of air, passive distribution from one medium to another or within a medium, and/or a combination of approaches. In some implementations, TC can be wireless inductive energy transfer that is converted to heat by the receiving thermal applicator 170. In other implementations, TC can be wired conductive electrical energy transfer that is converted to heat by resistive heating by the receiving thermal applicator 170. In one approach to transferring thermal energy. TC 150 can rely on the mechanism of conduction. For example, TC 150 can be simply a highly thermally conductive material (e.g. metal) disposed between TESS 110 and thermal applicator 170. Rather than a solid material, TC can be a thermally conductive liquid. In another approach, TC 150 can rely on fluid transport to transfer thermal energy. For example, a liquid heated at an interface (e.g. a heat exchanger) at TESS 110 can be conveyed through a tube or pipe to thermal applicator 170 and transfer thermal energy at an interface (e.g. another heat exchanger) at thermal applicator 170. Cooled liquid can be returned through a separate tube or pipe to TESS 110 to be reheated. The tubing can be formed of any material suitable for conveying the fluid. The tubing at the heat exchanger associated with the thermal applicator 170 may be thermally conductive (e.g., gold, aluminium or copper), whereas the tubing in other portions of TC 150 may be relatively non-conductive (e.g. polymer), and may optionally be covered with a separate insulating material to further reduce thermal energy transfer between the fluid in the tubing and the environment. The tubing can be of any suitable size, shape or form. For example, in some implementations the tubing can be of a suitably narrow or broad area of cross section and follow a serpentine or other suitably convoluted path to increase a surface area of contact between the fluid path and a heat exchanger or TESS 110.

In some implementations, TC 150 can be implemented to allow rapid switching between heating and cooling. In some implementations, a TESS 110 can be implemented such that the same device can be used as a source and a sink alternatively (e.g., a Peltier device used as a heat pump). In some instances, optionally the system 100 can be safeguarded from being switched rapidly. For example, an electrical control may be placed to prevent instant switching of polarity to prevent the devices from being shocked by rapid and dramatic swings in temperature. In some implementations, rapid switching between heating and cooling may be desired and can be accomplished via using a separate sink and source. For example, in some implementations, TESS 110 can include a source and a sink (e.g., a resistive heating element can be used for heating of a working fluid and an ice-water reservoir can be used for cooling, optionally controlled by a valve such as a solenoid valve: the flow diagram in FIG. 37 describes one possible implementation of this example). The TC 150 can be configured using one or more flow controllers and/or fluid movers to allow conductive liquid to be conveyed via either the source (for heating) or the sink (for cooling). The system 100 can initially be used at a first configuration (e.g., to heat a portion of a target nerve N). In the first configuration, the system 100 can activate one or more flow controllers and/or fluid movers to convey thermally conductive fluid to the thermal applicator 170 via a path including a heating interface (e.g., heat exchanger associated with the source portion of the TESS 110). When the system is to be rapidly switched from the first configuration (e.g., of heating) to a second configuration (e.g., of cooling), the system 100 can activate one or more flow controllers and/or fluid movers to convey thermally conductive fluid to the thermal applicator 170 via a different path including a cooling interface (e.g., heat exchanger associated with the sink portion of the TESS 110).

The fluid can be moved through the tubes or conduits actively, such as by a pump or impeller. The pump can be any suitable pump configured to move fluid at a desired rate. For example, the type of pump used may be a diaphragm pump, peristaltic pump, etc. In a variation on this approach, rather than relying only on the specific heat of the transported fluid to convey the thermal energy, TC 150 can also rely on phase transition of a fluid, thus using the latent heat of the fluid in addition to its specific heat. This approach can be implemented as, for example, a heat pipe, with a fluid such as water or ammonia that can change phase around the temperature range of interest for system 100.

Controller 180 can be any suitable compute device that can electronically control functioning of the system 100. The controller 180 can be configured to be appropriately suited for the corresponding implementation of the system 100, including any suitable hardware-based computing device and/or a multimedia device, such as, for example, a server, a microprocessor, a desktop compute device, a smartphone, a tablet, a wearable device, a laptop and/or the like.

Figure 3E:
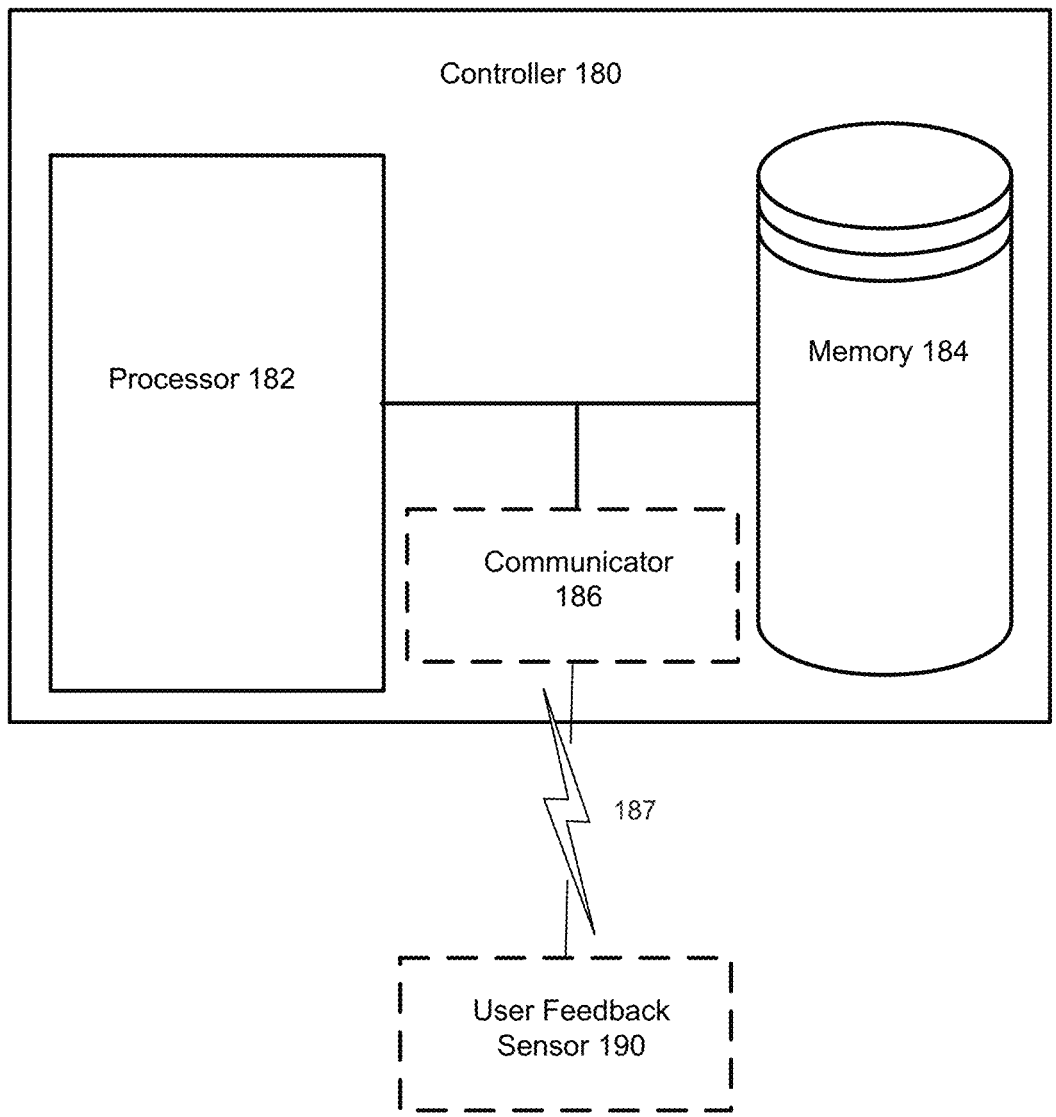
FIG. 3E is a schematic representation of a controller and optional user feedback sensor of a thermal modulation system, according to an embodiment.

FIG. 3E is a schematic block diagram of controller 180 and an optional user feedback sensor 190, according to an example implementation. The controller 180 includes a processor 182, a memory 184 (e.g., including data storage), and optionally a communicator 186.

The processor 182 can be, for example, a hardware based integrated circuit (IC) or any other suitable processing device configured to run and/or execute a set of instructions or code. For example, the processor 182 can be a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 182 can be operatively coupled to the memory 184 through a system bus (for example, address bus, data bus and/or control bus).

The processor 182 can be configured to send instructions to one or more components of the system 100 to operate the components. For example, the processor 182 can generate and/or receive instructions and send instructions to activate and/or deactivate TESS 110, one or more fluid movers or flow controllers to convey fluid via the TC 150, one or more portions of the thermal applicator 170, and/or sensor(s) 190, following the associated instructions. In some embodiments, the processor 211 can be configured to maintain logs or schedules of thermal neural modulation and associated instructions used to carry out the modulation. In some embodiments, the instructions used to carry out the modulation are adjusted by the processor 211 based on information provided by or related to the patient. The processor 182 can also be configured to maintain a log of information related to the patient (e.g., identifier of the patient, time and date of treatment, settings and preferences associated with the patient (e.g., temperature settings for heating and/or cooling, duration of treatment, etc.), timetable of treatment administration, etc.). The processor 182 can store data and/or files associated with a patient and/or a treatment approach or protocol. In some embodiments, the processor 182 can receive feedback from the sensor(s) 190 and/or the patient (e.g., behavioral responses including perception of degree of pain, level of pain relief experienced, physiological responses like heart rate, breathing, blood pressure, etc., and input provided by the patient like sensitivity to heat, sensitivity to cold temperatures, and extent of hair in the target anatomy).

The memory 184 of the controller 180 can be, for example, a random access memory (RAM), a memory buffer, a hard drive, a read-only memory (ROM), an erasable programmable read-only memory (EPROM), and/or the like. The memory 184 can store, for example, one or more software modules and/or code that can include instructions to cause the processor 182 to perform one or more processes, functions, and/or the like (e.g., receiving signals from sensors 190, sending signals to fluid movers and/or flow controllers, sending signals to heating and/or cooling elements associated with TESS 110, etc.). In some embodiments, the memory 184 can include extendable storage units that can be added and used incrementally. In some implementations, the memory 184 can be a portable memory (for example, a flash drive, a portable hard disk, and/or the like) that can be operatively coupled to the processor 182. In other instances, the memory can be remotely operatively coupled with the controller 180. For example, a remote database server can serve as a memory and be operatively coupled to the compute device.

The communicator 186 can be a hardware device operatively coupled to the processor 182 and memory 184 and/or software stored in the memory 184 executed by the processor 182. The communicator 186 can be, for example, a network interface card (NIC), a Wi-Fi™ module, a Bluetooth® module and/or any other suitable wired and/or wireless communication device. Furthermore, the communicator 186 can include a switch, a router, a hub and/or any other network device. The communicator 186 can be configured to connect the controller 180 to a communication network. In some instances, the communicator 186 can be configured to connect to a communication network such as, for example, a near field communication (NFC) network, the Internet, an intranet, a local area network (LAN), a wide area network (WAN), a metropolitan area network (MAN), a worldwide interoperability for microwave access network (WiMAX R), an optical fiber (or fiber optic)-based network, network using TCP/IP (including HTTP and other protocols), networks implementing WLAN (including 802.11a/b/g/n and other radio frequency-based protocols and methods), network supporting analog transmissions, Global System for Mobile Communications (GSM), 3G/4G/LTE, a Bluetooth® network, a virtual network, network implementing communications via ZigBee, EnOcean, TransferJet, Wireless USB, and/or any combination thereof.

In some instances, the communicator 186 can facilitate receiving and/or transmitting data and/or files through a communication network. In some instances, a received file can be processed by the processor 182 and/or stored in the memory 184 and used to control the operation of the system 100 as described herein.

In instances in which the system 100 includes an optional user feedback sensor 190, communicator 186 can communicate with the user feedback sensor 190, such as by a wireless communication link 187, e.g. to receive control signals from the feedback sensor and communicate them to processor 182.

Figure 3F:
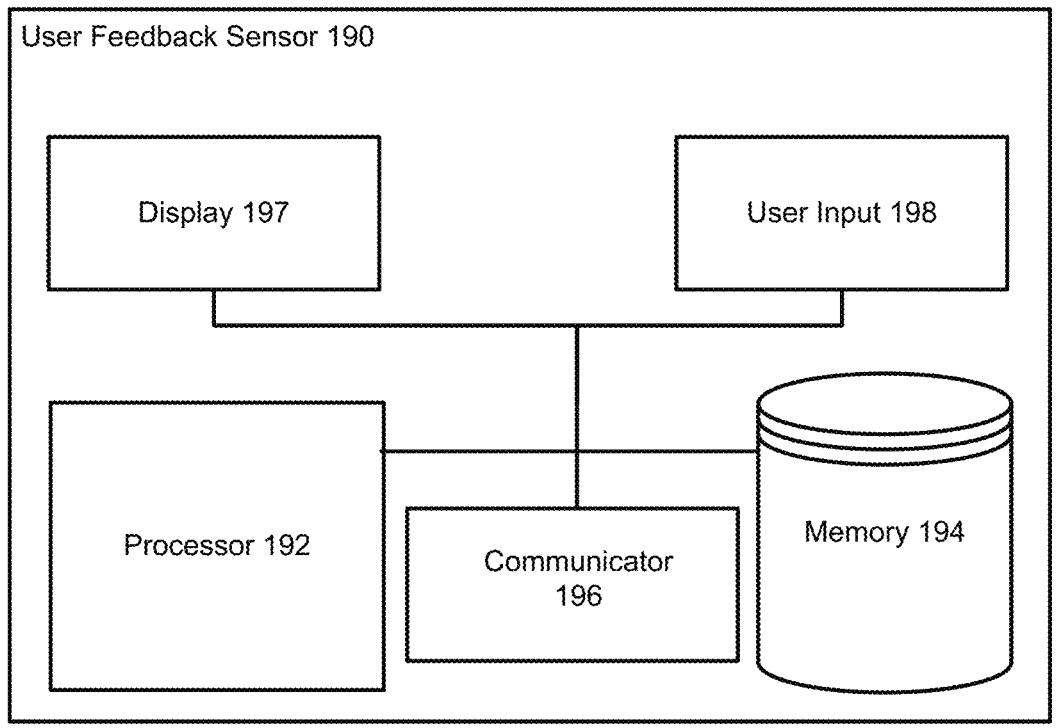
FIG. 3F is a schematic representation of an optional user feedback sensor, according to an embodiment.

An optional user feedback sensor 190 is illustrated schematically in FIG. 3F. User feedback sensor 190 can include a processor 192, memory 194, and communicator 196, which may function, and be implemented, in similar fashion to processor 182, memory 184, and communicator 186, as described above for controller 180. In addition, user feedback sensor 190 may include a display 197 and user input device 198. Display 197 may provide a visual display to the user with input factors from which the user may select, including from a group consisting of pain level, desired extent of motor function, sensory sensitivity including pain, touch, sharpness, density or length of hair in treatment area, sensitivity to hot and cold temperatures, triggers, symptoms including most bothersome symptoms, quality of life including validated questionnaires such as PROMIS-29®, medication usage, healthcare utilization such as office visits, hospital visits, emergency department visits and non-prescription medication usage among other contributors to healthcare costs and utilization, strength, temperature, and stress level, as well as system control inputs such as "on" or "off" or treatment time or duration, desired extent of nerve block, rate of transition between temperatures, treatment temperatures, relative change of temperature (hotter/colder), flow rate, and options for the user to change such control input. User input 198 may provide input mechanisms (dial, knob, button, user interactive panel, and/or the like) by which the user can provide inputs to the user feedback sensor 190 to be communicated to controller 180. In some implementations, display 197 and user input device 198 may be combined, e.g. as a touch screen.

Figure 3G:
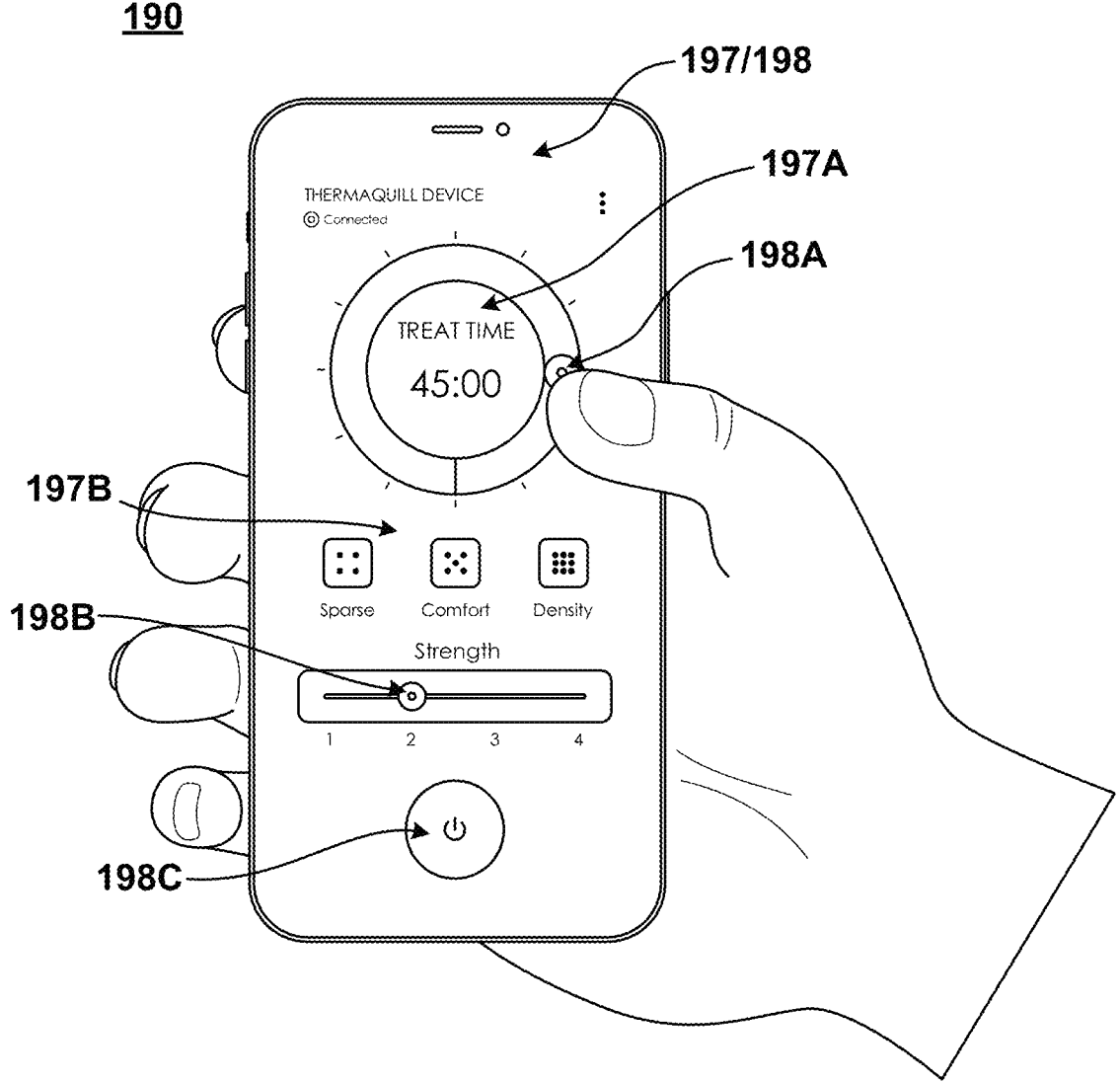
FIG. 3G is an illustration of an implementation of an optional user feedback sensor, according to an embodiment.

An exemplary implementation of a user feedback sensor 190 is shown in FIG. 3G, implemented in software operating on a smartphone or table. As shown in FIG. 3G, user feedback sensor includes a touch screen that combines the functions of display 197 and user input device 198. Display 197 includes a visual indication of total and elapsed treatment time at 197A, and hair density at 197B. User input mechanism include "soft" controls 198A for changing desired treatment time, 198B for changing desired extent of neural blockade, and 198C for on/off. These controls can be changed or swapped at any time on the touch screen with alternate controls: for example, 197A and 198A display and input for changing treatment time may alternately allow user to adjust the current temperature set-point. Patient symptoms can also be input via modified input 197B whereby the severity of each symptom is selected for each day. The display 197 may ask the user survey questions for input, for example following the PROMIS-29® validated quality of life survey. Medication usage and other healthcare utilization may also be captured via the user input display.

Figure 4:
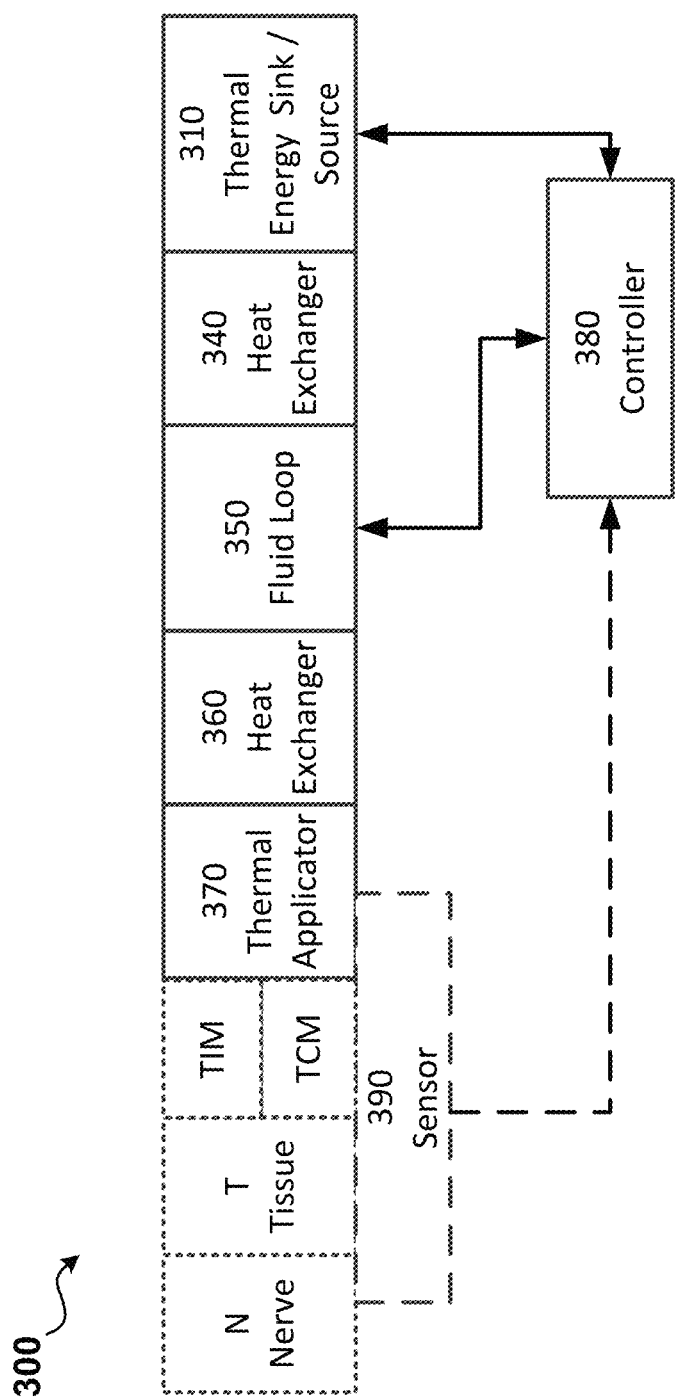
FIG. 4 is a schematic illustration of a thermal neural modulation system, according to an embodiment.

Another embodiment of a thermal neural modulation system 300 is shown schematically in FIG. 4. Portions of the system 300 can be structurally and/or functionally similar to the system 100 described above. In this embodiment, the function of thermal conduit 150 in system 100 described above is implemented as a fluid loop. Thus, thermal neural modulation system 300 includes a thermal energy sink and/or source ("TESS") 310, a first heat exchanger 340, a fluid loop 350, a second heat exchanger 360, a thermal applicator 370, and a controller 380. System 300 may also include one or more sensors 390 (e.g., temperature sensors). TESS 310 may receive heat from and/or provide heat to, respectively, fluid loop 350 via first heat exchanger 340. In turn, fluid loop 350 may receive heat from, and/or provide heat to, thermal applicator 370 via second heat exchanger 360. The operation of system 300 may be controlled by controller 380, which may be, for example, operative coupled to TESS 310 and/or fluid loop 350. The control of system 300 by controller 380 may be based in part on signals received from temperature sensor(s) 390, TESS 310 and/or fluid loop 350.

In some implementations, the system 300 can include an applicator portion that includes the thermal applicator 370 and a portion of the fluid loop 350. In some embodiments, a source (e.g., heat pump or resistive wire) and a sink (e.g., thermal electric cooler or water-ice reservoir) are used to heat and cool fluid, respectively. In some embodiments, the heating fluid can be at about 42° C. to about 54° C. In some embodiments, the cooling fluid is about 0° C. to about 15° C. In some embodiments, cooling fluid is about 0° C. and heating fluid is about 47° C. with a ±2° C. on the surrounding tissue during heating and cooling. The controller 180 may direct the source and/or sink such that the temperatures may be maintained at the nerve. Fluid may be recycled back to the source and/or sink from the thermal applicator 170 for heating or cooling. In some embodiments, the flow rate of the heating or cooling fluid may range from about 0.0001 L/min to about 1 L/min, depending on the surface area that is to be heated or cooled and/or on the temperature of the heating or cooling fluid. A pump may provide pressures of about 5 mbar to about 400 mbar to achieve these flow rates, depending on tubing diameter of the fluid loop.

In some implementations of system 300, thermal applicator 370 is configured to be applied topically to the subject to be treated, e.g. to the skin of the subject's body overlying treatment regions(s) of target nerve(s) to be thermally modulated. Fluid can be circulated through fluid loop 350 to transfer heat to/from topical thermal applicator 370 via second heat exchanger 360, and thus to/from tissue T overlying nerve N. One such implementation is system 400, shown in FIGS. 5A to 5F.

System 400 is similar to the ThermaZone device, available from Innovative Medical Equipment, and to the devices disclosed in US Patent Publication No. 2008/0228248, incorporated by reference herein. The system 400 is an example implementation of the system 300, using a fluid loop to administer thermal neural modulation as described herein. The system 400 includes a sink/source 410 that can be similar to TESS 310.

Figure 5A:
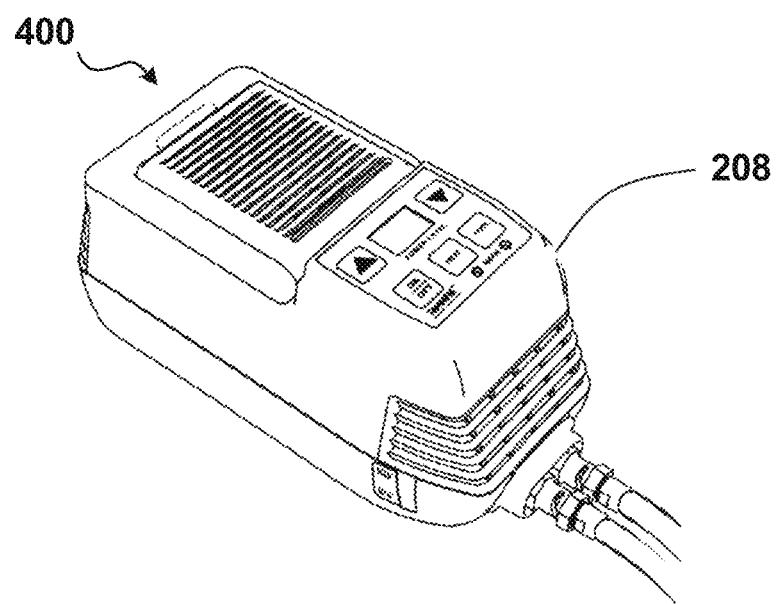
FIGS. 5A-5F are illustrations of a thermal neural modulation system, according to an embodiment.
Figure 5B:
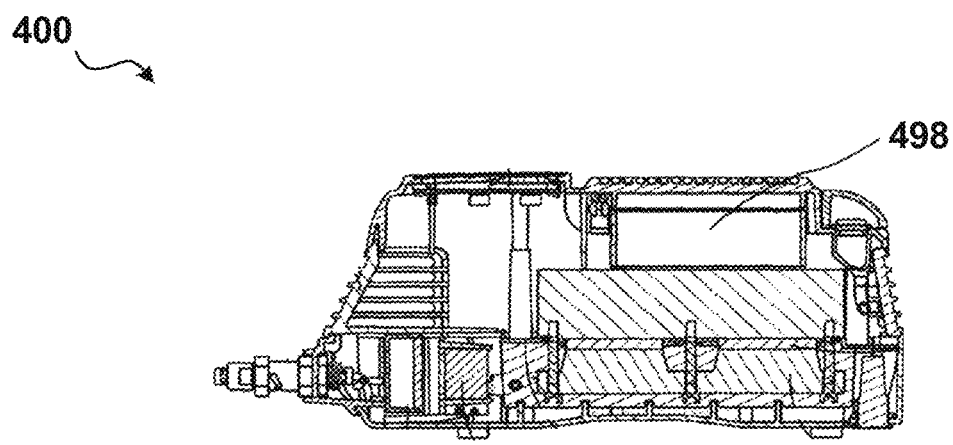
Figure 5C:
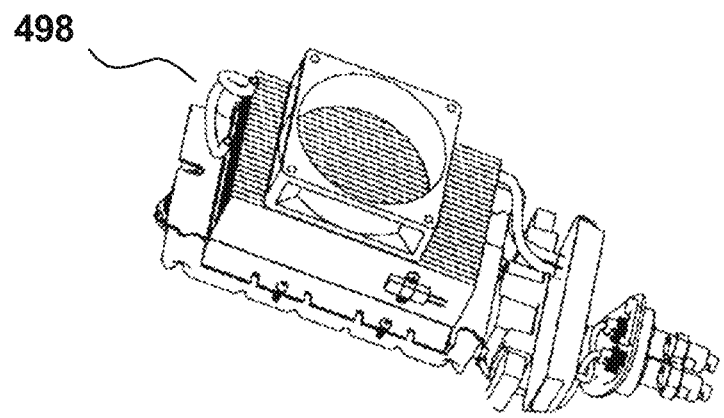
Figure 5D:
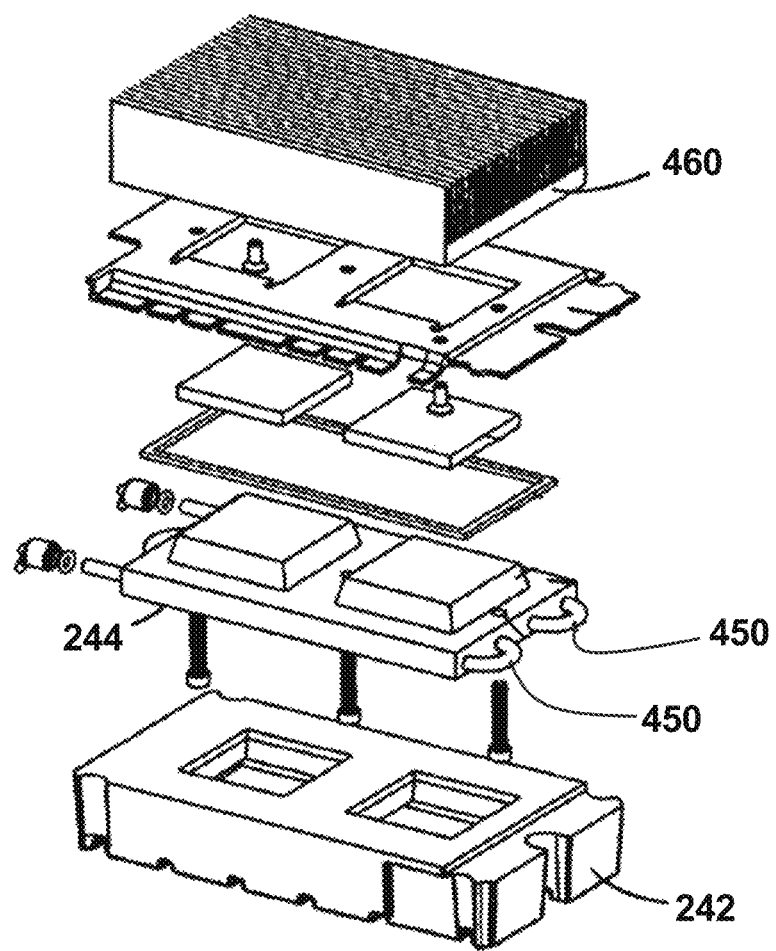

FIGS. 5A and 5B are schematic illustrations of a perspective view and a cross-sectional view of a controller portion 498 of the system 400. FIG. 5C is a perspective top view of the controller portion 498 without the housing. FIG. 5D is an exploded view of components of the system 400, according to an embodiment. The system 400 has a TESS 410 implemented to be switchable between (i) heating a target nerve by transferring thermal energy from a source, implemented using a thermoelectric Peltier heat pump device as an example, to the fluid loop 450 and directed to an applicator (not shown) and (ii) cooling a target nerve by transferring thermal energy from the nerve to the fluid loop 450 and to a sink implemented using cooling plates as an example. The system 400 includes a fluid loop 450 interfacing with a heat exchanger 440 mediating transfer of thermal energy between the fluid loop 450 and the TESS 410. The system includes a pump 204 that circulates fluid through the fluid loop 450 and a fan and a heat sink to dissipate thermal energy received from the fluid loop 450. The system 400 can include one or more sensors (e.g., temperature sensors) to aid in the setting of temperature of the sink/source and/or the temperature of the thermal applicator 470. The system 400 can be operated using a controller (e.g., using a PCB). The system 400 can be powered by any suitable power source, such as direct 12 V (e.g. car power adaptor) or via a AC/DC converter or by a battery pack (either single use or rechargeable).

Figure 5E:
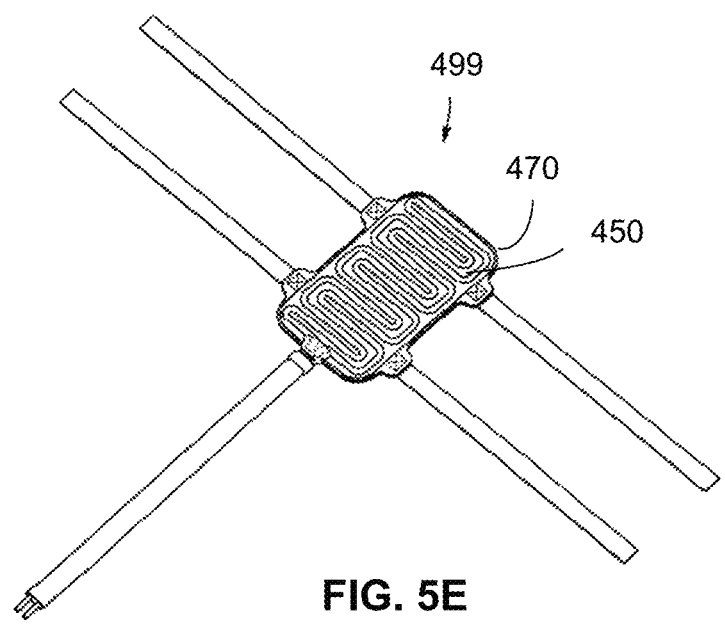
Figure 5F:
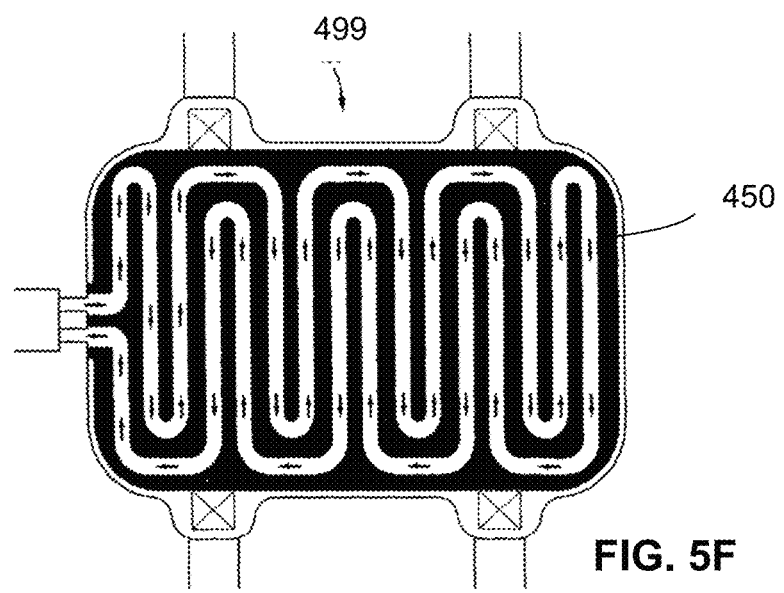

FIGS. 5E and 5F are schematic illustrations of a perspective view and a top view of applicator portion 499 of the system 400 configured to interact with the tissue adjacent to or in contact with a target nerve of a patient. The portion 499 of the system 400 includes applicators 470 substantially similar in structure and/or function to the thermal applicator 170, and 370 described above, and portions of the fluid loop 450. For example, as shown in the example embodiment in FIGS. 5E and 5F, the system 400 includes a body pad shaped/sized to enable administration of thermal modulation anywhere on the body. The example illustrated shows a serpentine shape of the fluid loop. In other implementations, the fluid loop could be patterned so that certain areas are more densely occupied than others to target these particular areas.

In some applications of thermal modulation, it may be desirable to have the thermal applicator encircle an extremity of the body of the treatment subject, for example one or more digits (finger, toe) or limbs (upper and/or lower leg, upper and/or lower arm, ankle and/or wrist). In such applications, it can also be desirable for the system to be portable so that the subject can be treated while conducting normal activities. This concept can be extended further to the entire system being wearable by the user. In some implementations, a wearable system can be configured to allow a user to continue performing day-to-day activities without hindrance. For example, in some embodiments, the wearable thermal modulation system can be water resistant and/or water proof. In some embodiments, the wearable system can be resistant to changes in ambient pressure, body posture and other movements or changes in orientation related to movement of a user's body. The wearable system can include an applicator portion and a control portion. Another implementation of a system with a fluid loop and topical application of a thermal applicator that can be useful for such applications is system 500, shown schematically in FIG. 6.

The thermal neural modulation system 500 includes an applicator portion 599 and a control portion 598, and a coupling portion (not shown) configured to include a portion of the fluid loop 550 and in some instances include one or more data cables forming an electrical connection between the applicator portion 599 and the control portion 598. In some implementations, the applicator portion 599 may partially encircle a portion of a body of a patient (e.g., a digit, extremity, joint, head, neck etc.) as shown by the solid lines of the applicator 570, the fluid loop 550 and the heat exchanger 560, leaving a portion uncovered (e.g., the portion of the thermal applicator 570, the heat exchanger 560 and the fluid loop 550 indicated by the dashed lines). In some implementations, the applicator portion 599 may fully or completely encircle a portion of the body (e.g., a digit, an extremity, etc.) at which the thermal modulation is being administered. The applicator portion 599 includes the thermal applicator 570. The applicator portion 599 may be constructed of a variety of materials including closed cell foam, open cell foam, etc. The applicator portion 599 can include fluid channels that are a portion of the fluid loop 550. The channels through which the liquid flows may be constructed of any suitable material including vinyl, polyurethane, or metal (e.g., copper or aluminum), etc. The channels material may be covered with some other type of material (e.g. plastic, fabric, plush, etc.) or could be in direct contact with a patient's tissue. In some embodiments, the fluid channels can have one entrance and one exit and these are positioned adjacent to each other. In some embodiments, the entrance and exit can be positioned at opposite ends of an applicator portions or in any other suitable configuration. The fluid channels can cover, substantially and evenly, most of the surface area of the applicator portion. In other embodiments, the fluid channels can be configured to densely cover some areas while sparsely cover other areas such that the densely covered areas can be placed against target areas that require increased delivery of thermal modulation.

The control portion 598 includes thermal energy sink and/or source ("TESS") 510, a first heat exchanger 540, a fluid loop 550, a second heat exchanger 560, and a controller 580. The fluid loop 550 can be configured to encircle a digit, an extremity or another body portion including the target nerve N and the tissue T proximal to the nerve N. In some embodiments, the heat exchanger 560 and thermal applicator 570 can be configured to encircle the digit, extremity or the other body portion of a patient. In some embodiments, the system 500 can include one or more thermally conductive materials (TCM) and/or thermally insulating material (TIM) disposed between the thermal applicator 570 and a contact surface of the tissue T proximal to the target nerve N. In some embodiments, the system 500 may also include one or more temperature sensors 590. TESS 510 may receive heat from and/or provide heat to, respectively, fluid loop 550 via first heat exchanger 540. In turn, fluid loop 550 may receive heat from, and/or provide heat to, thermal applicator 570 via second heat exchanger 560. The controller 580 can be operatively coupled to the components including TESS 510, the fluid loop 550, and optionally the sensors 590. The controller 580 can control and/or mediate the operation of system 500. The control of system 500 by controller 580 may be based in part on signals received from temperature sensor(s) 590, TESS 510 and/or fluid loop 550.

While the system 500 is illustrated and described to include a fluid loop 550 configured to mediate transfer of thermal energy between the target nerve N and the TESS 510, the transfer of thermal energy between the target nerve N and the TESS 510 is not limited to a fluid loop configuration. In some embodiments, the delivery and/or the withdrawal of thermal energy to/from the target nerve N and the tissue T, and to/from the TESS 510 can be conducted using any other suitable method. For example, embodiments could use any of the approaches described herein to implement a thermal energy source and/or sink used for delivery/withdrawal by the thermal applicator, including local inductive or resistive heating, vapor cycle, etc.

In some embodiments, the wearable system 500 or portions of it may be constructed from a soft conforming elastic material (for example, Shore Scale 25A) with straps or other such suitable means to conform to a target location of a patient. In some embodiments, a thin conforming thermally conductive elastomer, such as COOLPOLY® Thermally Conductive Plastic (Celanese, Ltd.) may coat a side of the wearable system that contacts the skin of the patient such that the wearable system and/or the applicator portion may make thermal contact. In some embodiments, a thermally conductive gel may be used to improve the thermal contact with the wearable system. For example, the wearable system may be a headband positioned to treat conditions involving pain associated with the occipital nerve.

Figure 7A:
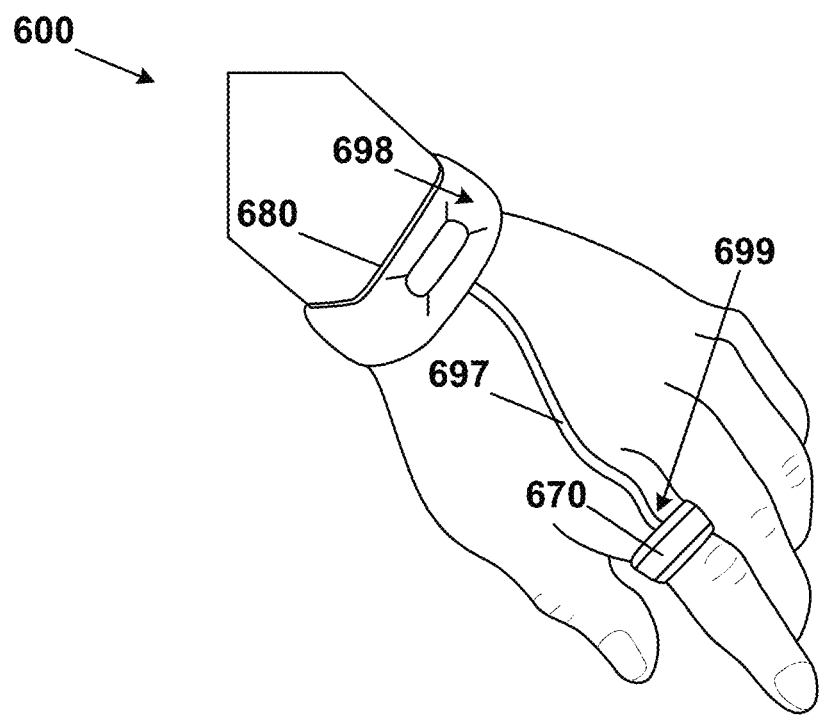
FIGS. 7A-7B are illustrations of a thermal neural modulation system for treatment of a single finger, according to an embodiment.
Figure 7B:
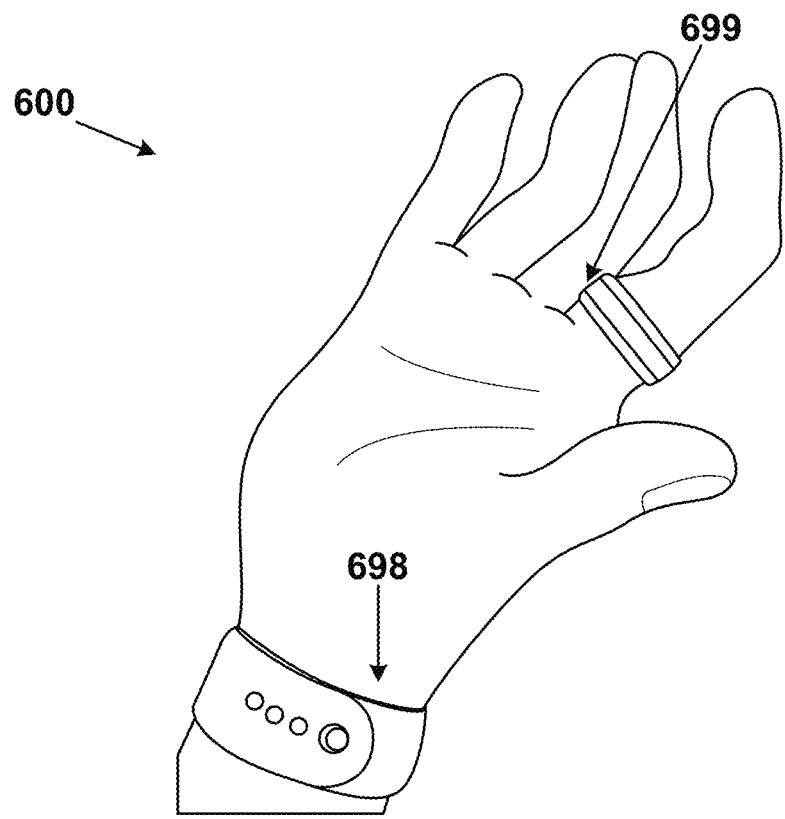

One implementation of a system incorporating the concepts of system 500 is system 600, which is configured for application of thermal neural modulation of nerves in a single digit, in this example a finger, of the treatment subject. As shown in FIGS. 7A and 7B, system 600 includes the control portion 698, the applicator portion 699 and a coupling portion 697. The control portion 698 includes thermal energy sink and/or source ("TESS") (not shown), a fluid loop 650, and a controller 680. The applicator portion 699 includes a portion of the fluid loop 650 and the thermal applicator 670. The control portion 698 includes a first heat exchanger (not shown) at the interface between the TESS and the fluid loop 650. The applicator portion 699 includes a second heat exchanger (not shown) at the interface between the fluid loop and the thermal applicator 670. The coupling portion 697 can include a portion of the fluid loop 650, providing fluid coupling between the applicator portion 699 and the control portion 698, and one or more data cables providing electrical connection between the applicator portion 699 and the control portion 698. The fluid loop 650 can extend from the control portion 698 via the coupling portion 697 to the applicator portion 699. As shown in FIGS. 7A and 7B the applicator portion 699 including the thermal applicator 670) and a portion of the fluid loop 650 can be configured to encircle the portion of the body adjoining or proximal to the portion of the target nerve to be treated via thermal modulation (e.g., a forefinger in FIGS. 7A and 7B). The control portion 698 can be worn by a patient using a suitable attachment or fastening mechanism appropriate to the corresponding use case (e.g., a wristband as shown in FIGS. 7A and 7B). The coupling portion 697 can fluidically couple the applicator portion 699 and the control portion 698. The coupling portion 697 can be of a suitable length and thickness and of a suitable material to ensure secure coupling and be configured to be non-obtrusive or non-cumbersome during use so as not to limit mobility and/or movement of the patient during use of the thermal neural modulation system 600 to the extent possible. In some embodiments the system 600 can include sensors (not shown) coupled to the controller 680 and configured to provide feedback to the controller 680.

The fluid loop 650 can be configured to encircle the body portion (e.g., forefinger) including the target nerve and the tissue proximal to the nerve. In some embodiments, the second heat exchanger and thermal applicator 670 can be configured to encircle the extremity or the body portion of the patient. In some embodiments, the system 600 can include one or more thermally conductive materials (TCM) and/or thermally insulating materials (TIM) disposed between the thermal applicator 670 and a contact surface of the tissue. In use, TESS may receive heat from and/or provide heat to, respectively, fluid loop 650 via first heat exchanger, and the fluid loop 650 may receive heat from, and/or provide heat to, thermal applicator 670 via second heat exchanger. The controller 680 can be operatively coupled to the components including TESS, the fluid loop 650, and optionally the sensors 690

Figure 8A:
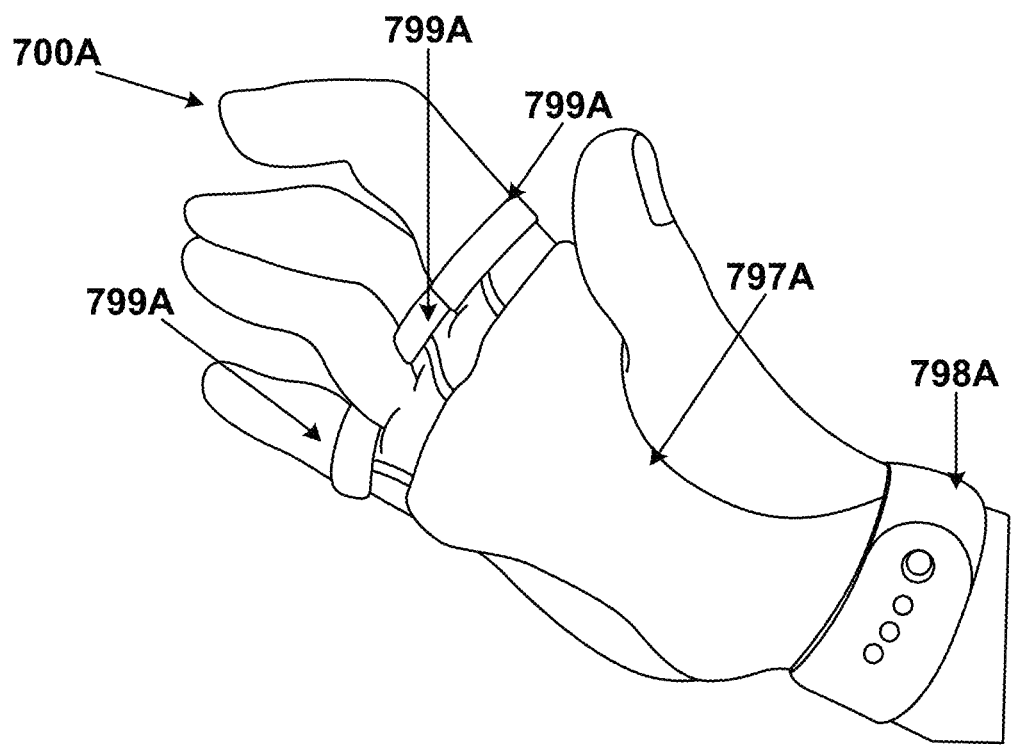
FIGS. 8A-8B are illustrations of a thermal neural modulation system for treatment of a multiple fingers, according to an embodiment.

Two example implementations of a system incorporating the concepts of system 500 are systems 700A and 700B, which are variations configured for application of thermal neural modulation of nerves in multiple digits, in this example multiple fingers, of the treatment subject. As shown in FIG. 8A, system 700A includes the control portion 798A and the applicator portion 799A coupled by the coupling portion 797A. The control portion 798A includes thermal energy sink and/or source ("TESS"), a fluid loop, and a controller. The applicator portion 799A includes multiple portions of the fluid loop and the thermal applicator configured to encircle each of three fingers as shown in FIG. 8A. The coupling portion 797A is configured in the form of a sheath or pad including a portion of the fluid loop and fluidically coupling the control portion 798A and the applicator portions 799A. The control portion 798A can include a first heat exchanger at the interface between the TESS and the fluid loop. The applicator portions 799A can each include a second heat exchanger (not shown), at the interface between the fluid loop and the thermal applicator, as described previously. The fluid loop can extend from the control portion 798A via the coupling portion 797A to the applicator portion 799A. As shown in FIG. 8A the applicator portion 799A including the applicator and a portion of the fluid loop can be configured to encircle the digits of the hand and be used to simultaneously treat target nerves in the fingers via thermal modulation. In some embodiments, the fluid loop can be configured such that a single fluid loop extends between the TESS and the multiple thermal applicators in the applicator portion 799A moving the fluid from the TESS via the fluid loop and through all the thermal applicator portions. In some embodiments, the fluid loop can be configured such that each thermal applicator of the applicator portion 799A can be coupled to the control portion 798A via an isolated or fluidically separate portion of the fluid loop such that each digit can be independently thermally modulated (e.g., each digit can be heated or cooled independent of the other digits). For example, the system 700A can include individual and isolated fluid loops extending from the control portion with separate first heat exchangers interfacing between the TESS and each isolated fluid loop, extending to each of the applicator portions 799A, and including separate second heat exchangers interfacing between the isolated fluid loops and the thermal applicators encircling each digit of the hand.

Figure 8B:
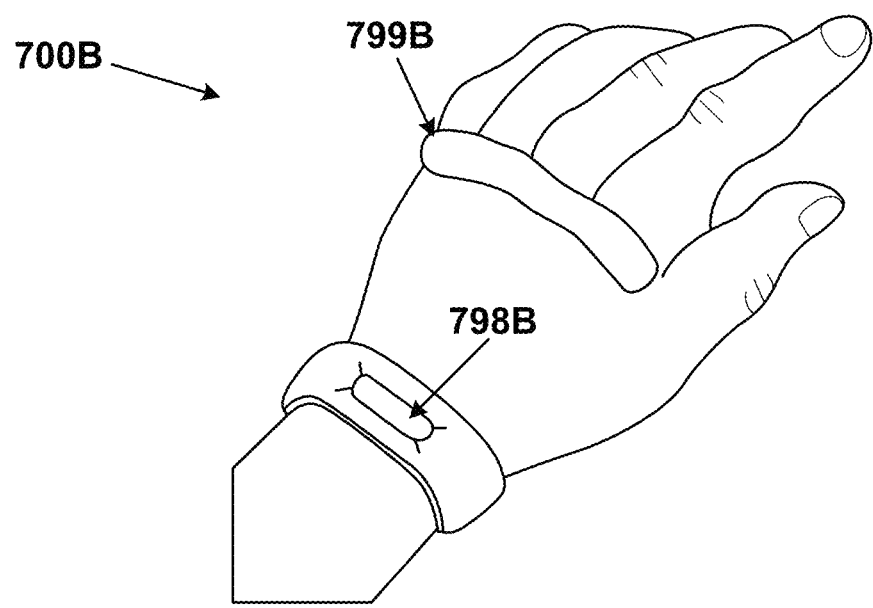

FIG. 8B illustrates a variation 700B of the embodiment 700A in FIG. 8A. The system 700B can be substantially similar in structure and/or function to the embodiment 700A except for the difference in implementation of the applicator portions 799B. Whereas the applicator portions 799A can be configured such that each applicator portion encircles each of the three digits, the applicator portions 799B of the system 700B can be configured such that each applicator portion partially or fully encircles each digit such that the applicator portion can be clasped or otherwise fitted or held on the digit with or without complete coverage around the digit.

The control portion 798A and/or the control portion 798B can be worn by a patient using a suitable attachment or fastening mechanism appropriate to the corresponding use case (e.g., a wristband as shown in FIGS. 8A and 8B). In some embodiments the system 700A and/or the system 700B can include sensors (not shown) coupled to the corresponding controllers and configured to provide feedback as described previously with reference to the system 600 above.

Figure 9A:
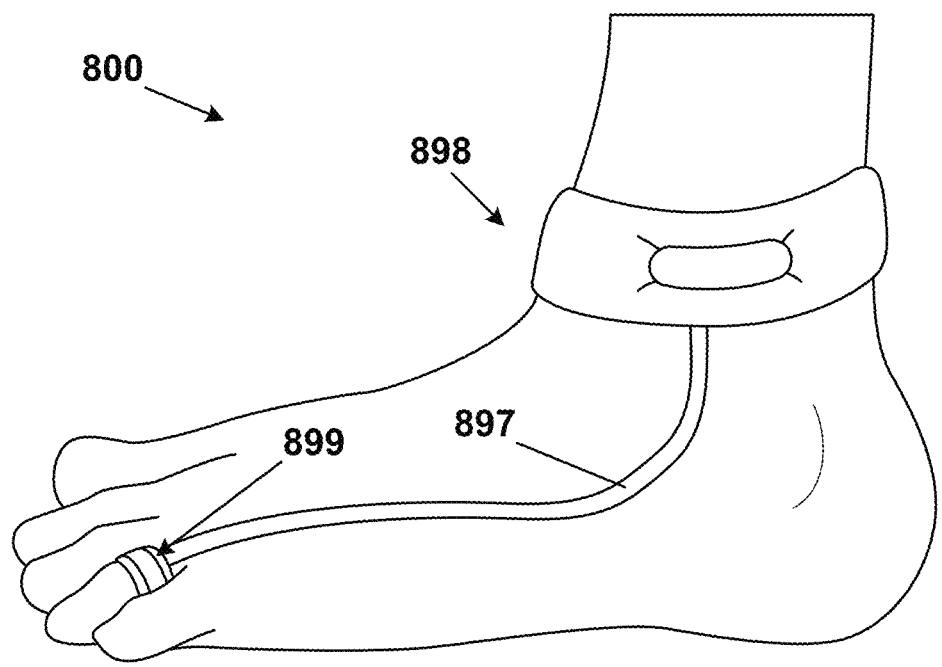
FIGS. 9A-9D are illustrations of a thermal neural modulation system for treatment of a single toe, according to an embodiment.

One implementation of a system incorporating the concepts of system 500 is system 800, which is configured for application of thermal neural modulation of nerves in a single digit, in this example a toe, of the treatment subject. As shown in FIG. 9A, system 800 includes the control portion 898 and the applicator portion 899 coupled by the coupling portion 897. As described with reference to the systems 600, 700A, and 700B above, the control portion 898 includes thermal energy sink and/or source ("TESS"), a fluid loop, and a controller (not shown). The applicator portion 899 includes a portion of the fluid loop and the thermal applicator directed towards the tissue proximal to the target nerve to be treated. The control portion 898 can include a first heat exchanger at the interface between the TESS and the fluid loop. The applicator portion 898 can include a second heat exchanger (not shown), at the interface between the fluid loop and the thermal applicator. The fluid loop can extend from the control portion 899 via the coupling portion 897 to the applicator portion 898. As shown in FIG. 9, the applicator portion 898 including a portion of the fluid loop can be configured to encircle the portion of a digit (e.g., a toe) proximal to the portion of the target nerve to be treated via thermal modulation. In some embodiments, the system 600 can include one or more thermally conductive materials (TCM) and/or thermally insulating material (TIM) disposed between the thermal applicator and a contact surface of the tissue.

The control portion 898 can be worn by a patient using a suitable attachment or fastening mechanism appropriate to the corresponding use case (e.g., an ankle band as shown in FIG. 9A). The coupling portion 897 can fluidically couple the applicator portion 899 and the control portion 898. The coupling portion 897 can be of a suitable length and thickness and of a suitable material to ensure secure coupling and be configured to be non-obtrusive or non-cumbersome during use so as not to limit mobility and/or movement of the patient during use of the thermal neural modulation system 800. In some implementations, the coupling portion 897 can be configured to conform to the portion of the body lying against it. For example, in some implementations the coupling portion 897 can be configured to conform to the contours of a foot of the portion as shown in FIG. 9A. In some embodiments the system 800 can include sensors (not shown) coupled to the controller and configured to provide feedback to the controller.

Figure 9B:
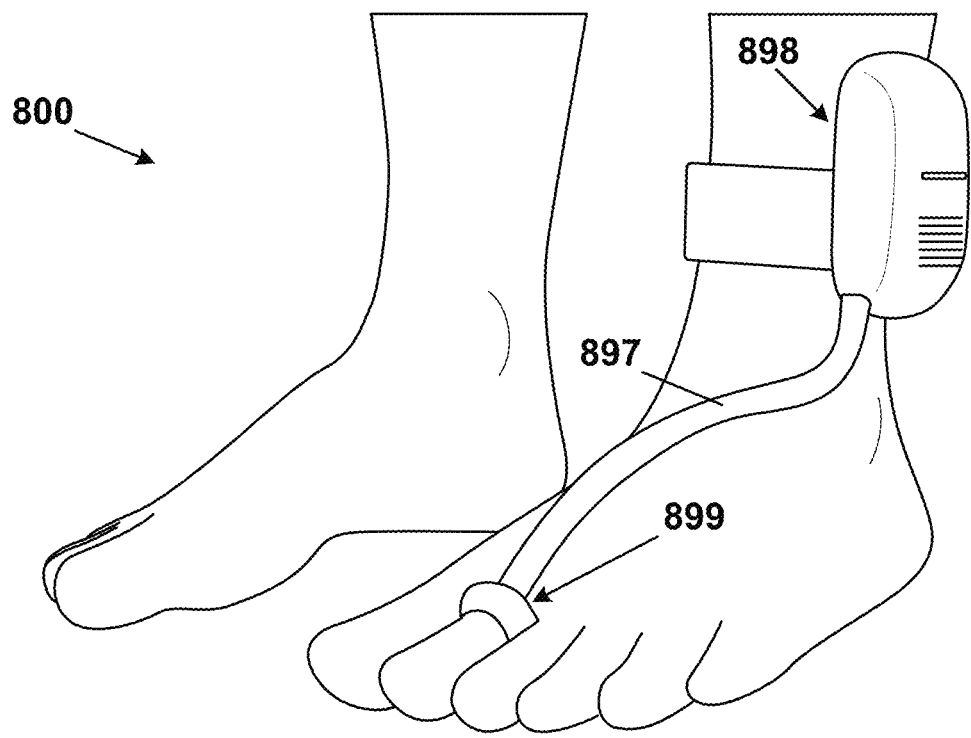
Figure 9C:
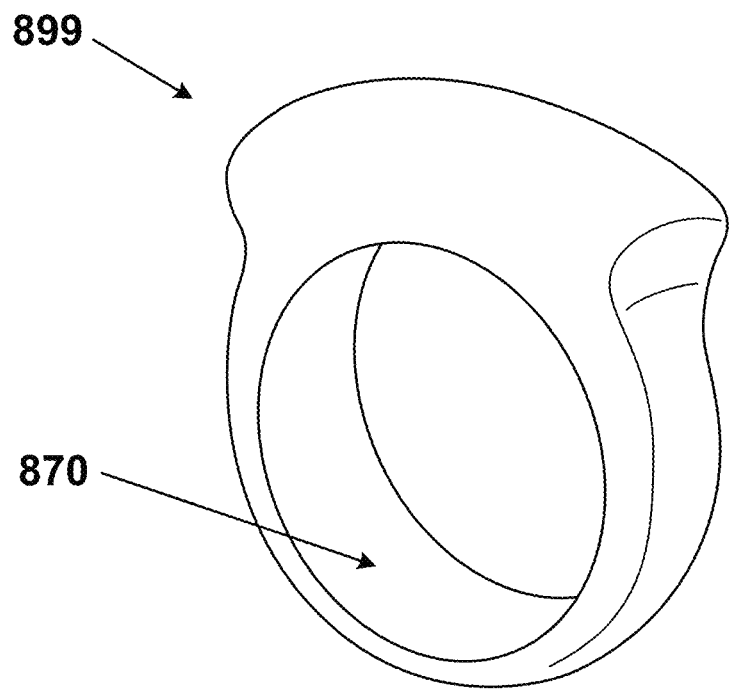
Figure 9D:
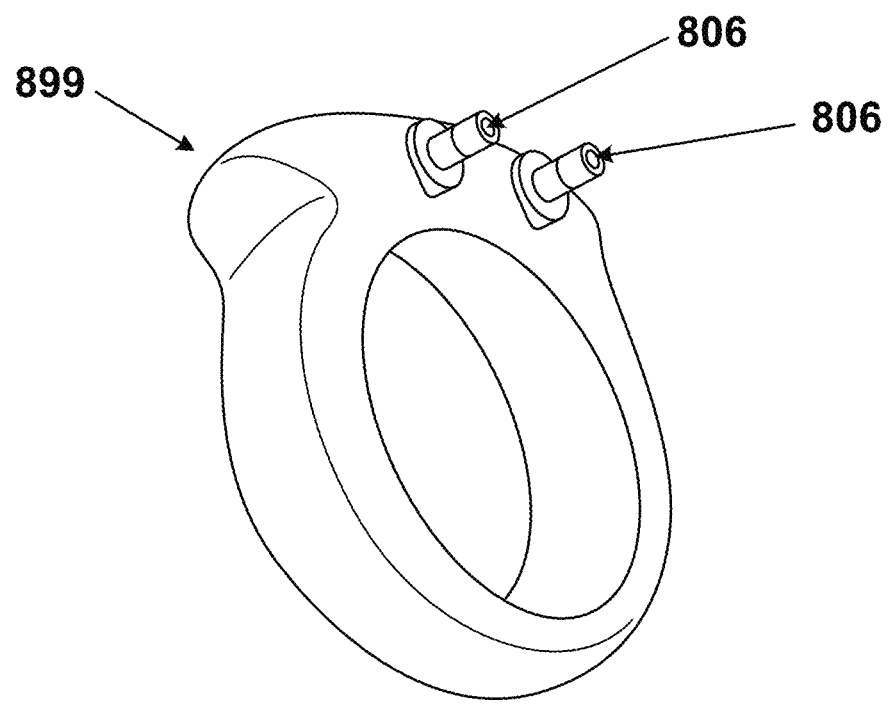

A more detailed illustration of system 800 is shown in FIGS. 9B to 9D. As can be seen in FIG. 9C, applicator portion 899 includes thermal applicator 870 on the inner surface of applicator portion 899, configured to contact the skin of the toe to which it is applied. As can be seen in FIG. 9D, applicator portion 899 includes fluid channel 806 to which fluid from control portion 898 can be transferred through fluid loop 850 and coupling portion 897, and can be circulated through application portion 899, and deliver thermal energy to and/or from thermal applicator 870.

In use, TESS may receive heat from and/or provide heat to, respectively, fluid loop via first heat exchanger, and the fluid loop 850 may receive heat from, and/or provide heat to, thermal applicator via second heat exchanger. The controller can be operatively coupled to the components including TESS, the fluid loop, and optionally the sensors.

Figure 6:
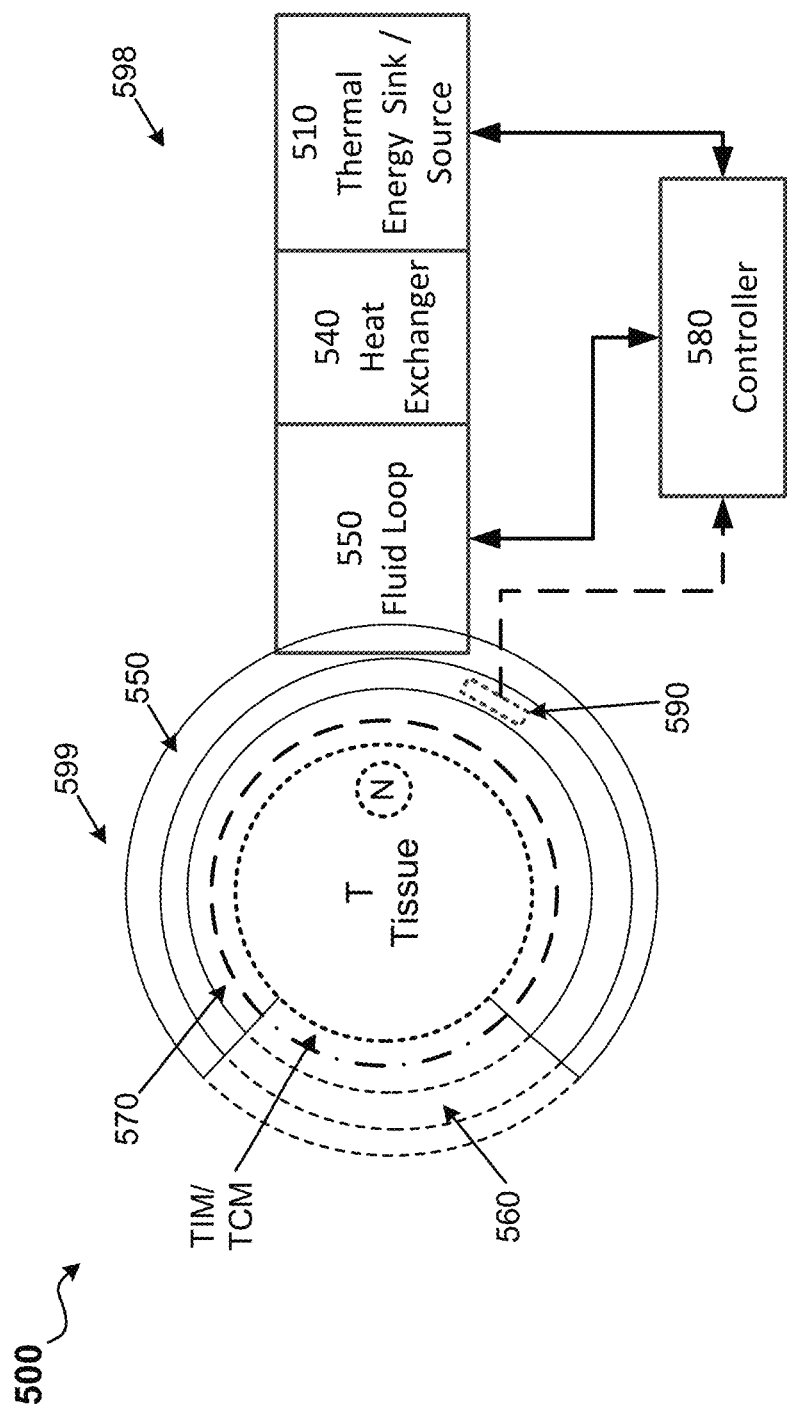
FIG. 6 is a schematic illustration of a thermal neural modulation system, according to an embodiment.
Figures 10A, 10B, 10C:
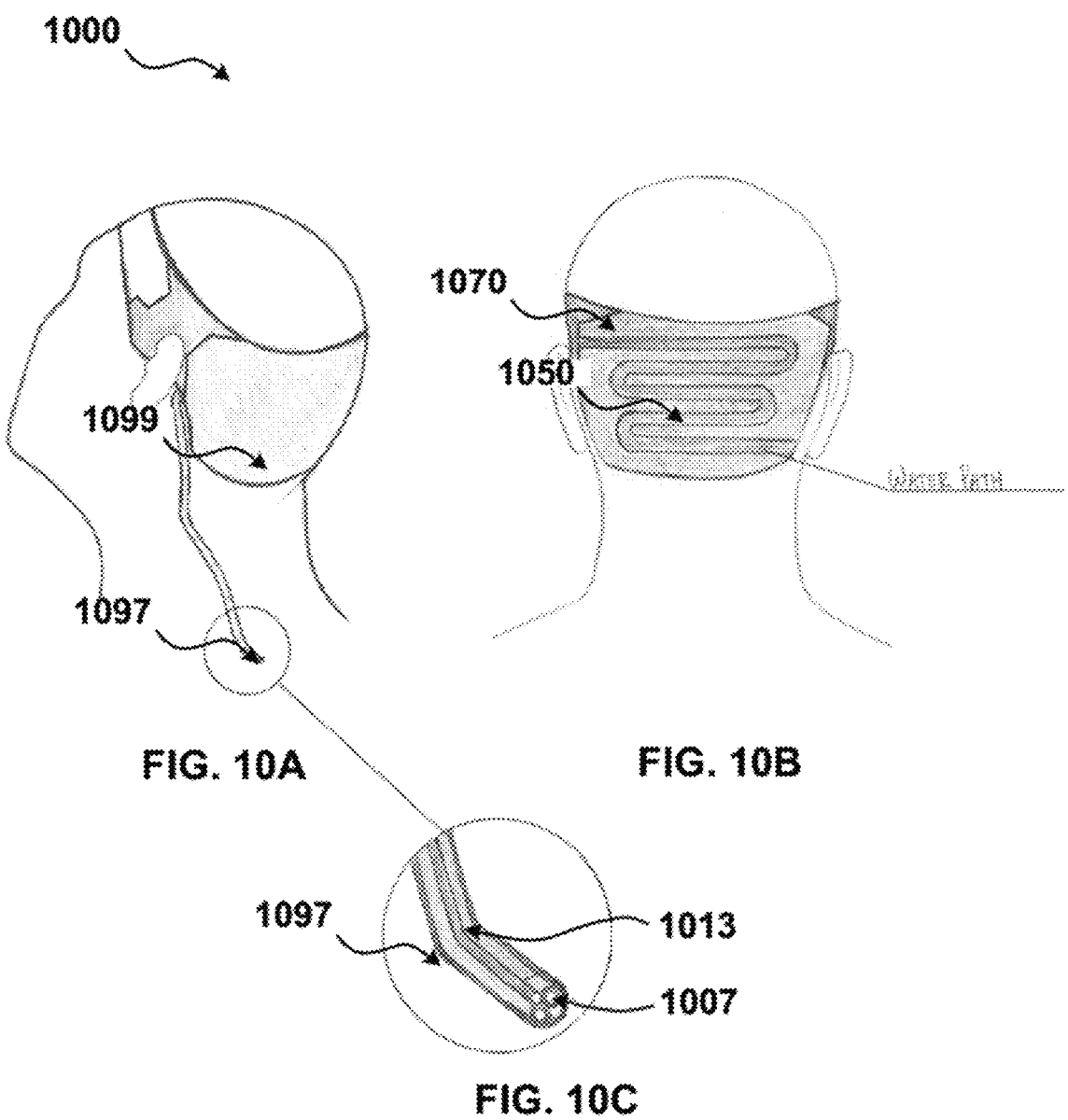
FIGS. 10A-B are schematic illustrations of use and implementation of a thermal neural modulation system, according to an embodiment.
FIG. 10C is an illustration of a coupling portion of the system of FIGS. 10A-B.

Thermal modulation systems can be implemented in several other embodiments configured to be worn by a user. FIGS. 10A-C illustrate an example implementation. The thermal modulation system 1000 is another implementation of a thermal applicator for use in treating the occipital region, using a fluid loop, such as shown in FIGS. 4-6. The system 1000 illustrated in FIGS. 10A-10C is implemented to be worn on an occipital region or back portion of the head/neck of a patient, to provide thermal modulation therapy, according to an embodiment. The system 1000 includes the applicator portion 1099, a system controller portion that can be worn by a user (not shown) and a coupling portion 1097 coupling the applicator portion 1099 to the controller portion. FIG. 10A shows the fastening of the applicator portion 1099 in use and FIG. 10B shows a sectional view of the internal components of the applicator portion 1099 including the thermal applicator 1070 and portions of the fluid loop 1050 arranged in serpentine shape and used to circulate temperature modulated fluid to administer thermal modulation therapy to the occipital region of the patient for example targeting the occipital nerve.

FIG. 10C shows a magnified view of the internal arrangement of the coupling portion 1097 including fluid tubing 1007 that forms portions of the fluid loop 1050 and data cables 1013 used to send and receive data communications between the system controller and the applicator portion of the system 1000. The tubing 1007 can include an inlet tube and an outlet tube. The inlet can carry fluid treated to be at a desired temperature to deliver the thermal modulation to the patient and the outlet can remove the fluid once the thermal modulation has been administered to be recirculated in the system 1000. In some embodiments, the inlet and the outlet can be on the same side as shown. In some embodiments, the inlet can be on one side and the outlet can be on another side of the applicator portion 1099.

FIGS. 11A-11C illustrate a wearable thermal modulation system 1100 according to another embodiment. The thermal modulation system 1100 is yet another implementation of a thermal applicator for use in treating the occipital region, using a fluid loop. The system 1100 is an implementation of the systems shown in FIGS. 4-6 and may be similar in certain aspects to the system 1000 of FIGS. 10A-C. The system 1100 illustrated in FIGS. 11A-11C can be worn on a head/neck of a patient, by fastening using an earpiece 1129 that goes over and partially around the ear, to provide thermal modulation therapy, according to an embodiment. The system 1100 includes the applicator portion 1199, a system controller portion 1198 that can be worn by a user (e.g., on a belt, or on an arm as shown in FIG. 11A) and a coupling portion 1197 coupling the applicator portion 1199 to the controller portion 1198. FIG. 11A shows the fastening of the applicator portion 1099 and the controller portion 1198 in use. FIG. 11B shows a magnified view of the applicator portion 1099 including the earpiece 1129 and FIG. 11C shows a magnified view of the coupling portion 1197 and its internal arrangement including the fluid tubing 1107 and the data cables 1113 used to send and receive data communications between the system controller 1198 and the applicator portion 1199 of the system 1100.

Figures 12A, 12B:
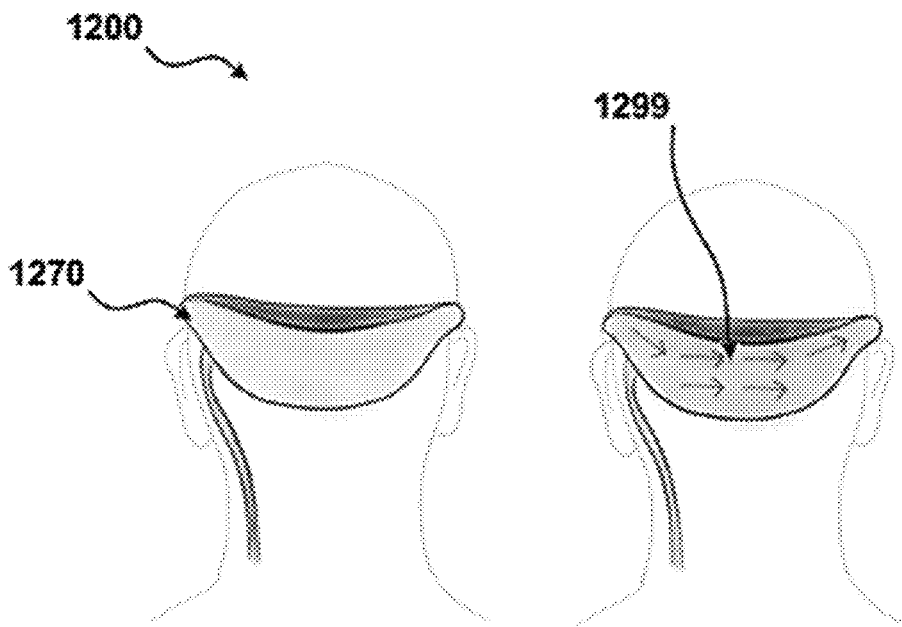
FIGS. 12A-B are schematic illustrations of use and implementation of a thermal neural modulation system, according to an embodiment.
Figure 12C:
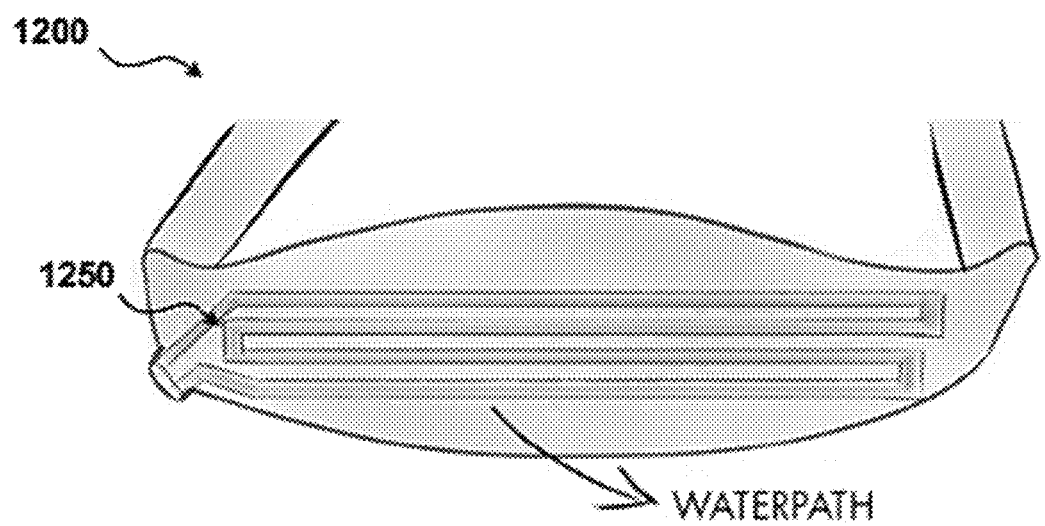
FIG. 12C is an illustration of a fluid path defined in an applicator portion of the system of FIGS. 12A-B.

FIGS. 12A-12C illustrate another implementation of a wearable thermal modulation system 1200 according to another embodiment. The system 1200 is yet another implementation of a thermal applicator for use in treating the occipital region, using a fluid loop. The system 1200 is an implementation of the systems shown in FIGS. 4-6 and may be similar in certain aspects to the system 1000 of FIGS. 10A-C and/or the system 1100 of FIGS. 11A-11C. The system 1200 includes an applicator portion 1299 including a thermal applicator 1270 and portions of the fluid loop 1250. The applicator portion 1299 as shown in FIG. 12B can have a fluid path that is in a serpentine path with the inlet and the outlet on the same side, as shown in FIG. 12C.

Figure 13A:
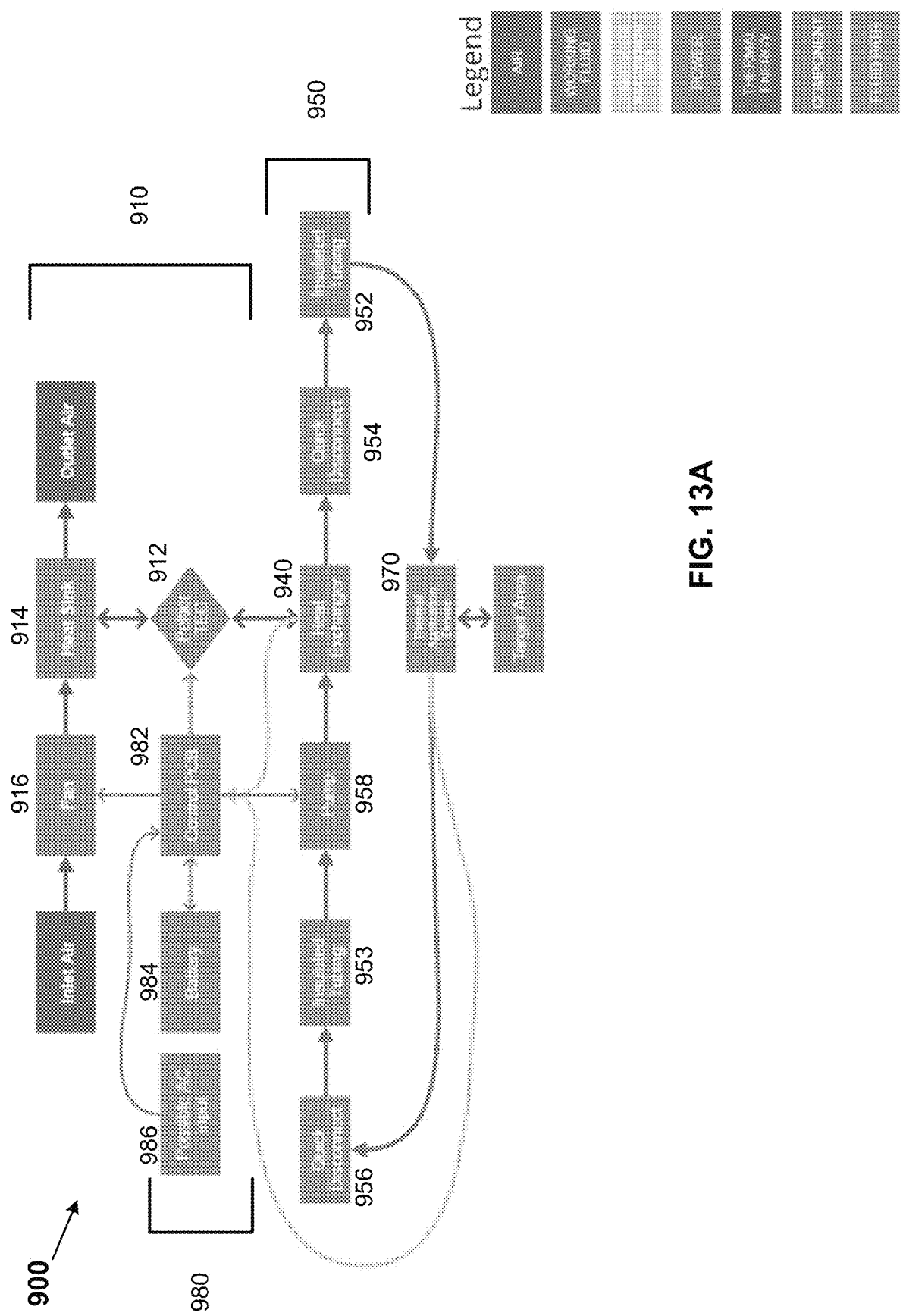
FIG. 13A is a schematic representation of a thermal modulation system and its operation according to an embodiment.

A system 900 and its operation are shown schematically in FIG. 13A. System 900 reflects an approach to implementing a wearable thermal modulation system mediating transfer of thermal energy via a fluid loop. Thus, system 900 includes thermal energy sink/source (TESS) 910, heat exchanger 940, a fluid loop 950, a thermal applicator 970, and a controller 980. TESS 910 is implemented by a Peltier thermoelectric cooler (TEC) 912. The system 900 also includes heat sink 914 thermally coupled to TC 912. The system 900 also includes a fan 916 that can circulate ambient air across heat sink 914, with the ambient air (shown as inlet air and outlet air in FIG. 13A) serving as a sink for thermal energy transferred across TC when TESS 910 is a sink for thermal energy when performing cooling and for waste heat generated by TC 912 and as a source of thermal energy when TESS 910 is a source of thermal energy when performing heating. Fluid loop 950 includes first insulated tubing 952 coupled to quick disconnect 954 to heat exchanger 940 and second insulated tubing 953 coupled to thermal applicator 970 by quick disconnect 956. Fluid loop 950 also includes pump 958 to circulate fluid (e.g. water) through fluid loop 950. Thermal applicator 970 can be implemented as any of the thermal applicators disclosed in the previous embodiments. A heat exchanger and a temperature sensor (not show in FIG. 13A) are associated with thermal applicator 970. Controller 980 includes a control PCB 982 operative coupled to TC 912 to control its operation, to pump 958 to control its operation, and to fan 916 to control its operation. Control PCB can be powered by any of the sources of power disclosed above, including battery 984 and optional alternating current input 986.

Additional embodiments of thermal neural modulation systems and components thereof are described below, with reference to system 100 and its constituent elements as described above.

Figure 13B:
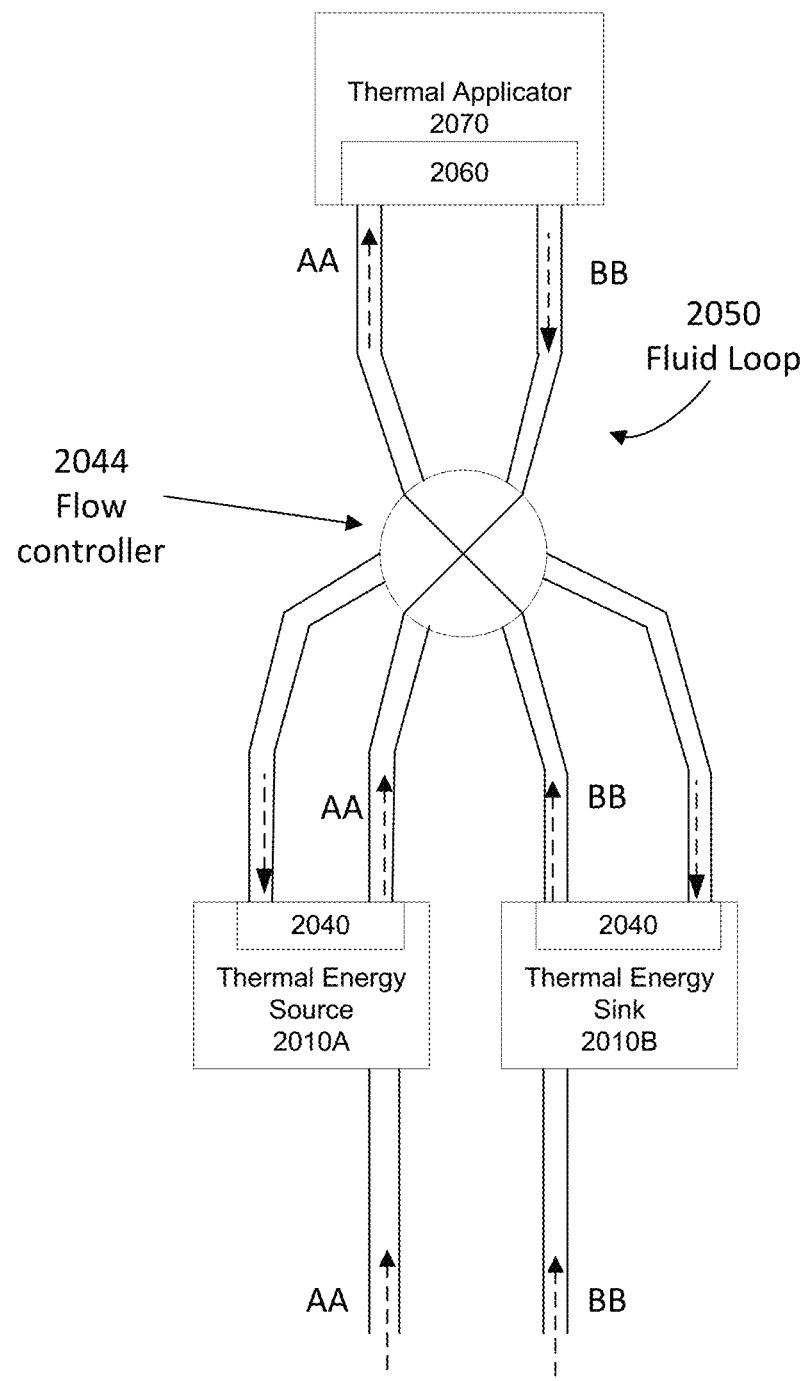
FIG. 13B is a schematic representation of a thermal neural modulation system, according to an embodiment.

In some embodiments, a thermal modulation system can include adaptations to permit rapid switching between heating and cooling while administering thermal neural modulation to a patient. The system 2000 illustrated in FIG. 13B shows an example implementation of a rapidly switchable thermal modulation system. The system 2000 includes a thermal energy source 2010A, thermal energy sink 2010B, a fluid loop 2050, flow controllers 2044, a thermal applicator 2070 configured to be applied to a tissue proximal to a target nerve that is to be treated. The thermal energy source 2010A and the thermal energy sink 2010B can each be implemented using any approach described herein. The system 2000 also includes a pump (not shown) to pump thermally conducting fluid through the fluid loop 2050, and a system controller (not shown). The system 2000 may also include first heat exchangers 2040 interfacing between the source 2010A and the fluid loop 2050, and between the sink 2010B and the fluid loop 2050. The system 2000 may also include a second heat exchanger 2060 interfacing between the fluid loop 2050 extending into the thermal applicator 2070. In some embodiments, the system 2000 can include optional thermally conductive and/or thermally insulating material TCM/TIM.

The flow controller 2044 can be any suitable component capable of directing fluid flow in a desired direction including valves, stop cocks, and/or the like. The flow controller 2044 can be operatively coupled to the system controller such that the system controller can send command to change a state of the flow controller 2044 and control the operation of the system 2000.

The fluid loop 2050 is configured such that pumped fluid can be directed to the thermal applicator 2070 via a path AA interfacing with the source 2010A such that the fluid may be heated before reaching the applicator 2070, or via a path BB interfacing with the sink 2010B such that the fluid may be cooled before reaching the thermal applicator 2070. The flow controller 2044 is positioned such that controlling the state of the flow controller 2044 can direct flow of pumped fluid to either the path AA interfacing with the thermal energy source 2010A or the path BB interfacing with the thermal energy sink 2010B.

In use, the flow controller 2044 can be at a closed state such that both paths AA and BB are closed. The system controller can send a command to transition the flow controller 2044 from the closed state to a first open state in which the path AA interfacing with the thermal energy source 2010A is open and the path BB interfacing with the heat sink 2010B is closed. At this state the pumped fluid can flow via the path AA interfacing with the first heat exchanger associated with the thermal heat source 2010A through the flow controller 2044 and via the path AA. The heat exchanger transfers thermal energy from the source 2010A to the fluid in the portion of the path AA interfaced with the heat exchanger to heat the fluid to a predetermined temperature. The heated fluid flows via the fluid loop 2050 to the applicator 2070 and is used to provide thermal modulation via providing a heat block to the tissue and the target nerve to a desired temperature and/or for a desired time period. In some implementations, the fluid traversing through the fluid loop 2050 and through the thermal applicator 2070 can be recirculated via a pump (not shown) to be retreated by the thermal energy source 2010A and re applied via the thermal applicator 2070.

The time period to provide heating may be precisely monitored by the system controller. When the desired time period for the heating elapses, the system controller can send a command to the flow controller 2044 to transition the flow controller 2044 from a first open state to a second open state where the path BB interfacing with the thermal energy sink 2010B is open and the path AA interfacing with the thermal energy source 2010A is closed. At this state the flow controller 2044 permits or directs pumped fluid to flow through the path interfacing with the heat exchanger that draws thermal energy from the fluid to the sink 2010B thereby cooling the fluid to a predetermined temperature before reaching the applicator 2070. The cooled fluid can be directed to the thermal applicator 2070 to apply thermal modulation to the tissue and the nerve via a cooling block for a predetermined time period, as described herein. After the desired time is lapsed the system controller can send a command to return the flow controller 2044 to a closed state and/or the pump to an inactive state such that thermal modulation is ceased.

Figure 14A:
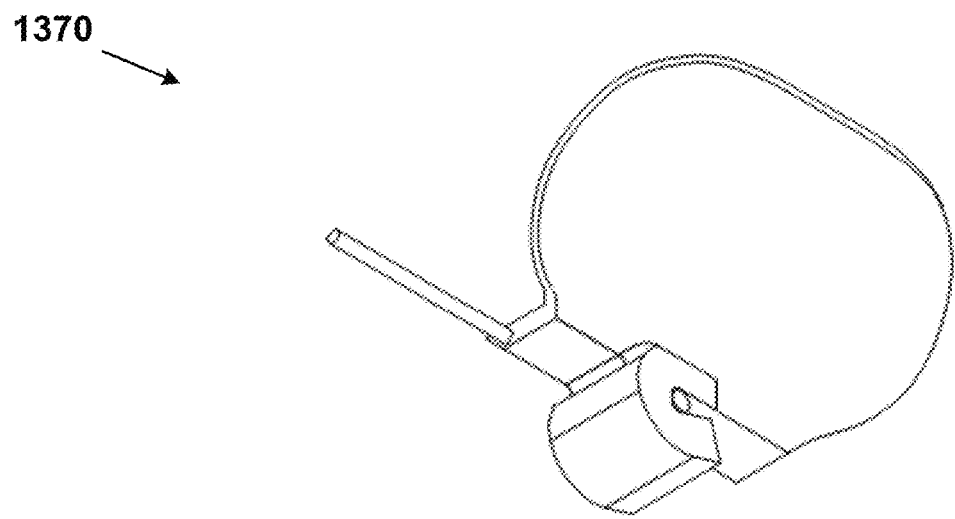
FIGS. 14A-B are illustrations of a thermal applicator, according to an embodiment.
Figure 14B:
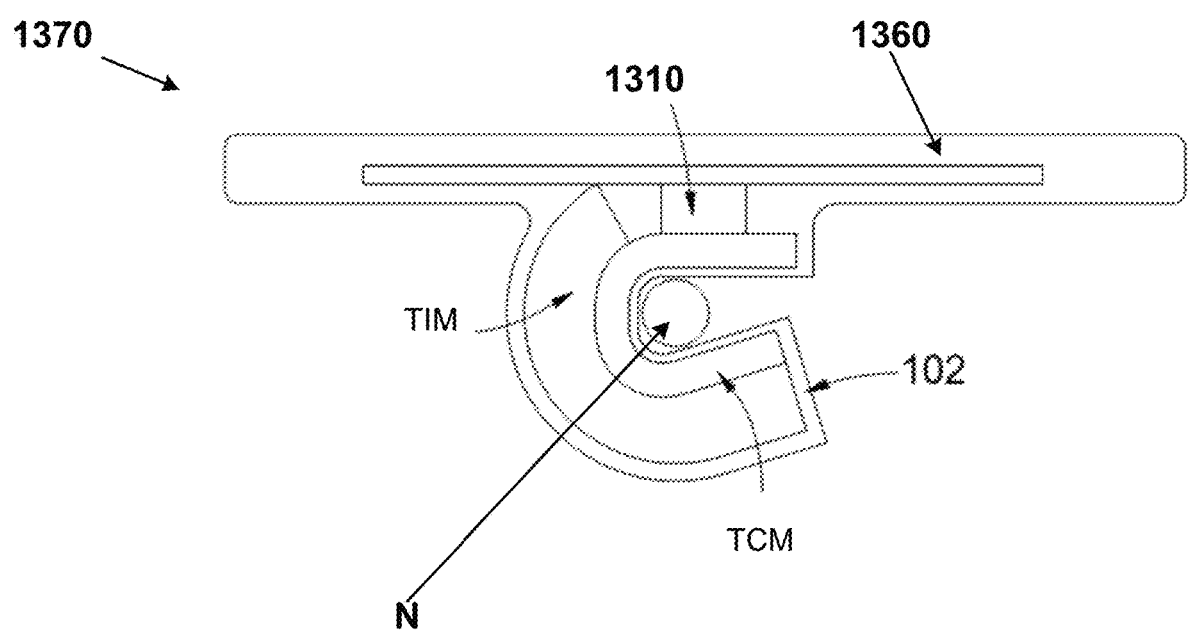

As described above, thermal applicator 170 can be implemented in many ways, depending on the desired application. Another embodiment of a thermal applicator is shown in FIGS. 14A and 14B. Thermal applicator 1370 is configured as an implantable thermal applicator, which can be implanted in the tissue of the subject near or partially surrounding a target nerve N. FIG. 14B shows details of the implantable components of the thermal applicator 1070 located on or near a nerve. The thermal modulation system associated with the thermal applicator 1370 includes TESS 1310 (which in this example may be a TEC) to provide thermal energy that is transferred via heat exchanger 1360 along a TCM to heat or cool the nerve N. In some embodiments, in portions of the device not adjacent to the nerve, insulating material TIM surrounds the conductive material TCM to confine thermal energy transfer to the nerve and avoid transfer of thermal energy to non-target nerves. In some embodiments, the thermal applicator 1370 including the heat exchanger 1360, the TCM/TIM can be constructed in a suitable shape to make optimal contact with the nerve N, including the shape of a horseshoe, a C-shape, a bowl, and a semi-circle, as illustrated, by example, in FIGS. 14A and 14B.

In some embodiments, thermal applicator 1370 and associated components of the thermal modulation system that are intended to be implanted in the subject may be coated with, or constructed of, a biocompatible material, such that the implanted components may be implanted on or near the nerve for a duration of time sufficient for treatment without triggering a significant immune response. The biocompatible material may be a gel, aerogel, hydrogel, microparticles, dermal or other filler, injectable slurry or other material that does not produce a significant immune response. A biocompatible coating may be present on the thermal modulation system prior to implantation or may be coated on at least a portion of the system following implantation. The biocompatible material may be biodegradable and may degrade over a finite period of time. The degradation may not occur in vivo or may only slowly degrade over an extended amount of time, such as a period of months or years, in vivo.

Another embodiment of a thermal applicator is shown in FIGS. 15A to 15F. Thermal applicator 1470 of the thermal modulation system (not shown) uses a fluid loop to deliver thermal modulation and may be constructed in any suitable shape including the shape of a horseshoe, a C-shape, a U-shape, a bowl, and a semi-circle, as illustrated by example in FIG. 15A. The thermal applicator 1470 may be implanted at or near a nerve to provide heating and/or cooling, such that the nerve may experience reversible blockade. In one embodiment, the thermal applicator 1470 is U-shaped and extends around the nerve. The material of the thermal applicator 1470 may be constructed of any material, the surface of which is biocompatible when implanted at or near a nerve. In one embodiment, the thermal applicator 1470 is constructed of gold. The thermal applicator 1470 may be produced by 3D printing, injection molding, commercial casting processes, or any other suitable production technique.

The thermal applicator 1470 may be sized such that it scales with the diameter of the nerve or neurovascular bundle, such that the thermal applicator 1470 may extend near or around the nerve or extend a particular distance along the nerve, as desired for reversible blockade of the nerve. In one embodiment, a U-shaped thermal applicator 1470 surrounds a nerve on three out of four sides from a planar on-axis view, as shown in FIG. 15B, such that a minimal temperature variation may be maintained throughout at least a section of the nerve. The cross sectional parameters of a thermal applicator 1470 may thus be determined by the diameter of the nerve it may target for reversible blockade. The thermal applicator 1470 may be of millimeter-scale dimensions including, for instance, 4 mm by 3 mm by 5 mm thermal applicator 1470 for a 2 mm diameter and 2 mm axial section of a nerve. In some embodiments the U-shaped thermal applicator 1470 is placed facing the nerve such that the opening of the "U" is relatively close to the nerve to direct thermal energy in the direction of the nerve.

Figure 15A:
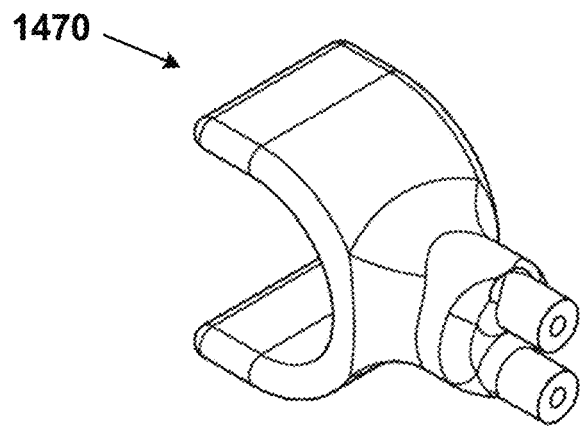
FIGS. 15A-E are illustrations of a thermal applicator, according to an embodiment.
Figure 15B:
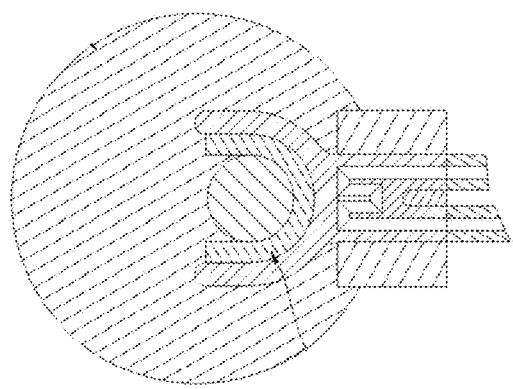
Figure 15C:
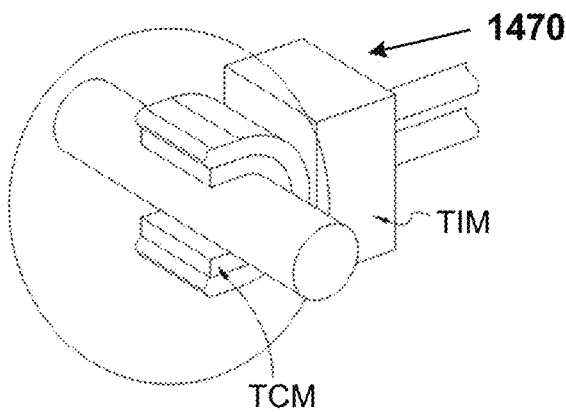
Figure 15D:
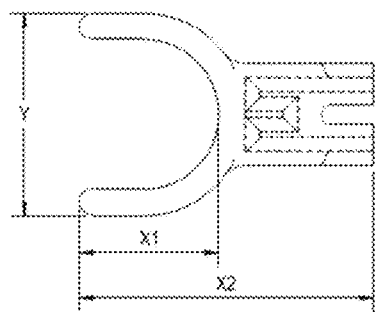
Figure 15E:
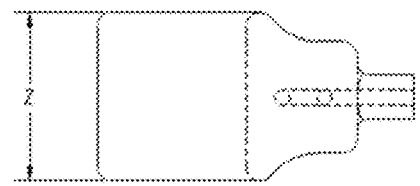

In one embodiment, the size of the thermal applicator 1470 may be calculated from the dimensions of a target nerve according to Equations (1)-(4) with reference to the dimensions in FIGS. 15D-15E:

$$X1 = D + 1.5 \text{ mm} \tag{1}$$

$$X2 = X1 + 2 \text{ mm} \tag{2}$$

$$Y = D + 2 \text{ mm} \tag{3}$$

$$Z = Zn + 1.5 \text{ mm} \tag{4}$$

In Equation (1), X1 is a dimension of a U-shaped thermal applicator 1470 as shown in FIG. 15A. The diameter of a nerve is D. In Equation (2), X1 is a dimension of a U-shaped thermal applicator 1470 as shown in FIG. 15D. In Equation (3), Y is a dimension of a U-shaped thermal applicator 1470 as shown in FIG. 15D. In Equation (4), Z is a dimension of a U-shaped thermal applicator 1470 as shown in FIG. 15E. The axial length of a target nerve is Zn.

In some embodiments, the thermal energy probe may further include at least one fluid channel that is part of a fluid loop (not shown), such that heated fluid or cooled fluid may enter the thermal applicator 1470 and transfer thermal energy to the thermal applicator 1470 for heating or cooling the nerve. The fluid channel 1406 may have a diameter of about 0.3 mm or any diameter suitable for a snug fit of tubing. The fluid channel 1406 may be about 1.5 mm in length, or any other suitable length such that tubing may be securely held in place and such that thermal applicator 1470 size is minimized for implantation. The at least one fluid channel may provide an inlet and an outlet for the heated fluid or cooled fluid and may be located on the back of the thermal applicator 1470, or in any suitable location as to provide the heated fluid or cooled fluid to the thermal applicator 1470. The heated fluid or cooled fluid may be water, saline, or any other suitable fluid such that the fluid may be heated or chilled to a temperature required to heat or cool a nerve without the fluid vaporizing or becoming frozen. The cooled or heated fluid may exit the thermal applicator 1470 through at least one fluid channel which may serve as an outlet. In one embodiment, the cooled or heated fluid may be carried through the at least one fluid channel using tubing, wherein the tubing is flexible, insulated, and conforms to the dimensions of the at least one fluid channel for a snug fit.

In some embodiments, the thermal applicator 1470 further includes a coating of conductive gel, or thermally conductive material TCM on a surface that is nearest the nerve as shown in FIGS. 15B-15C to provide more even heating and cooling of the target section of nerve. In some embodiments, the thermal applicator 1470 may include an insulation backing, or thermally insulating material TIM on at least one surface of the thermal applicator 1470 that does not interface with a nerve. The thermal applicator 1470 with insulation backing TIM is shown in FIGS. 15B and 15C.

In some embodiments, the placement of a thermal applicator 1470 implanted at or near a nerve for reversible blockade can be guided by ultrasound or x-ray (fluoroscopy) and inserted through an incision using an applicator or other such suitable device for placing the thermal applicator. In some implementations, as described previously with reference to application of TIM, a thermally insulating gel, self-setting polymer, foam, plastic or other biocompatible polymer or composite material may be injected or inserted into the body such that the gel or material may direct or contain the heating and/or cooling of the thermal energy system 1400 by decreasing thermal conductivity and the rate of thermal energy transfer in the area outside of the desired area of affect around a device and the target nerve.

Figure 16A:
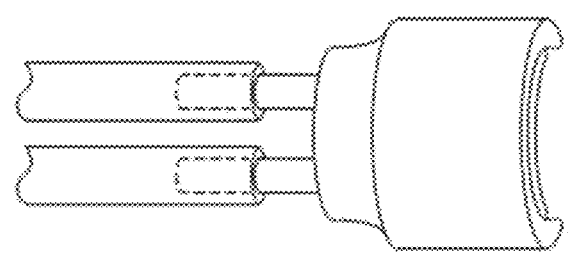
FIGS. 16A-B are illustrations of a thermal applicator, according to an embodiment.
Figure 16B:
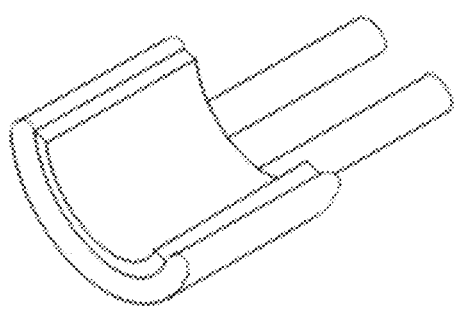

Another embodiment of a thermal applicator is shown in FIGS. 16A and 16B. Thermal applicator 1570 is implemented using a fluid loop to transfer thermal energy between a thermal modulation system (not shown) and a target nerve via the thermal applicator 1570. The thermal applicator 1570 can be substantially similar in structure and/or function to the thermal applicator 1470 except for the shape or conformation of the thermal applicator 1570 is in the form of a curve as indicated in FIGS. 16A and 16B.

As described above in connection with system 100, TESS 110 can have the thermal neural modulation functions of moderate heating and moderate cooling performed by separate components. FIGS. 17A-17C show a system 1600 that is a hybrid implementation including a wearable system of administering cooling to a target region and an implantable system of administering heating to a region of tissue of a patient. In the embodiment shown in FIGS. 17A-17C, system 1610 includes an implantable thermal applicator 1670A that mediates delivery of thermal energy to and/or from a target nerve. In some embodiments, the thermal energy can be from a resistively heated source. In this implementation, the system 1600 includes a rigid portion 1611 and a flexible portion 1612. The flexible portion includes one or more thermal energy sources 1610A that are directly coupled to the thermal applicator 1670A, which absorbs inductive energy from the external energy source and converts that energy into heat via resistive heating. The thermal applicator 1670A may be implanted for a time of about a few minutes in order to block a nerve or nerves during a medical procedure, for about a few hours or days, or for many years to treat chronic conditions or symptoms. In some embodiments, the resistively heated implant may include a thin, linear, and generally flexible portion 1612 coupled to the rigid portion 1611, as shown by means of example in FIG. 17A. The resistively heated implant may comprise rigid portions and flexible portions arranged in any suitable form. The rigid portion 1611 can include electronics (e.g., positive thermal coefficient resistor element, an inductive element, power control MOSFET, a microcontroller, passive electronics, etc.), as required for operation. The flexible portion 1612 may include thermal energy source 1610A, feedback sensors (e.g., temperature sensors) and optionally a PCB. The rigid portion 1611 may be overmolded with a harder (e.g., less porous) plastic or metallic material. For example, EX PEEK or titanium (titanium shell that is welded shut with an appropriate process such as laser welding) to permit the implant to be biocompatible. The SMT (surface mount technology) components, such as microcontroller, MOSFETs, etc may have to be included in the rigid portion 1611 that is overmolded to promote biocompatibility. Any contacts that may be accessible outside of the overmolded region may be formed using inert and/or biocompatible materials (e.g., gold contacts). The overmolding may be via a biocompatible coating. In some implementations, a biocompatible coating may be applied prior to implantation or following implantation.

In some embodiments, the system 1600 includes a system controller 1680, including a processor in communication with the thermal energy source 1610A. The system can include an external thermal energy sink. In some embodiments, a microcontroller within the resistively heated thermal energy source 1610A communicates with the system controller 1670B and, after receiving a secure enable signal from the system controller 1670B, determines temperature set points, duration of heating, controls power flow to the at least one heating element, and directs other functions of the thermal energy source 1610A, as required to reversibly block the target nerve(s). The microcontroller may be utilized to maintain a low power level and to direct the continued monitoring of the temperature during a cooling of a nerve. The microcontroller may be in continuous communication with the system controller 1670B to create a continuous feedback loop.

In some embodiments, the cooling of the target nerve(s) by the system 1600 may be externally applied by an external thermal energy sink 1610B implemented via an applicator portion of a cooling delivery device connected to an external chiller pump circulating cooled fluid. In some embodiments, the thermal energy sink 1610B and/or the system controller 1670B can be contained within a wearable device such that the wearable device may be positioned at a target location, wherein the target location is against the skin that covers an implanted thermal energy source 1610A via a resistively heated implant and its target nerve, as shown in FIG. 17C.

The wearable device may include an applicator 508 that is attached to a patch, headband, strap, band, or any such structure or means of fastening or containing an applicator portion of the system 1600 including for example a highly viscoelastic or memory-foam-like material to increase uniformity of skin-surface contact and reduce likelihood of pressure points or hot-spots. The thermal energy sink 1610B, inductive power supply, and the system controller 1670B or a portion of it can be worn at the target location to provide thermal contact between the skin and the wearable device. The fastening structure (e.g., headband) may contain wireless power transmission components and equipment to facilitate electrical energy transfer to thermal energy source 1610A. The specific method of wireless power transfer may vary as appropriate to each use case. For example, in some implementations the headband can include transmit coils such that when an alternating current is passed through them a transmit coil in turn creates a magnetic field that is passed through the distance between the headband and the user, through the user's tissue, and to the implanted thermal energy source 1610A. Thermal energy source 1610A can include a receive coil that picks up this magnetic field and creates an electrical potential on the receive coil. The circuitry in the over molded portion 1611 of the system 1600 can include power management circuits and technology that harvest this electrical potential and use the electrical energy to power the control circuitry in the portion 1611 and/or the resistive heating elements in the portion 1612. In some embodiments, the system may use different wireless power technologies currently available or future technologies developed. Some examples include Qi wireless standard, coupled coil technology, resonate circuits, and other such technologies that are suitable to transmit the electrical energy through the user's tissue.

The applicator 508 may be coupled to the thermal energy sink 1610B and an external chiller pump 1680 by a cooling fluid path via a coupling portion 1697, which may be insulated, such that chilling fluid may be directed from the external chiller pump to the applicator 508 at a target location and recycled fluid may be to the external chiller pump to be chilled. In some embodiments, the thermal energy sink 1610B may be implemented by a Peltier cooling system, such that recycled fluid may be chilled to become chilling fluid for reuse. In some implementations, the only significant difference between the recycled fluid and the chilling fluid may be the temperature of each, and the recycled fluid and chilling fluid may be converted between each other by means of altering their temperatures. The composition of both the recycled fluid and the chilling fluid may be saline or any other suitable fluid such that the fluid may be chilled to a temperature required to cool a nerve without the fluid becoming frozen. In a preferred embodiment, the chilling fluid may be chilled to a temperature at or slightly above about 0° C., such that a nerve may be cooled to a temperature as directed by the system controller 1670B.

EXAMPLES

Rationale

A study was conducted to understand the heat and cold interaction on conduction block of unmyelinated C-fibers and to develop a safe method for thermal block of C-fiber conduction. In 7 cats under α-chloralose anesthesia, conduction block of C-fibers by cooling (5-35° C.) or heating (45° C.) a small segment (9 mm) of the tibial nerve was monitored by recording the C-fiber evoked potentials. Reproducible cold block was observed at 5-15° C. before any heating.

After heating the nerve at 45° C. for 5-35 minutes the cold block temperature was shifted from 5-15° C. to 15-25° C. The room temperature (15-25° C.) block lasted for at least 30-100 minutes while the conduction of C-fibers was recovered about 80% at 35° C. This study discovered a novel thermal method to block mammalian unmyelinated C-fibers at room temperature, providing the opportunity to develop a thermal nerve block technology to suppress pain of peripheral origin. The interaction between heat and cold effects on C-fiber conduction indicates a possible interaction between different temperature sensitive channels known to be presented in the mammalian unmyelinated C-fibers.

From previous studies, it is known that nerve conduction can be completely blocked by locally cooling the nerve below 5° C. or by heating above 50° C. (Jia and Pollock 1999; Klumpp and Zimmermann 1980: Paintal 1965: Stecker and Baylor 2009). However, these extremely low or high temperatures can cause nerve damage during a long duration application (Hoogeveen et al. 1993: Vujaskovic et al. 1994). Therefore, clinical application of cold/heat block to treat chronic disorders currently remains elusive. Experiments indicated that the cold temperature for complete block of myelinated motor A-fibers can be increased from 5° C. to about 15° C. after a reversible and brief heating. The room temperature (15° C.) is known to be safe for the nerve. A safe thermal block of nerve conduction can have a wide range of clinical applications to treat many chronic disorders. For example, chronic pain is caused by sensitization and overactivity of nociceptive afferent C-fibers that can be blocked to relieve the pain (Cuellar et al. 2013: Soin et al. 2015). Obesity is associated with activity in the abdominal vagus nerve and partial block (suppression) of the abdominal vagus nerve can treat extreme obesity (Sarr et al. 2012). Overactivity in sympathetic nervous system can cause heart failure and suppression of splanchnic nerve activity can prevent heart failure (Floras 2009: Fudim et al. 2018). Blocking the pudendal nerve after spinal cord injury (SCI) can facilitate emptying the urinary bladder by relaxing the external urethral sphincter (Tai et al. 2004: Yang et al. 2014).

For clinical applications to treat chronic pain, block of unmyelinated C-fibers is required. However, it is still unknown if the cold temperature for complete block of unmyelinated C-fibers can also be increased from 5° C. to 15° C. after a reversible and brief heating. Therefore, in this study using cats the C-fiber evoked potentials are recorded from the tibial nerve to investigate the effects of heat/cold on axonal conduction of the unmyelinated C-fibers.

Experimental Setup

A total of 7 cats (4 female and 3 male, 2.8-4.2 kg, Marshall BioResources, North Rose, NY, USA) were used in this study. The animals were anesthetized by isoflurane (2-5% in oxygen) during surgery and maintained with α-chloralose anesthesia (65 mg/kg i.v. with supplementation as needed) during data collection. A pulse oximeter (9847 V, NONIN Medical, Inc., Plymouth, MN, USA) was attached on the tongue to monitor the heart rate and blood oxygen level. A tracheotomy was performed, and a tube was inserted to maintain the airway open. A catheter was inserted into right carotid artery to monitor systemic blood pressure. Another catheter was inserted into the left cephalic vein for saline and anesthetics administration. All incisions were closed by sutures at the end of surgery.

The left tibial nerve was exposed via an 8-10 cm incision along the inner side of the leg between the ankle and the knee. The nerve was dissected at the site below the knee to implant a tripolar cuff electrode (NC223pt: MicroProbe, Gaithersburg, MD) for recording evoked potentials, and then it was transected centrally to the cuff electrode.

Figure 18:
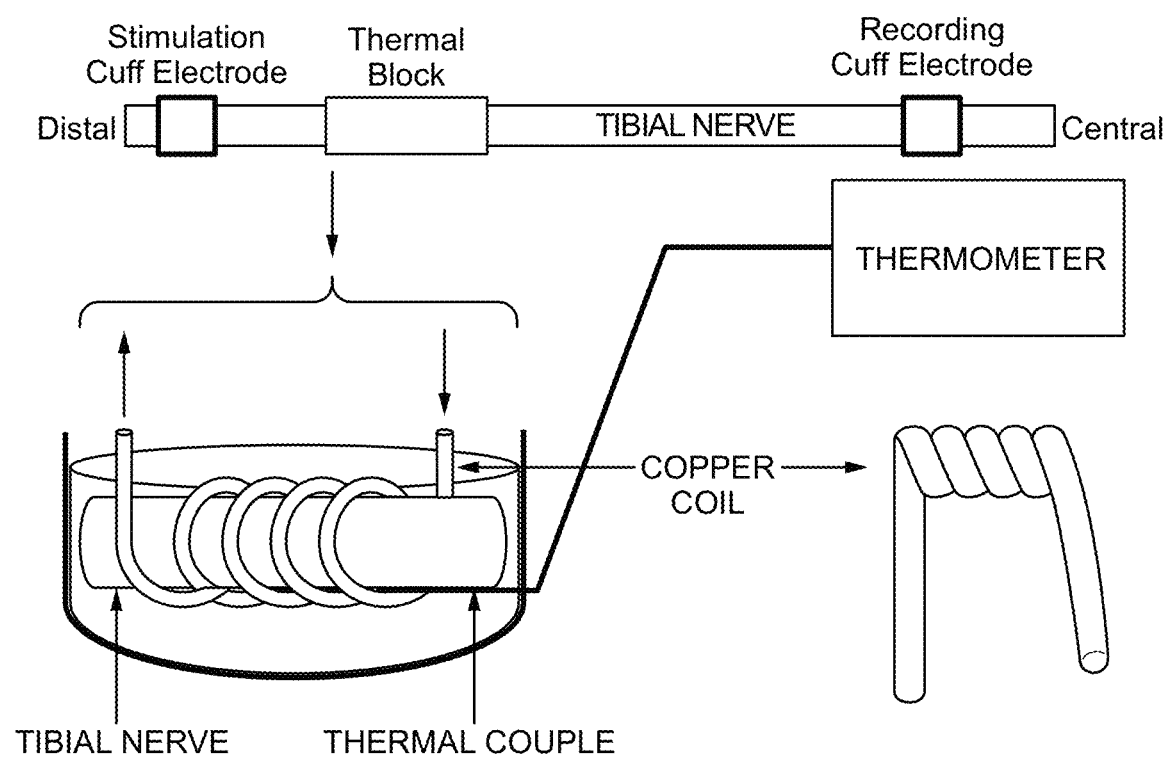
FIG. 18 is an illustration of an experimental setup to measure effect of temperature on nerve conduction, using a thermal modulation system according to an embodiment.

FIG. 18 is a schematic representation of the drawing of the experimental setup. As shown, the tibial nerve was cut distal to the stimulation site and central to the recording site. The nerve was passed through a coil of copper tubing for thermal block. The temperature inside the coil was changed by running water of different temperatures through the tubing. A thermocouple was placed in the center of the copper coil to record temperature. Electrical stimulation was applied to the nerve by the tripolar cuff electrode distal to the coil and the evoked potential was recorded by a bipolar cuff electrode central to the coil. The nerve, coil, and electrodes were all immersed in warm mineral oil.

The evoked potentials were amplified 60,000-200,000 times by an amplifier (P511, Grass Instruments, MA), sampled at 20 kHz by an analog-to-digital converter (PCI-6024E, National Instruments, TX), and saved in a computer running the LabVIEW program (National Instruments, TX). At the ankle, the nerve was dissected and transected distally to be passed through a small (9 mm long) coil (2 mm inner coil diameter) of copper tubing (#8117, K&S Precision Metals, Inc., Chicago, IL) (FIG. 18). One end of the copper tubing (outside diameter 1.57 mm and inside diameter 0.36 mm) was connected to syringe via a plastic tube for manually infusing cold (0-10° C.) or hot (48-50° C.) water to locally cool or heat the nerve segment in the coil. The temperature inside the coil was monitored by a thermocouple with the sensor tip positioned in the center of coil (FIG. 18). The coil fit closely around the nerve and the thermocouple, so that the thermocouple tip was in contact with both the nerve and the coil. The thermocouple was connected to a commercially available thermometer (Model 4482, Control Company, Friendswood, TX) for displaying the temperature (+0.1° C. resolution). The mean temperature was maintained within +1° C. of the targeted temperature by manually adjusting the infusion rate (Zhang et al. 2016). A bipolar stainless-steel hook electrode was placed on the nerve distal to the copper coil (FIG. 18) to test whether local temperature change inside the coil could block the conduction of C-fiber action potentials evoked by electrical pulses (10-44 V, 1 ms pulse width) generated by a stimulator (S88, Grass Technologies, West Warwick, RI). The distance between the stimulation electrode and the recording electrode was about 45-65 mm. The nerve, coil, and electrodes were all immersed in the warm mineral oil pool formed by retracting the skin flaps using sutures. The oil pool temperature (35-37° C.) was monitored by another thermometer and maintained during the experiment by a heating lamp and by adding warm oil as needed.

Experimental Protocol

In each experiment, the nerve was first cooled sequentially to temperatures of 35, 30, 25, 20, 15, 10, and 5° C. in −5° C. steps. At each step, the temperature was maintained for 20-30 seconds to record the C-fiber evoked potentials. The cooling effect was tested 2-3 times to confirm the reversibility and repeatability. Then, the nerve was heated to 45° C. for 5-10 minutes. During the heating, the C-fiber evoked potential was recorded every minute to monitor the heating effect on nerve conduction. After the heating, the nerve was cooled again to different temperatures (35-5° C. in −5° C. steps) to examine if the complete cold block temperature was increased from ≤5° C. to a temperature between 10 and 20° C. The complete cold block temperature is defined as the temperature at which the amplitude of C-fiber evoked potentials was reduced to <20% of the control amplitude that was measured at 35° C. before the heating. If the complete cold block temperature was not increased, the 45° C. heating (5-10 minutes) was repeated until the amplitude of C-fiber evoked potentials at 10-20° C. was reduced to <20% of the control. Then, the heating effect on cold block was monitored every 5-30 minutes for 30-100 minutes in different animals by repeatedly cooling the nerve to 35-5° C. in −5° C. steps and recording C-fiber evoked potentials at each temperature step.

Data Analysis

To determine the temperature effect on C-fiber conduction, the amplitude, duration, and peak latency of the C-fiber evoked potentials were measured at different temperatures and normalized to the control values measured at 35° C. before heating/cooling. The results obtained from different animals under the same experimental conditions were averaged and reported as mean±standard error. Statistical significance ($p<0.05$) was detected by repeated measure ANOVA followed by Dunnett (one-way) or Bonferroni (two-way) multiple comparison.

Results

Conduction Block of Unmyelinated C-Fibers by Local Cooling or Heating

The conduction velocity of unmyelinated C-fibers in the tibial nerve is 0.75±0.02 m/s (0.67-0.85 m/s, N=7) that is measured by the peak latency of the C-fiber evoked potentials. When the nerve is cooled from 35° C. to 5° C., the amplitude of the C-fiber evoked potentials is gradually reduced but the duration and peak latency are gradually increased as shown in FIG. 19A-D. Evoked potentials induced by stimulation of C-fibers in the tibial nerve when a small segment of the nerve between the stimulation and recording electrodes is cooled to different temperatures (5-35° C.) is shown in FIG. 19A. The mean conduction velocity is 0.7 m/s measured by the peak latency of the evoked potential at 35° C. Stimulus pulse: 28 V, 1 ms. FIG. 19B shows the amplitude, FIG. 19C the latency, and FIG. 19D the duration of the evoked potentials indicating the change with temperature, obtained from 7 cats. Mean conduction velocity is 0.75±0.02 m/s. Stimulus pulses evoking the responses shown are 10-44 V delivered for 1 ms. The symbol * indicates significantly ($p<0.05$) different measured values from that measured at 35° C. tested using repeated measure ANOVA.

Complete block of C-fiber conduction is achieved at 5° C. in 5 cats (FIG. 19A), but less than 5° C. (2-3° C.) is required in 2 cats (shown in the control in FIG. 21A). On average the amplitude of C-fiber evoked potentials is significantly ($p<0.05$) reduced starting from 15° C. and at 5° C. it becomes <20% of the control value measured at 35° C. After the cooling, the C-fiber conduction is fully recovered once the temperature is increased to >25° C.

Figure 20A:
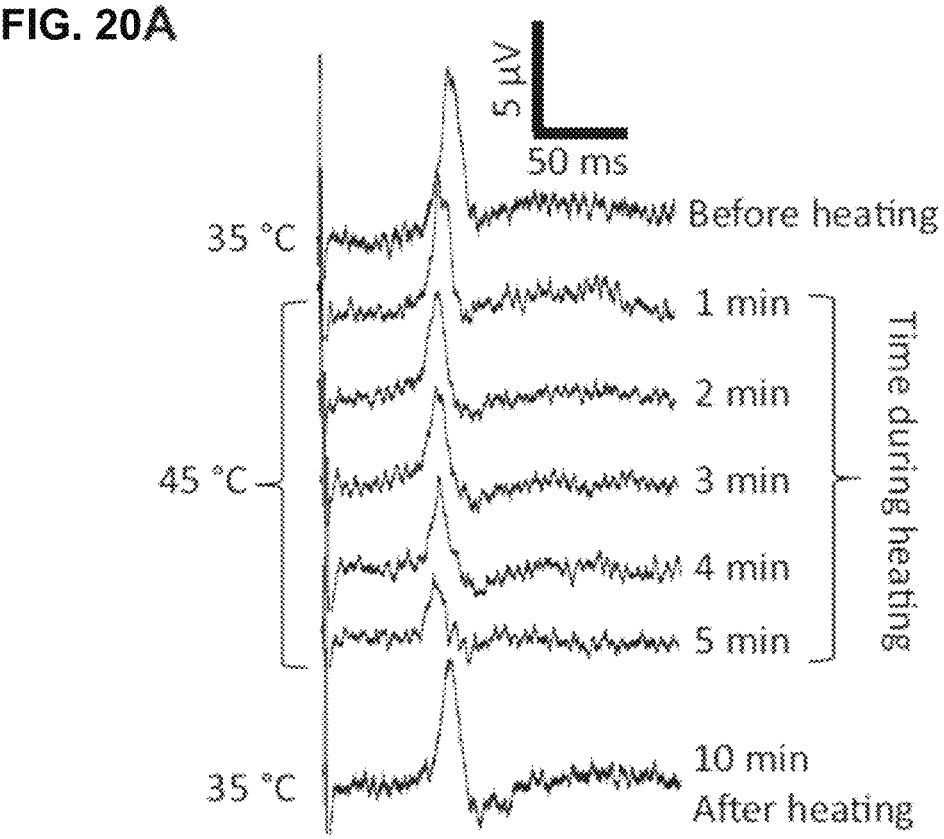
FIG. 20A-20B show physiological traces and analyses indicating effects of temperature on nerve conduction, using a thermal modulation system according to an embodiment.
Figure 20:
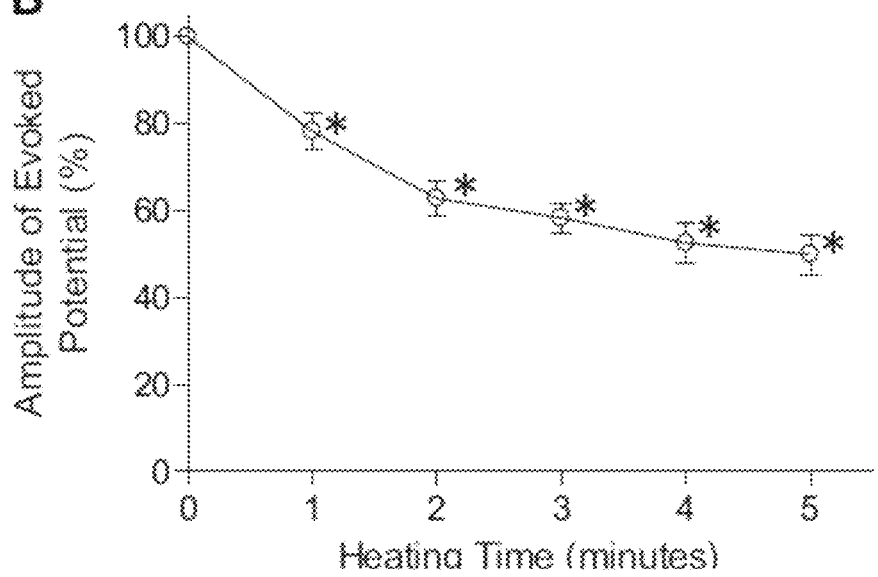

When the nerve is heated to 45° C. and maintained at this temperature, the amplitude of C-fiber evoked potentials is gradually reduced with heating time but the duration and peak latency are not significantly changed. FIG. 20A shows the effect of 45° C. heating on C-fiber axonal conduction as indicated by the evoked potentials before, during, and after 5 minute heating at 45° C. in a cat. The mean conduction velocity is 0.76 m/s at 35° C. Stimulus pulse used to evoke the potentials was 44 V for 1 ms.

FIG. 20B shows the amplitude of evoked potentials over an aggregate of nerves and cats. The amplitude decreases during the heating as observed in 7 cats. The symbol * indicates significantly ($p<0.05$) different from the amplitude before heating at 0 minute tested using repeated measure ANOVA. After 5-minute heating, the average amplitude of C-fiber evoked potentials is significantly ($p<0.05$) reduced to about 60% of the control value measured before the heating (FIG. 20B). At 10 minutes after the heating is terminated, the amplitude of C-fiber evoked potentials at 35° C. is recovered to about 70% of the control (shown in the last trace in FIG. 20A).

Local Heating Shifted Cold Block Temperature from 5-15° C. to 15-25° C.

The temperature for cold block of C-fiber conduction is increased after a brief heating at 45° C. To increase the cold block temperature, 45° C. heating (5-50 minutes) is applied once or multiple times in different cats. Table 2 shows the total heating time, the increased temperature for a complete cold block, and the maximal observation duration to monitor the post-heating effect in each animal. After heating the tibial nerve at 45° C. for an accumulative time of 5-35 minutes in different cats, the complete cold block temperature is increased from ≤5° C. to 10-20° C. (Table 1 and FIG. 21A).

Figure 21A:
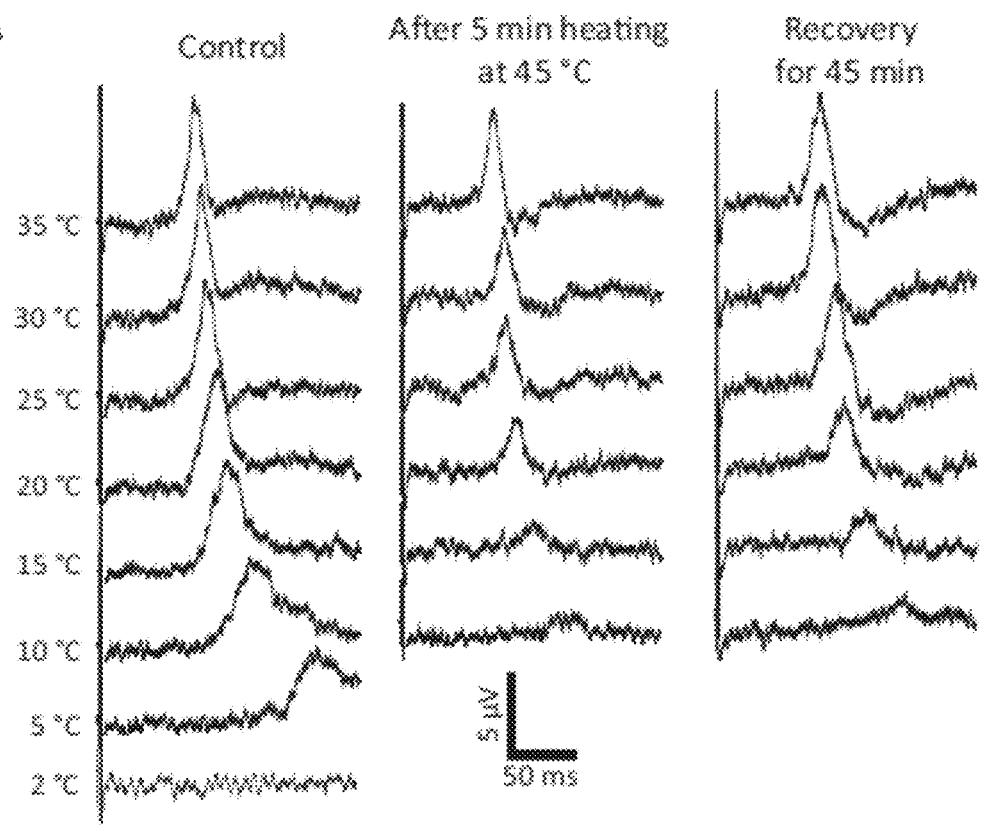
FIG. 21A-21B show physiological traces and analyses indicating effects of temperature on nerve conduction, using a thermal modulation system according to an embodiment.
Figure 21B:
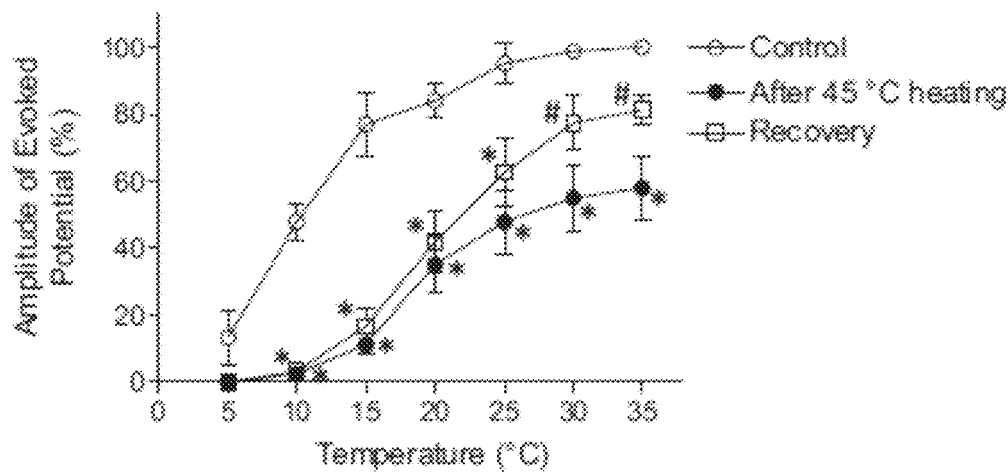

As shown in FIG. 21A, evoked potentials in a cat show that a temperature below 5° C. is required to block C-fiber conduction, but the temperature is increased to 10-15° C. by 45° C. heating of the nerve for 5 minutes. The block effect at 10-15° C. lasts for at least 45 minutes while the nerve conduction at 35° C. is largely recovered. Only minimal nerve conduction is evident in C-fibers at 15° C. even after 45 minutes of recovery, indicating slower recovery of function than previously tested Aβ-fibers that recover motor function within about 30-40 minutes of recovery. The mean conduction velocity is 0.76 m/s at 35° C. The stimulus pulse used to evoke potentials was 44 V, 1 ms. FIG. 21B shows summary results obtained from 7 cats, after 5-35 minute heating at 45° C. the temperature for complete block of C-fiber conduction increased from 5° C. to 15° C. This block effect is maintained for at least 30-100 minutes while on average 80% of nerve conduction is recovered at 35° C. The symbol * indicates significantly ($p<0.05$) different from control. The symbol # indicates significantly (p<0.05) different from the amplitude after 45° C. heating tested using Repeated measure ANOVA.

Within 5-10 minutes after terminating the 45° C. heating, the average amplitude of C-fiber evoked potentials at 35° C. is significantly (p<0.05) reduced to about 60% of control and a complete block (<20% of control) can be achieved at 15° C. instead of 5° C. (FIG. 21B). After monitoring the post-heating effect for 30-100 minutes in different cats (Table 1), the amplitude of C-fiber evoked potentials at 30-35° C. is significantly (p<0.05) recovered to about 80% of control, but the amplitude at temperatures below 25° C. is not recovered (FIG. 21B). ANOVA was used.

Figure 22A:
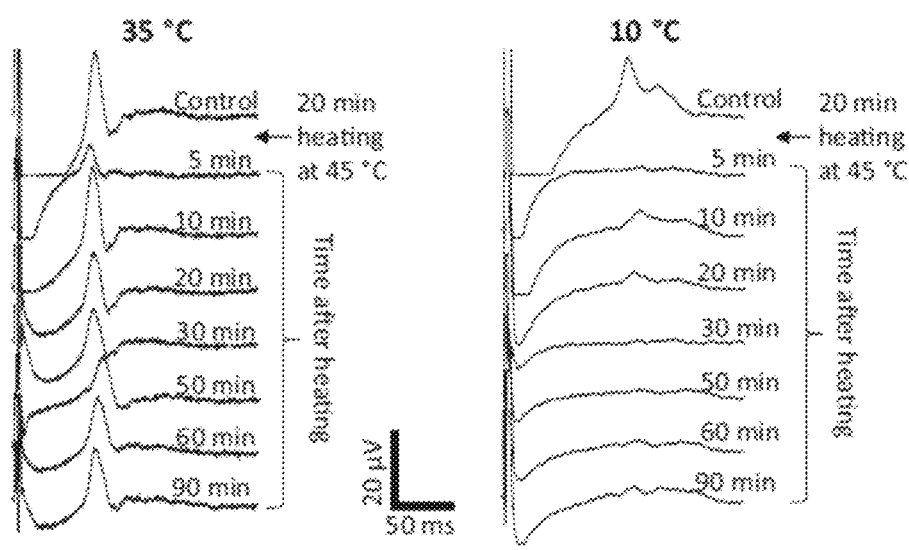
FIG. 22A-22B show physiological traces and analyses indicating recovery from effects of temperature on nerve conduction, using a thermal modulation system according to an embodiment.
Figure 22B:
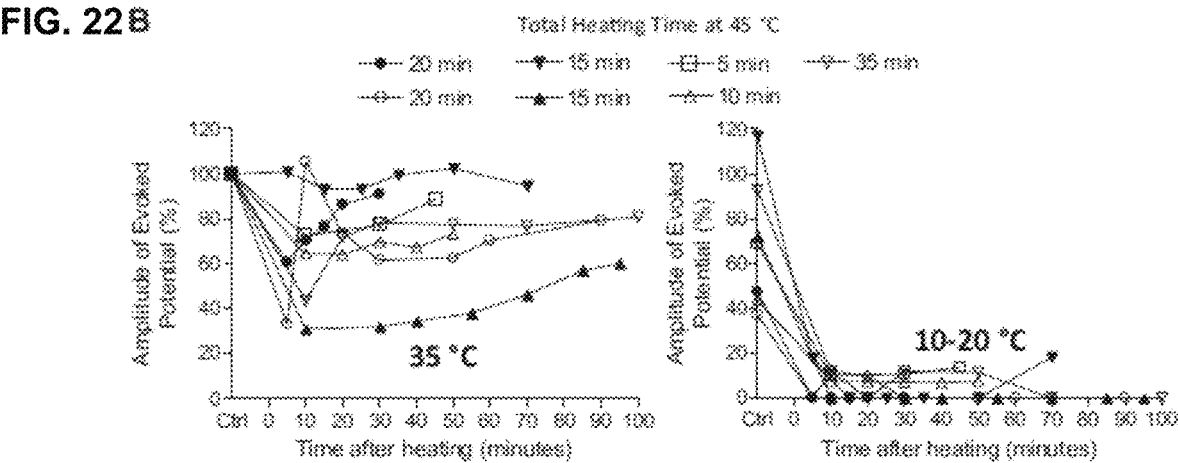
Figure 23A:
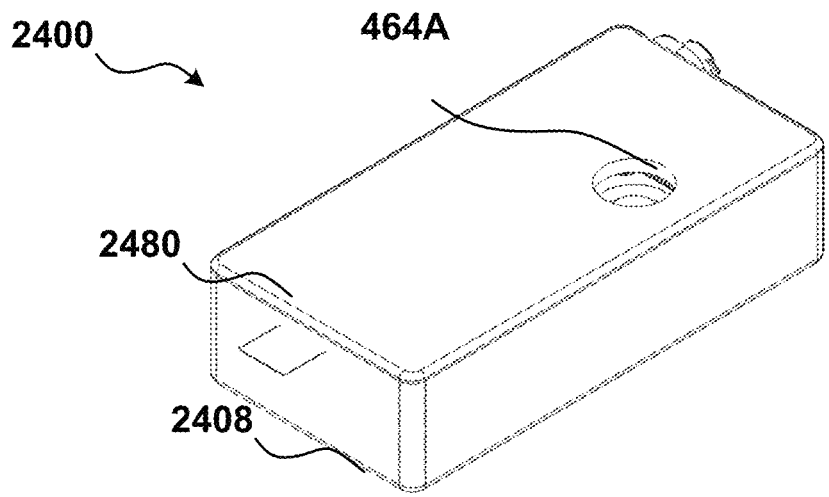
FIG. 23A-23B are schematic illustrations of a perspective view and a side view of a system controller of a thermal neural modulation system, according to an embodiment.
Figure 23B:
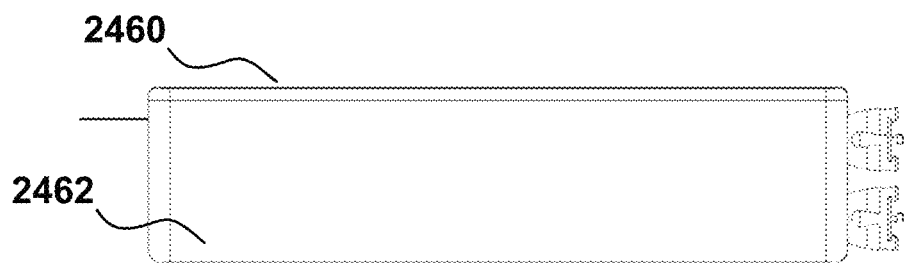
Figure 23C:
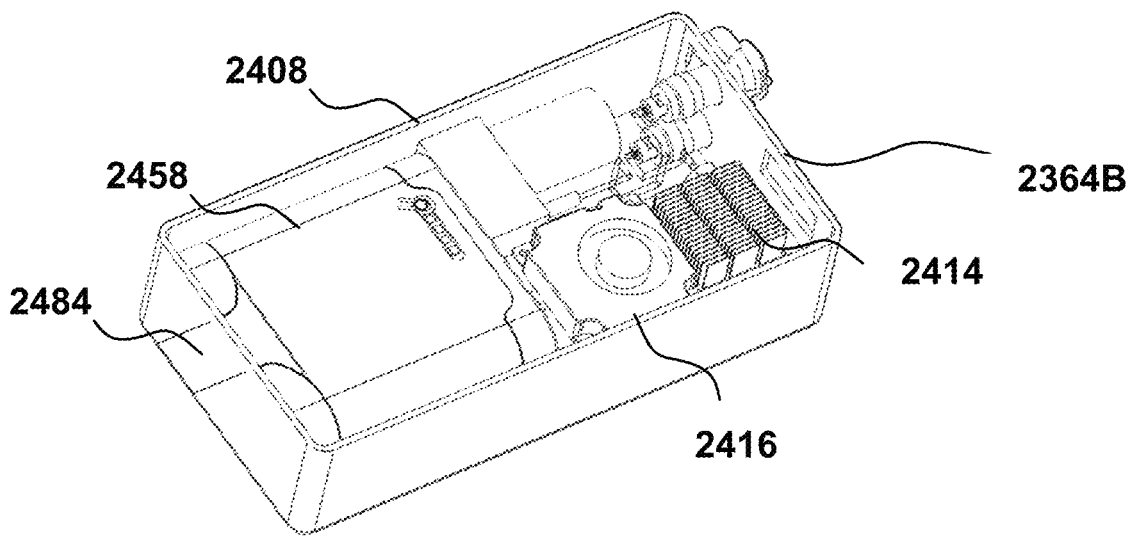
FIG. 23C is a schematic illustration of system controller of FIG. 23A with the top portion of the housing removed.
Figure 23D:
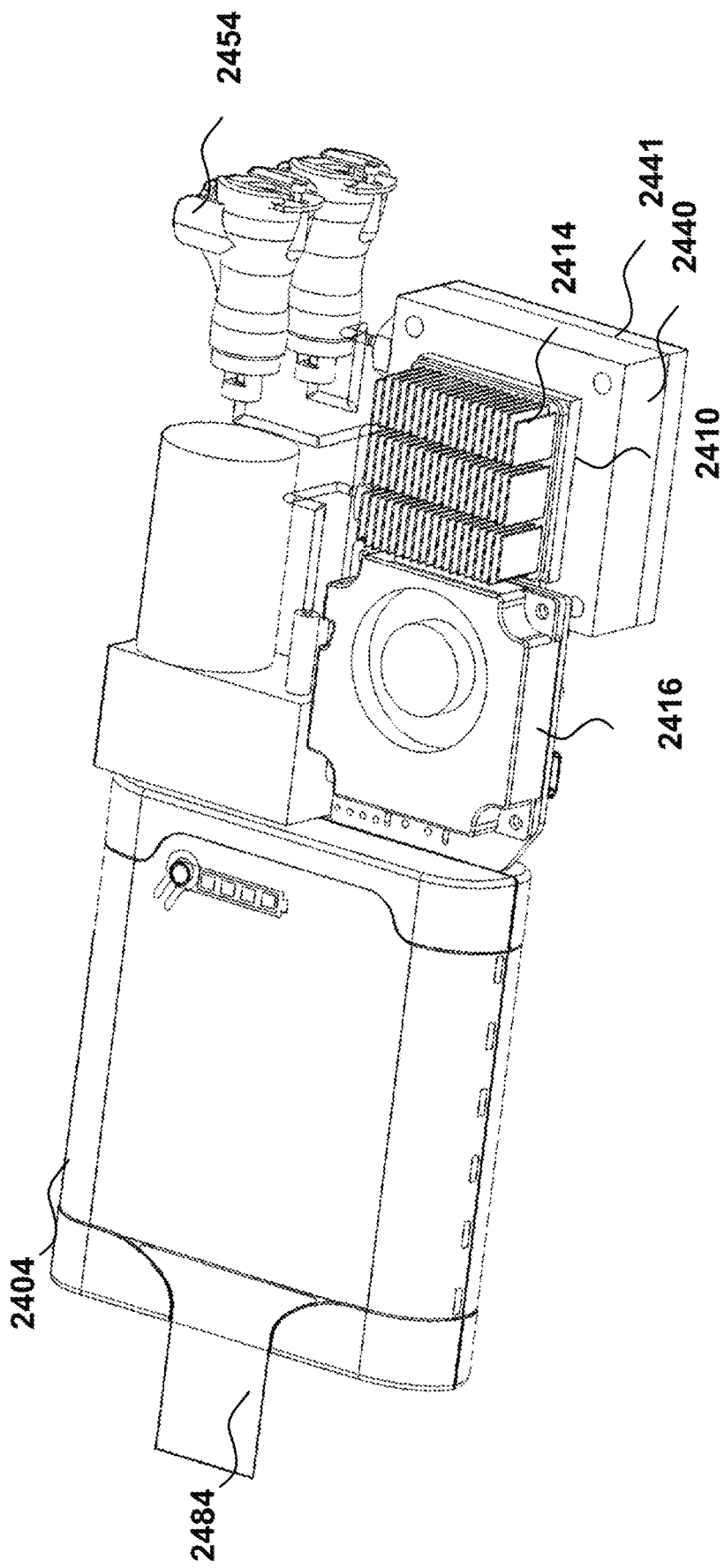
FIG. 23D is a schematic illustration of components of the system controller of FIG. 23A with the housing removed.

FIG. 22A shows in a cat the amplitude recovery of C-fiber evoked potentials at 35° C. but no recovery at 10° C., while FIG. 22B summarizes the results from every animal. Therefore, the 45° C. heating shifted the cold block temperature from 5-15° C. to 15-25° C. (FIGS. 21A, 21B) and this effect lasted for at least 30-100 minutes (FIGS. 22A, 22B).

TABLE 2

The total heating duration, complete block temperature, and observation duration in different cats.

| Cat # | Total Heating Duration (min) | Complete Block Temperature (° C.) | Observation Duration (min) |
|---|---|---|---|
| 1 | 20 | 15 | 30 |
| 2 | 20 | 10 | 90 |
| 3 | 10 | 10 | 50 |
| 4 | 15 | 20 | 95 |
| 5 | 35 | 15 | 100 |
| 6 | 5 | 15 | 45 |
| 7 | 15 | 15 | 70 |

DISCUSSION

This study using tibial nerves of cats shows that the temperature for a cold block of unmyelinated C-fibers can be increased to room temperature (15-25° C.) after a brief heating at 45° C. (FIGS. 21A, 21B). The room temperature block can last more than 100 minutes while the nerve conduction is largely recovered at 35° C. (FIGS. 22A, 22B). The room temperature (15-25° C.) is safe to the nerve and the effect of brief 45° C. heating is quickly about 80% reversible (FIG. 20A and FIG. 21B). These results indicate a safe thermal block of unmyelinated C-fibers in clinical application to treat chronic pain of peripheral origin.

Experimental studies conducted in cats show that motor A-fibers can also be blocked at room temperature (15-25° C.) after a brief heating. Therefore, a heating/cooling thermal block method used to block C-fibers for pain relief, may affect motor function at the same time in some implementations. However, in many clinical applications blocking painful sensation without blocking motor function is preferred, which requires selectively block of the C-fibers without blocking the motor A-fibers. This selectivity could be achieved by the different durations for A- and C-fibers to recover from the pre-heating effect. Studies show that motor A-fibers can be blocked at room temperature for about 30 minutes after the pre-heating. However, the current study shows that the C-fibers can be blocked for more than 100 minutes. The different recovery times, indicate that after a brief heating treatment the C-fibers may be blocked at room temperatures for hours to suppress pain, while the A-fiber conduction may recover in about 30 minutes to re-gain the motor function.

Cold significantly delayed the evoked potentials (FIG. 21A) but heat did not (FIG. 22A) when producing nerve block, which indicates that the mechanisms underlying cold and heat block might be very different. Currently the mechanisms of cold or heat block are still unknown. In addition, this study also reveals that heat block of unmyelinated C-fibers can occur at 45° C. (FIG. 20A, 20B), which is very different from the heat block of myelinated A-fibers. A temperature greater than 46° C. was required for a heat block of myelinated A-fibers in the cat tibial nerve. Previous studies in cats also show that myelinated A-fibers in the pudendal nerve cannot be blocked by 46-48° C. heating for 15 minutes. The different heat sensitivity of A- and C-fiber conduction indicates that the mechanism of heat block for these two types of fibers might be different.

It is known that temperature sensitive channels, the TRPV1 and TRPV2 channels, are present in the unmyelinated C-fiber and some small myelinated Aδ-fiber, but not in the large motor A-fiber (Liu and Qin 2016). It is also known that the TRPV1 channel is activated at a temperature≥42° C. while TRPV2 channel requires a temperature≥52° C. to be activated (Pertusa et al. 2012). Therefore, in this study the pre-heating at 45° C. probably activated the TRPV1 channels in the C-fibers but not the TRPV2 channels. Activation of TRPV1 channels might have caused a series of cascading molecular reactions that can increase the cold sensitivity of the C-fiber thereby increasing the cold block temperature from 5-15° C. to 15-25° C. This hypothesis can be tested in future studies using capsaicin (an agonist for TRPV1 channel) to activate the TRPV1 channels. If this hypothesis is true, then a pre-heating at 42° C. may achieve the same effect as 45° C. However, 42° C. will be much safer than 45° C. since previous studies in rats and dogs showed that locally heating the sciatic nerve at 43-44° C. for 30-60 minutes was safe, and only produced reversible changes on the nerve (Hoogeveen et al. 1993: Vujaskovic et al. 1994).

This study reveals that unmyelinated C-fibers can be blocked by locally cooling the nerve to room temperature (15-25° C.) after a brief heating at 45° C. Although the mechanism and the minimal pre-heating temperature required for achieving a room temperature block still need to be determined, this study has provided the opportunity to develop a thermal block method that is safe to the nerve and can be applied clinically to suppress pain of peripheral origin.

Empirical Data on Thermal Modulation in Human Subjects

To demonstrate thermal nerve block in humans, wet-ice (0° C.) was used with one embodiment of a thermal modulation system described herein that circulated heated or cooled distilled water through an occipital pad at about 2-12° C. (cold) or about 42-52° C. (hot). Each system was adjustable to 20 set-temperatures between these extremes of hot and cold. In some implementations, a commercially available heating pad (Theratherm™) was used to further increase the skin-contact pad temperature when needed. Thermal nerve block in difficult-to-treat adult subject population with severe headache, migraine with or without aura, or head and/or neck pain of any cause or diagnosis who have failed many other therapies including back fusion surgeries and implantable occipital stimulators was evaluated.

In this patient population, noninvasive occipital pain block was demonstrated to be initiated in one or a few hours and the pain relief was found to persist for hours, days or weeks after a single thermal neural modulation session.

Most study participants have experienced >50% pain relief from a single thermal nerve block treatment. The preliminary data indicated that the pain reduction effect was statistically significant (p<0.01) using a two-tailed t-test with only 9 subjects. The t-score of 3.853 was greater than the critical value, and the study power was estimated to be 95.7% with p<0.05 with only 9 subjects. The complete study included 42 patients with an Average Numerical Rating Scale (NRS) pain score before treatment of 6.1±1.7 and average NRS after treatment of 2.2±2.1. This represents a 64% average reduction of pain and is highly statistically significant ($p<10^{-14}$).

In some instances, patient intake questions regarding cold and heat sensitivity, and hair density in the target anatomy, can be included as inputs to custom configure thermal modulation protocols adapted to each patient. For example, patients with higher heat/cold sensitivity can be offered thermal modulation protocols that start with more moderate temperatures for shorter durations to reduce risk of skin damage. In some instances, the thermal modulation protocol can start for all subjects with a short warm/cool cycle of moderate temperatures to further assess skin sensitivity before necessarily initiating nerve block. Such a controlled ramp of thermal energy may reduce risk of skin damage and may be automated in the thermal modulation systems described herein, according to some embodiments. Less moderate temperatures or use of a conductive gel can be offered to patients with a lot of hair in the target anatomy to be treated.

Figure 24:
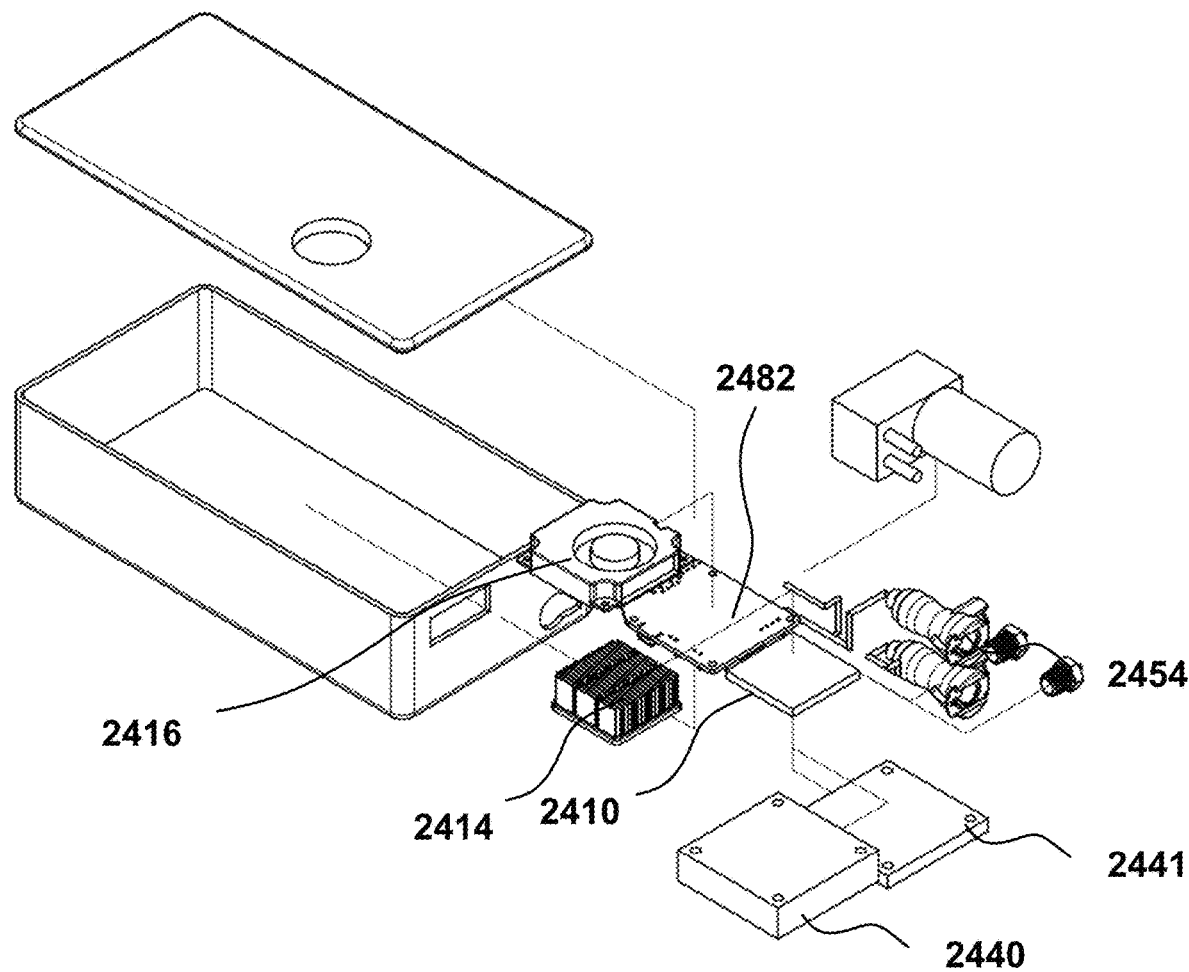
FIG. 24 is a schematic illustration of an exploded view of the components of the system controller of FIG. 23A and FIG. 23B with the PCB, pump and battery removed for visibility of other components.

FIGS. 23A-D are schematic illustrations of a controller portion 2480 of a portable thermal modulation system 2400 according to an embodiment. The system 2400 can include an applicator potion and a coupling portion (both not shown). FIG. 24 is a schematic illustration of a perspective exploded view of the components of the controller portion 2480 of the system 2400.

The controller portion 2480 includes a housing 2408 with a top portion 2460 and a bottom portion 2462. The housing 2408 covers the controller components including fluid pump 2458, battery 2484, PCB 2482, fan 2416, thermal energy source (Peltier device) 2410, heat exchanger 2440 and heat exchange cover 2441, heat sink 2414, fluid path 2450 and connects 2454. The housing 2408 can define vents 2464A,B (e.g., openings, slats, screens, etc.) provided to permit air to be pulled into the housing 2408 and to be expelled during operation. For example, ambient air can be drawn by fan 2416 and then expelled as it blows across the heat sink 2414. For example, as illustrated, air is pulled into the housing via top vents and expelled via side vents, but any compatible air path may be used.

Figure 25A:
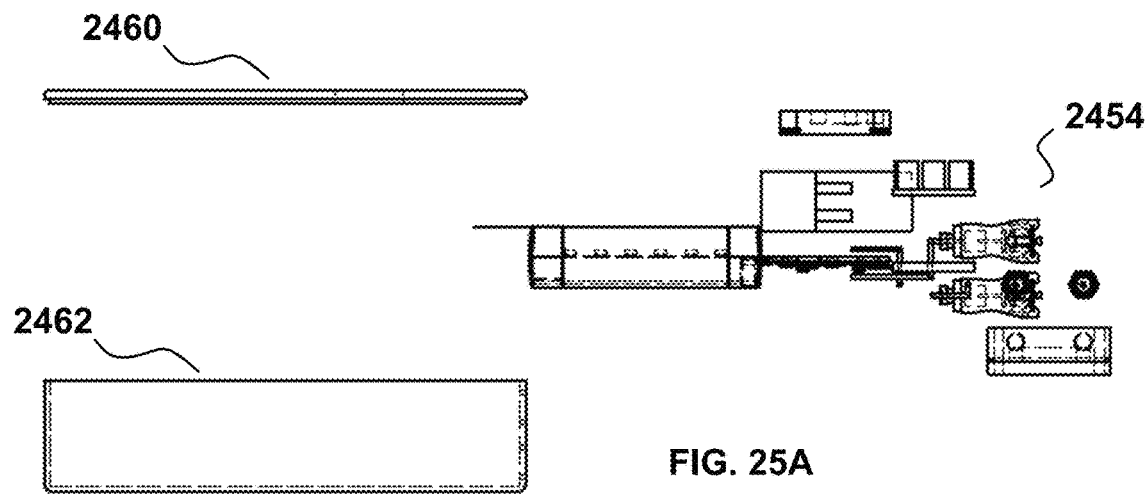
FIG. 25A-25B are schematic illustrations of a side view and a top view, respectively, of the components of the system controller of FIG. 24, according to an embodiment.
Figure 25B:
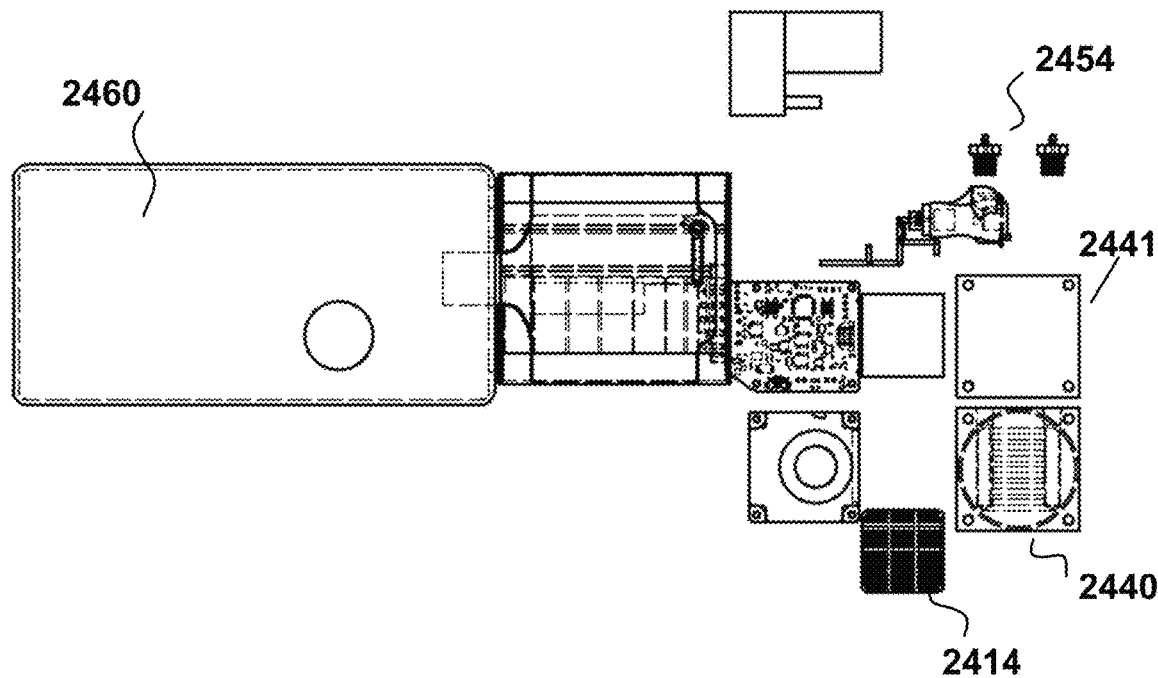
Figure 26:
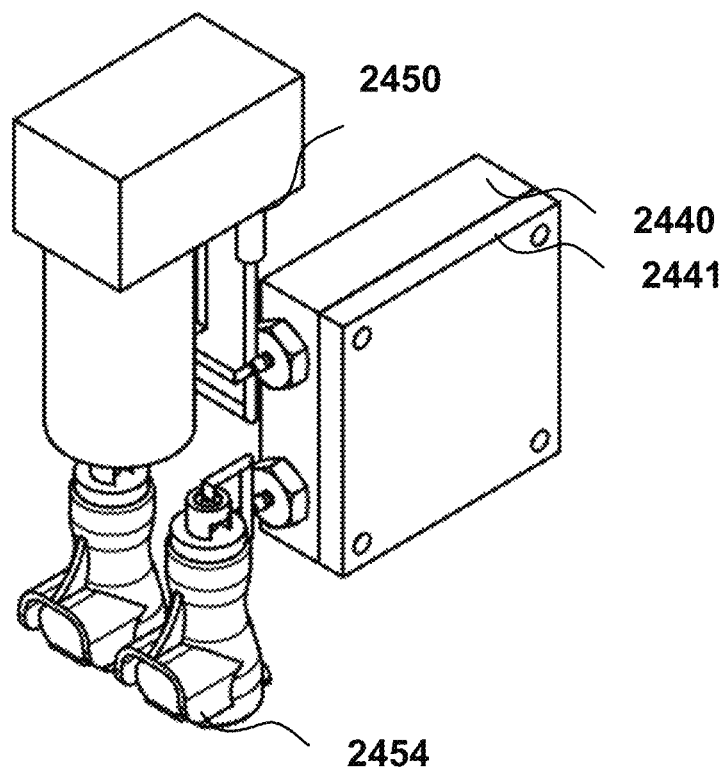
FIG. 26 is a schematic of a perspective view of some components of the system controller of FIG. 24.
Figure 27A:
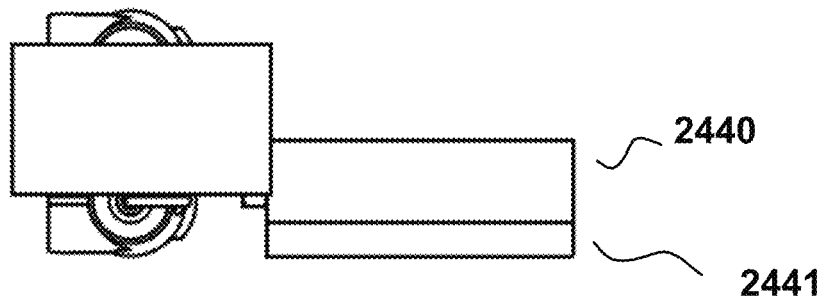
FIGS. 27A-C are schematics of side and top views of the portions of the controller shown in FIG. 26.
Figure 27B:
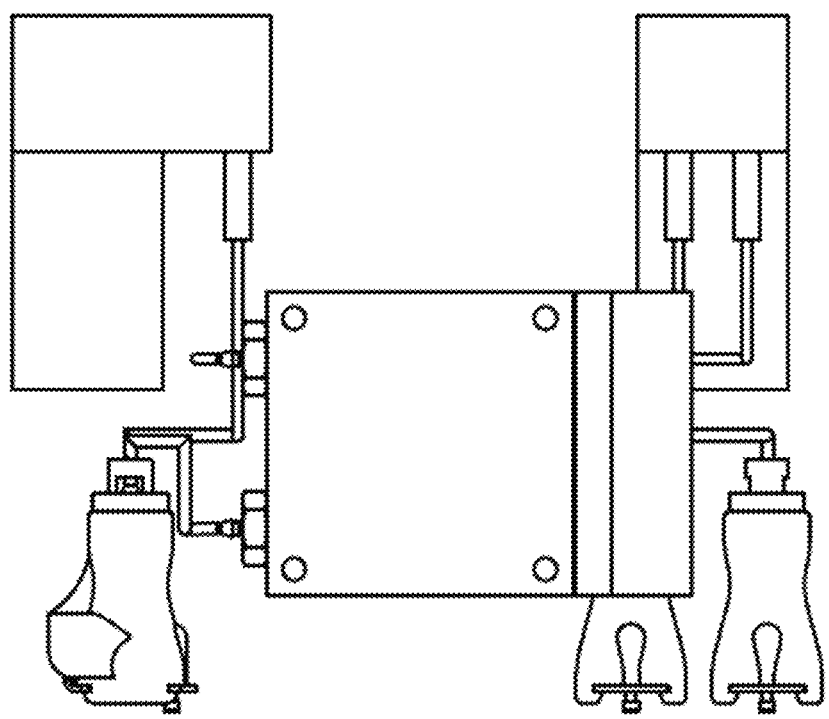
Figure 27C:
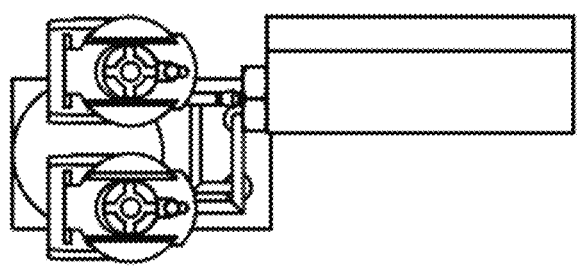

FIGS. 25A and 25B are schematics of a side and top view of an exploded arrangement of the components of the controller portion 2480 of the system 2400, with the pump 2458, PCB 2482, and the battery 2484 hidden from view for visibility of the other components. FIG. 26 is a schematic of a perspective view of the fluid handling portions of the controller 2492 including the heat exchanger 2440. FIGS. 27A-C are schematics of side and top views of the portions of the controller 2480 shown in FIG. 26.

In some embodiments, sensors (e.g., temperature sensor) may be incorporated into the PCB, and provide feedback that can be used to regulate the system performance (e.g., regulate in heating and/or cooling modes to prevent tissue-interacting devices from becoming too hot or too cold). In some embodiments, the PCB can be configured with an automatic power delay when switching from one mode to the other to protect the thermoelectric devices from degradation that otherwise may occur when switching polarities as described previously. The battery 2484 (e.g., a lithium ion battery) can power the components of the system 2400 or alternatively an external power source can be used under some circumstances.

In use, the pump 2458 can generate fluid flow from a reservoir of fluid (not shown) via fluid paths that interface with the heat exchanger 2440. The controller 2480 can set the heat source 2410) at a predetermined temperature such that the heat exchanger 2440) can treat the fluid in the portion of the fluid loop interfacing with the heat exchange 2440—for example by transferring thermal energy from the heat source 2410 to the fluid in the fluid loop. The treated fluid can be directed via the quick connects 2454 to an applicator portion (not shown). Recirculated fluid can be received from the applicator portion via the quick connects 2454 and retuned to be pumped by the pump 2458.

In some embodiments, a thermal modulation system can be configured to be used with and/or to aid in administration of surgical or medical procedures such as injections, incisions, placement of peripheral intravenous lines, feeding lines, trocars, and/or the like. For example, the thermal modulation system can be configured to be targeted at reducing the discomfort experienced by patients when receiving an injection or IV, surgical incision, trocar placement or other invasive procedures that may involve break in the skin. In some instances, the thermal modulation system may be configured to modulate the temperature over an area and/or depth adjacent or near the skin of the patient at or near the site of administration of the medical procedure. In some instances the thermal modulation system may be used to modulate temperature over an area distant from the site of administration (e.g., at a site of upstream or downstream circulation).

FIGS. 28A-28D schematically illustrate a top view, side view; orthogonal side view, and a perspective view of an applicator portion 2899 of a thermal modulation system 2800 (not shown), according to an embodiment that can be used as described above. The thermal applicator portion 2899 includes a thermal applicator 2870) that defines a portion of a fluid loop 2850 including an inlet 2807A and an outlet 2807B fluidically connected to the applicator 2870. In some embodiments, the fluid loop 2850 of the system 2800 can be configured to direct the flow of a working fluid (e.g., water), through the inlet 2807A to the applicator 2870) and via the outlet 2807B of the thermal applicator portion 2899. The temperature of the working fluid can be thermally controlled by an external device (e.g., via thermal energy source/sink). In some embodiments, the thermal applicator portion 2899 can be designed as a single use adhesive patch that can be affixed on a skin of a patient. In some embodiments, the thermal applicator portion 2899 can be designed to be a reusable patch that can be affixed to the patient's body using a suitable reversible and/or removable mechanism. In some embodiments, the applicator portion 2899 is made from a flexible polymer bag that may be manufactured out of a variety of polymers depending on desired properties including flexibility, thermal conductivity, tensile strength, etc., In some embodiments, the polymer bag may be configured to be relatively thin such that the thermal conductivity of the polymer does not need to be very high as the distance required to transfer the thermal energy is relatively small. In some implementations, other material properties may be considered including flexibility upon application, ability to be sealed with a traditional heat seal or other adhesive based sealing technology to make a watertight/fluid tight seal, biocompatibility with a user's skin, and/or ability to be adhesively joined to the skin and then removed. In some implementations, the polymer may be sealed with radiofrequency (RF) welding, ultrasonic welding or other non-adhesive based sealing technology to make a watertight/fluid-tight seal.

In some implementations, the applicator portion 2899 also referred to herein as patch, may be removed from packaging and may include a single use applicator portion 2899 or patch with adhesive on one side, and inlet 2807A and outlet tubing 2807B with quick disconnects (not shown). In some embodiments, the applicator portion 2899 may have one or more signal feedback devices (not shown) such as a temperature measurement device such as thermocouple or thermistor or any other style of sensor, sweat, heart rate, etc. The adhesive side of the applicator portion 2899 may be placed on the patient near the area of the nerve(s) to be affected. The tubing may then be connected to components of an external thermal modulation system, for example to form a complete fluid loop.

To begin use the user can turn on one or more components (e.g., a controller) of the external thermal modulation system which may initiate pumping of fluid through the fluid loop. The fluid may be pumped through interfaces with one or more thermal energy sources/sinks to be heated or cooled suitably to be circulated through the applicator portion 2899 and the thermal applicator 2870. In some implementations, the applicator portion 2899 and/or the thermal applicator 2870 may include adaptations to permit rapid switching between heating and cooling while administering thermal neural modulation to a patient. In some implementations, turning on one or more components of the external thermal modulation system may initiate a chemical reaction as a thermal energy source.

Figure 29A:
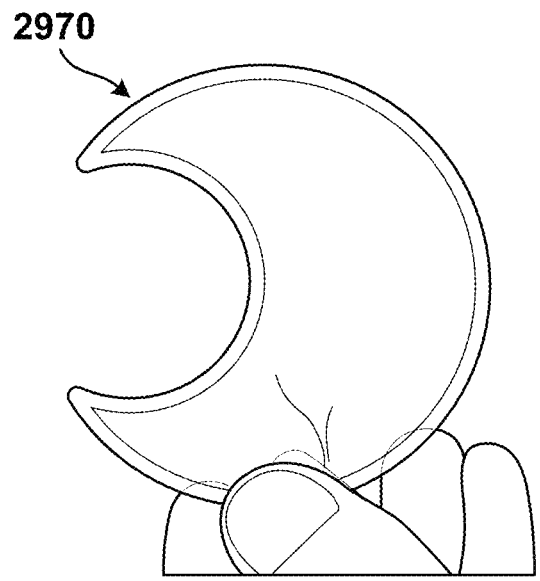
FIGS. 29A-29B are schematic representations of an applicator portion and an example method of application, respectively, of a thermal modulation system, according to an embodiment.
Figure 29B:
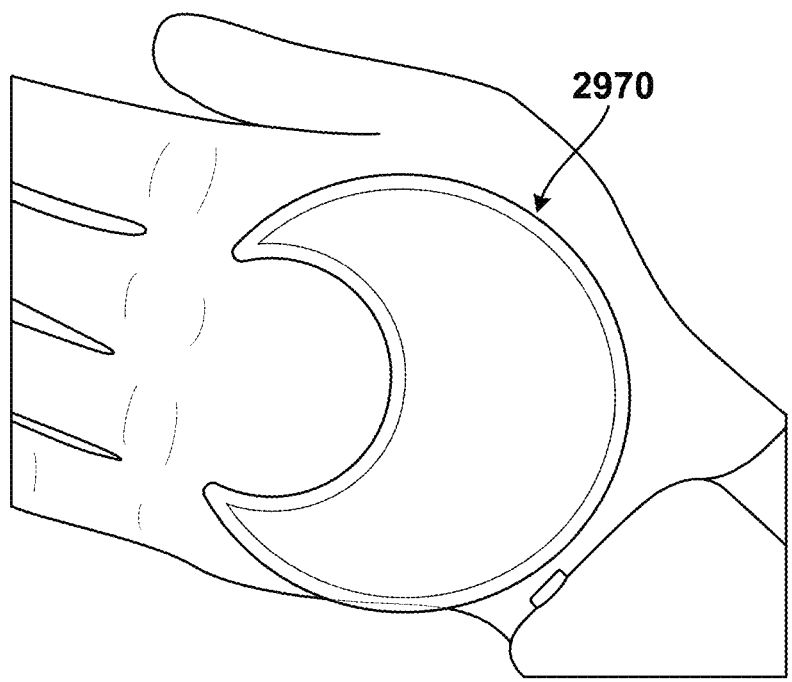

The thermal modulation system 2800 associated with the applicator portion 2899 may be reconfigured into any size/shape that is required for use anywhere on the subject's body. One example embodiment of an applicator 2970 and an example implementation is shown in FIGS. 29A and 29B, respectively. The example implementation illustrated in FIG. 29B depicts the use of the thermal applicator 2970 in preparation for placement of an IV line. The implementation shown in FIG. 29B is one of many possible configurations.

Figure 30A:
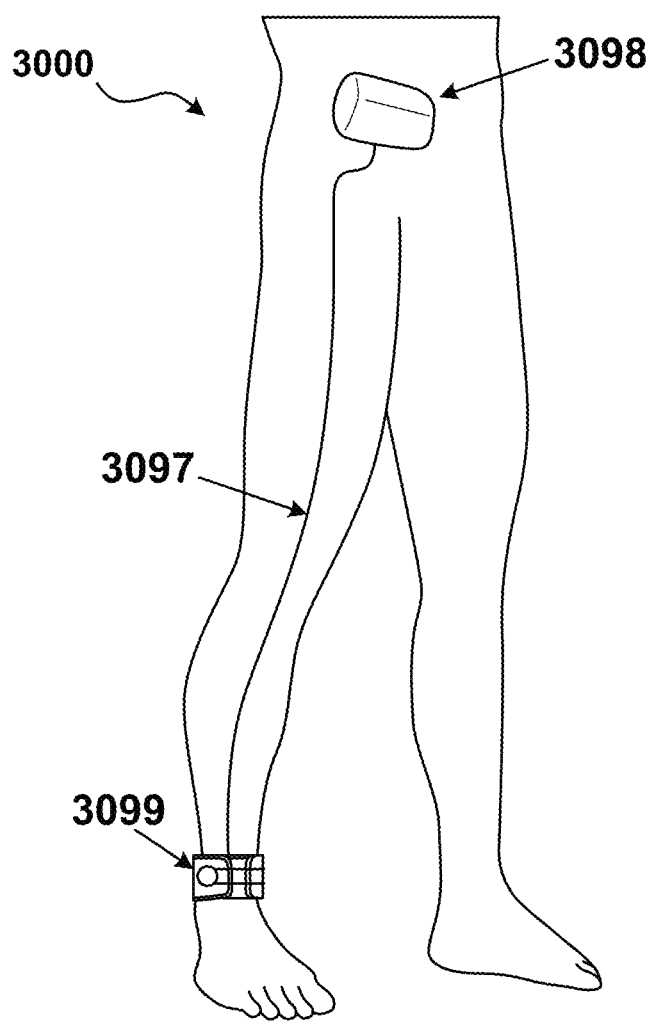
FIGS. 30A-31B are illustrations of a thermal modulation system for treatment of an ankle, foot and/or toes, according to an embodiment.

FIGS. 30A-31B illustrate a wearable thermal modulation system 3000 according to another embodiment. The thermal modulation system 3000 is an implementation of a thermal applicator for use in treating an ankle region, using a fluid loop. The system 3000 is an implementation of the systems shown in FIGS. 4-6 and may be similar in certain aspects to the system 1000 of FIGS. 10A-C. The system 3000 illustrated in FIGS. 30A-31B can be worn on the body of the patient to provide thermal modulation therapy to the ankle of the patient, according to an embodiment. The system 3000 includes the applicator portion 3099, a system controller portion 3098 that can be worn by a user (e.g., on a waist as shown in FIG. 30A) and a coupling portion 3097 coupling the applicator portion 3199 to the controller portion 3098.

The control portion 3098 includes thermal energy sink and/or source ("TESS"), a fluid loop, and a controller. The applicator portion 3099 includes a portion of the fluid loop, the thermal applicator 3070 configured to encircle the ankle and a cuff or band 3095 configured to secure the thermal applicator 3070 in operative position on the ankle. Cuff 3095 includes a clasp mechanism 3095A with an elastic cable 3095B and a post 3095C by which a user can releasably secure application portion 3099 to the ankle. Thermal applicator 3070 may contain a serpentine array of fluidic channels covering the inside of the cuff 3095, similar to, for example, the array of tubing 3807 shown in the embodiment of FIGS. 38A-38C.

Figure 31A:
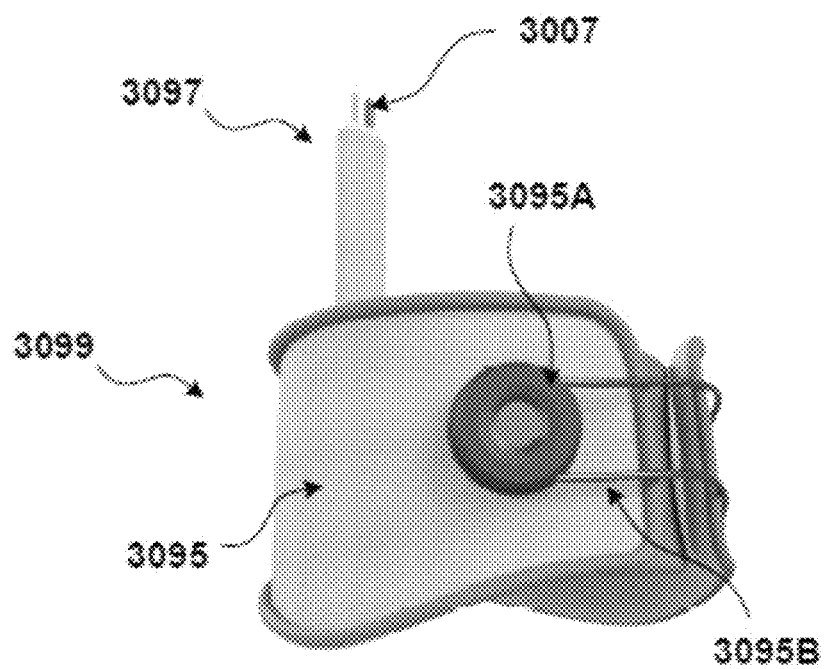

As shown in FIG. 31A, coupling portion 3097 includes tubing 3007 that forms a portion of the fluid loop 3050. The tubing 3007 can include an inlet tube and an outlet tube. The inlet can carry fluid treated to be at a desired temperature to deliver the thermal modulation to the ankle and the outlet can remove the fluid once the thermal modulation has been administered to be recirculated in the system 3000.

To begin use the user can turn on one or more components (e.g., a controller) of the external thermal modulation system which may initiate pumping of fluid through the fluid loop. The fluid may be pumped through interfaces with one or more thermal energy sources/sinks to be heated or cooled suitably to be circulated through the applicator portion 3099 and the thermal applicator 3070. In some implementations, the applicator portion 3099 and/or the thermal applicator 3070 may include adaptations to permit rapid switching between heating and cooling while administering thermal neural modulation to a patient.

Figure 31B:
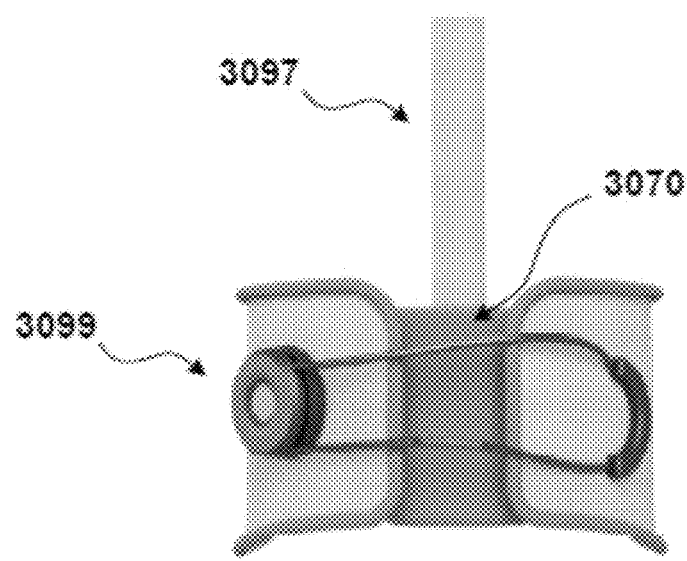

FIGS. 31A-31B show the applicator portion 3099 and the coupling portion 3097 proximate to application portion 3099. Applicator portion 3099 including the fluid tubing 1107 and the data cables 1113 used to send and receive data communications between the system controller 1198 and the applicator portion 1199 of the system 1100.

Figure 30B:
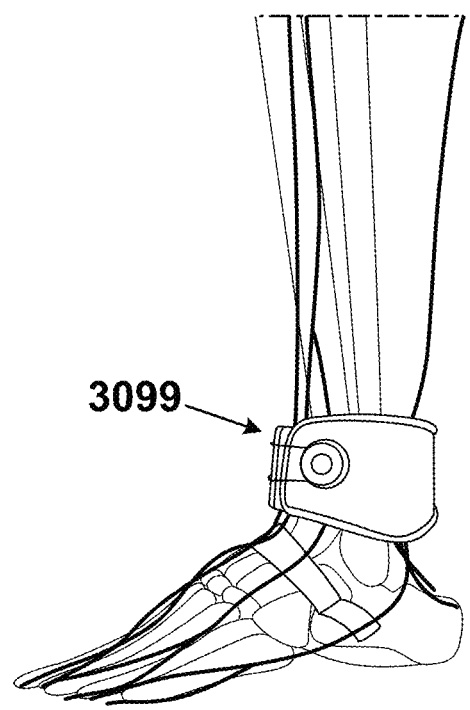

As shown in FIG. 30B, a number of nerves run past the ankle into the foot. These nerves may be blocked at the ankle, along the foot, or at any location along their path where the nerve is most shallow to the skin surface. A thermal applicator 3070 that entirely encircles the ankle can deliver and withdraw sufficient thermal energy to and from the nerves of the ankle to initiate and maintain nerve blockade. In some implementations, pain that is transmitted along sural, saphenous, superficial peroneal and deep peroneal nerves may be particularly susceptible to blockade in the ankle due to their relative superficial location relative to the skin in the ankle. Pain along these nerves can be caused by conditions including but not limited to Complex Regional Pain Syndrome (CRPS), neuromas, neuralgias, scars, post-bunionectomy surgical pain, other post-procedural pain, breaks, sprains, strains, and any other source or form or diagnosis of pain that may afflict humans or other mammals. In some implementations, nociceptive and/or neuropathic pain may be blocked.

Besides conveying pain and other sensory information, nerves of the ankle and foot are also critical for movement and motor control. Blocking motor function of the deep peroneal nerve leads to "foot drop", in which the patient is unable to lift their foot upwards. Blocking motor function of the tibial nerve reduces or prevents the ability to flex the ankle, flex the digits and invert the foot. If motor function along the superficial peroneal nerve is lost, it becomes impossible to evert the foot. By maintaining nerve temperatures≤45° C. in the ankle, pain conduction may be blocked without blocking motor function in the foot or ankle. Given relatively little hair on the foot and ankle, excellent contact may be made between the thermal applicator 3070 and the skin. Foot and ankle sensitivity to temperature varies between patients and therefore therapy parameters (e.g., heating temperatures and durations, cooling temperatures and durations) are adapted to each individual's tolerance and needs.

Figure 32A:
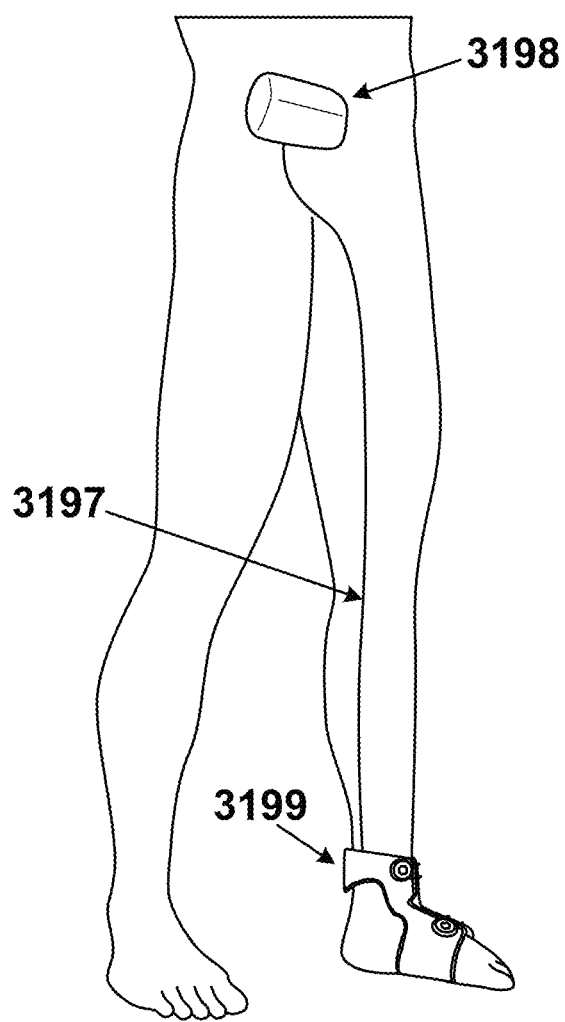
FIGS. 32A-33B are illustrations of a thermal modulation system for treatment of an ankle, foot and/or toes, according to an embodiment.
Figure 32B:
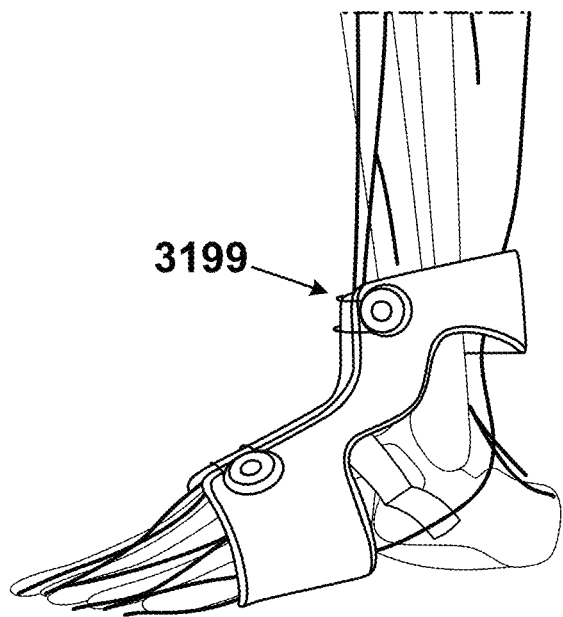
Figure 33A:
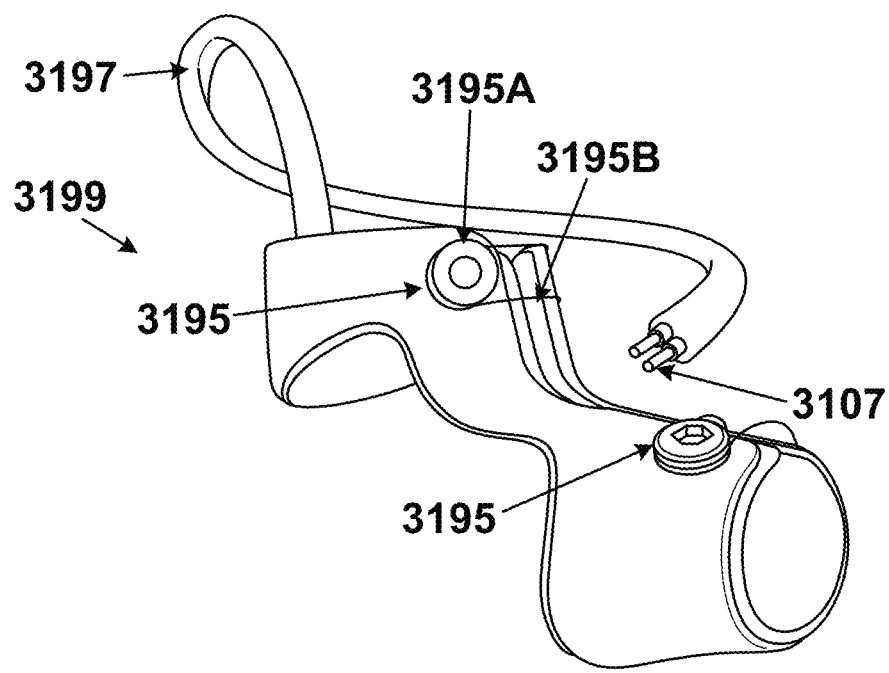
Figure 33B:
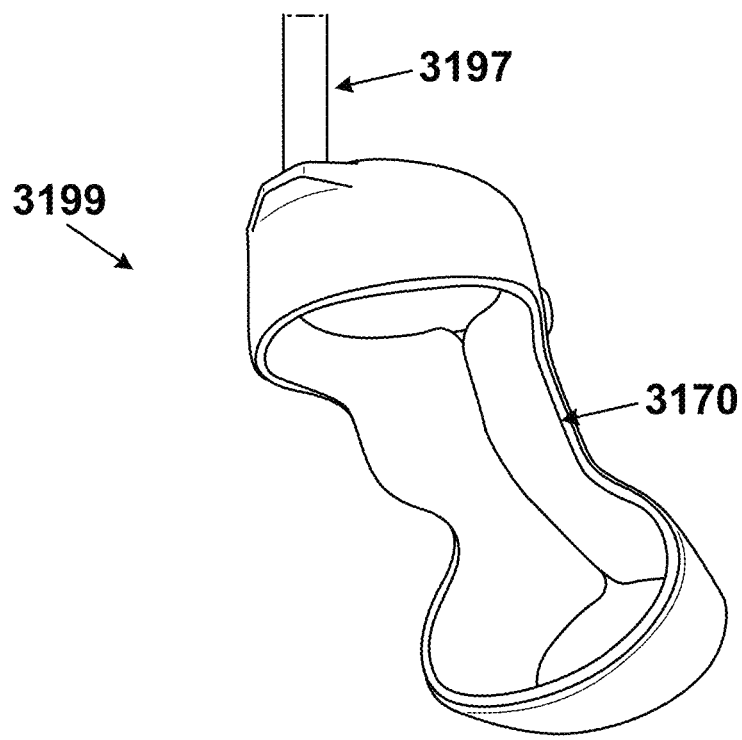

FIGS. 32A to 33B illustrate an embodiment of a foot and ankle nerve block applicator portion 3199 along with a system controller portion 3198 that can be worn by a user (e.g., on a waist as shown in FIG. 32A) and a coupling portion 3197 coupling the applicator portion 3199 to the controller portion 3198. In this embodiment, the thermal applicator 3170 wraps around the ankle and the foot, thus providing additional opportunity to block nerves that are deep to the skin at the ankle but relatively shallow to the skin at the foot such as the tibial nerve that travels into the deep inner part of the ankle before splitting into two branches, the medial plantar nerve and the lateral plantar nerve, which may be more easily thermally modulated in the foot versus in the ankle.

The control portion 3198 (not shown) includes thermal energy sink and/or source ("TESS"), a fluid loop, and a controller. The applicator portion 3199 includes a portion of the fluid loop, the thermal applicator 3170 configured to encircle the ankle and part of the foot adapter 3195 configured to secure the thermal applicator 3070 in operative position on the ankle. Adapter 3195 includes a clasp mechanism 3195A with an elastic cable 3195B and a post 3195C by which a user can releasably secure application portion 3199 to the ankle. Thermal applicator 3170 may contain a serpentine array of fluidic channels covering the inside of the adapter 3195.

Figure 34A:
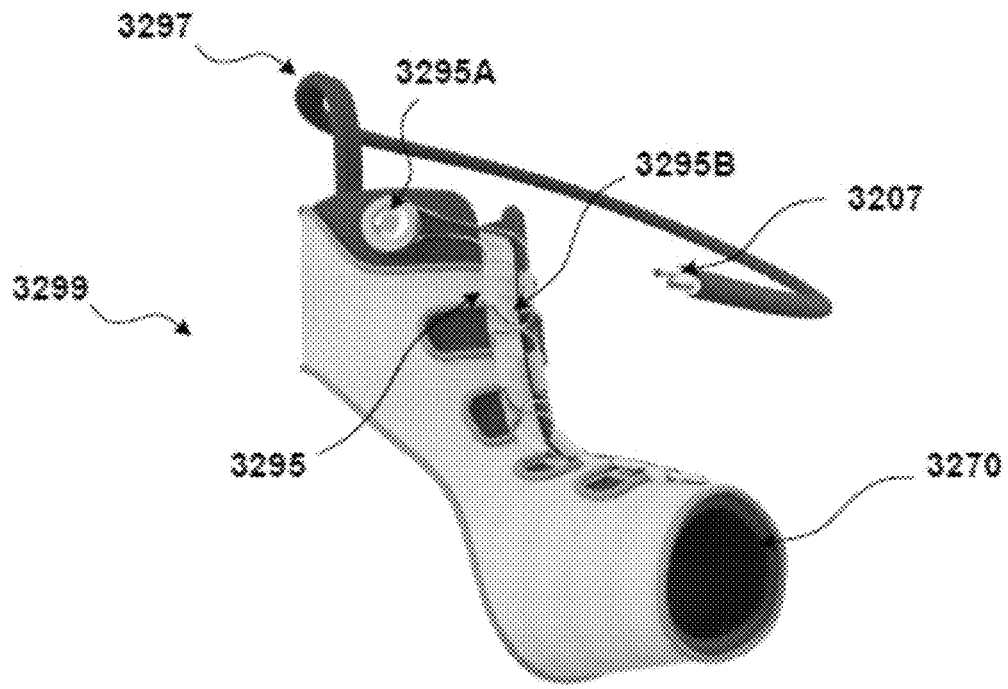
FIGS. 34A-34B are illustrations of the applicator portion of a thermal modulation system for treatment of an ankle, foot and/or toes, according to an embodiment.
Figure 34B:
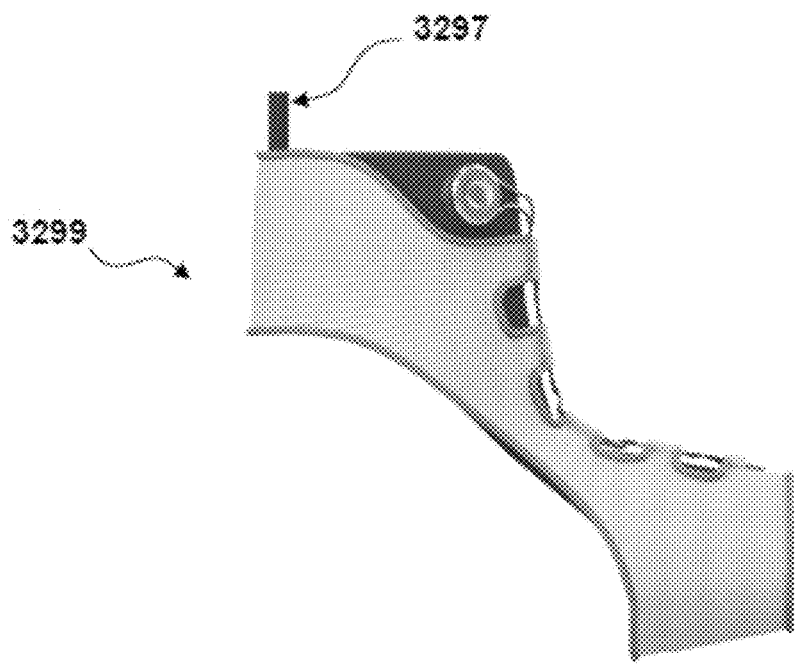
Figure 35:
FIG. 35 is an illustration of the application portion of FIGS. 34A and 34B shown partially disposed in a shoe, according to an embodiment.

FIGS. 34A-35 illustrate another embodiment of a foot and ankle nerve block applicator portion 3299 along with a system controller portion 3298 (not shown) and a coupling portion 3297 coupling the applicator portion 3199 to the controller portion 3198. This applicator portion 3299 is made of a less rigid material than applicator portion 3199, and therefore the clasp mechanism 3295A is supplemented with lacing 3295B to ensure secure fit and close contact between thermal applicator 3270 and the patient's skin. FIG. 35 shows one implementation in which applicator portion 3299 of FIGS. 34A-34B is shown partially disposed in a shoe. Such an implementation may allow the patient to continue their desired activities including standing, walking and running or other sports or pursuits while concurrently receiving nerve block therapy.

Figure 36A:
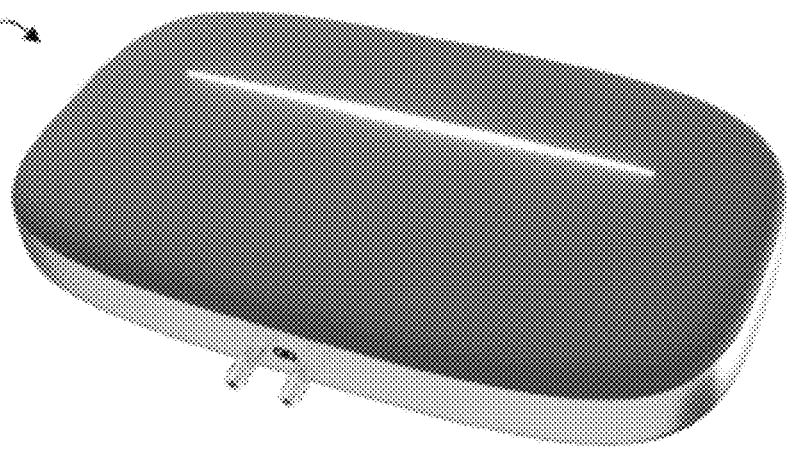
FIGS. 36A-36B are illustrations of a controller portion of a thermal modulation system, according to an embodiment.
Figure 36B:
Figure 37:
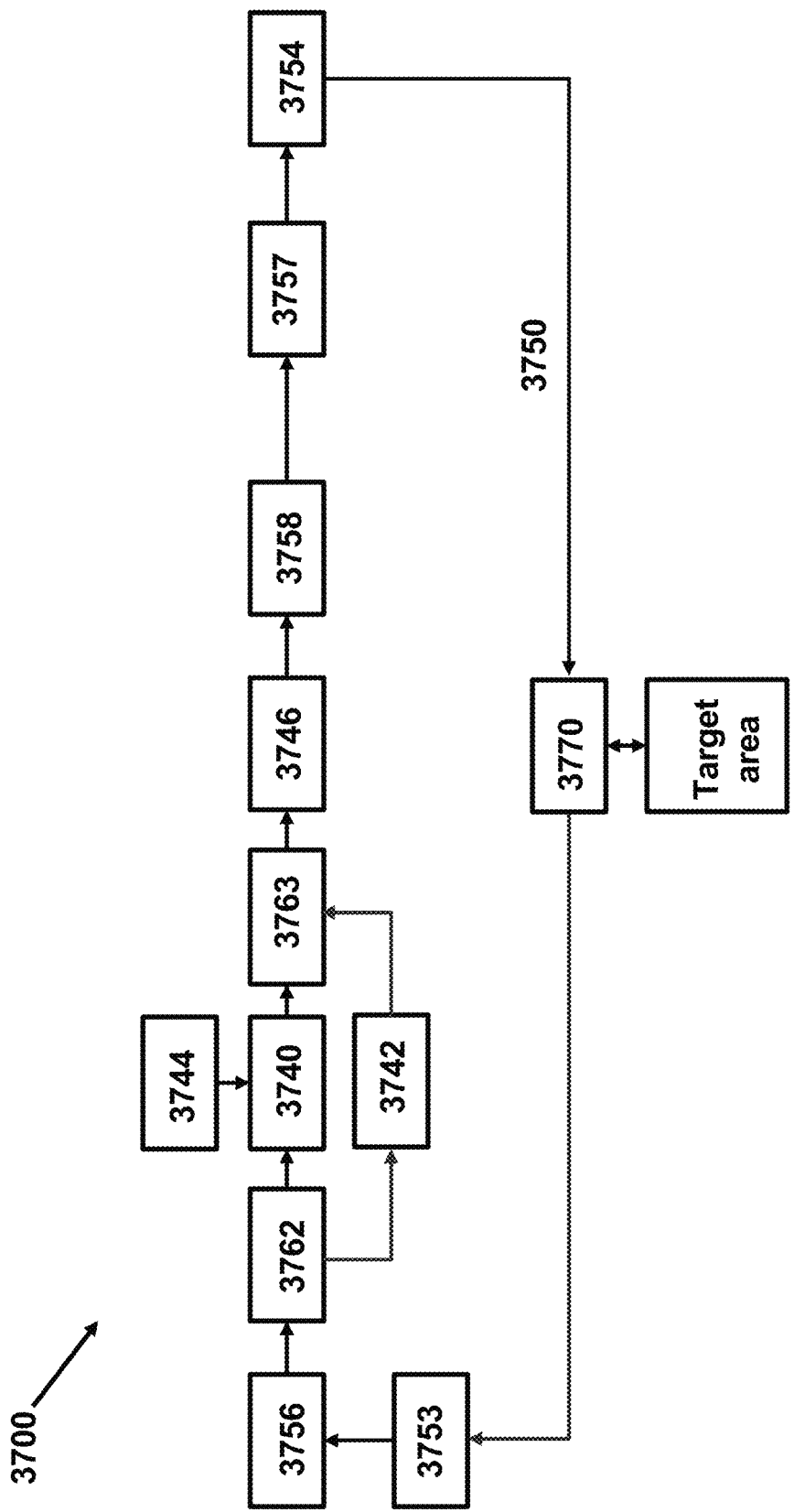
FIG. 37 is a schematic representation of a thermal modulation system and its operation according to an embodiment.

FIGS. 36A-36B show a controller portion 3398 of a thermal modulation system, such as controller portions 3098 and 3198 of thermal modulation systems 3000 and 3100, respectively. The control portion 3398 includes thermal energy sink and/or source ("TESS"), a fluid loop, and a controller. The control portion 3398 can be worn by a user and attached to a coupling portion (not shown) coupling the applicator portion (not shown) to the controller portion 3398. In some implementations, TESS can include a thermoelectric cooler (TEC) as thermal energy sink and/or source. In some implementations, TESS can include a TEC as sink and/or source, and also an ice/water reservoir as sink. In some implementations, TESS can include a resistive heater (e.g. resistive heating wire) as source and ice/water reservoir as sink. In some implementations, as shown in FIG. 36B, a fastener can be used to secure the control portion 3398 to the user, for example to their belt using a clasp as shown FIG. 37 is a schematic representation of a thermal modulation system 3700 and its operation, based on system 100 in FIG. 1, in which the included TESS is implemented by a heating resistor 3744 as a thermal energy source and an ice bath 3742 as thermal energy sink. System 3700 reflects an approach to implementing a wearable thermal modulation system mediating transfer of thermal energy via a fluid loop. Thus, system 3700 includes thermal energy sink and thermal energy source (TESS) 3710, heat exchanger 3740, a fluid loop 3750, a thermal applicator 3770, quick disconnects 3756, pump 3758, insulated tubing 3753, fill reservoir 3746, diverter valves 3762 that may be solenoid valves, heating resistor 3744, and ice bath (ice/water reservoir) 3742. and a controller (not shown). The system 3700 also includes heat sink 914 thermally coupled to TC 912. The system 3700 includes diverter valves 3762 that may be a solenoid valve in some implementations to direct the flow of water to either the thermal energy source heat exchanger 3740 that is in thermal contact with heating resistor 744 or to the ice bath 3742 as thermal energy sink before being directed into fill reservoir 3746. Fluid loop 3750 includes first insulated tubing 3753 coupled to quick disconnect 3756 to quick disconnect 3756 and diverter valve 3762 to heat exchanger 3740 or ice bath 3742 to diverter valve 3763 and fill reservoir 3746. Fluid loop 3750 also includes pump 3758 to circulate fluid (e.g. water) through fluid loop 3750 to a second quick disconnect 3757 and second insulated tubing 3754. Thermal applicator 3770 can be implemented as any of the thermal applicators disclosed in the previous embodiments. A heat exchanger and a temperature sensor (not show in FIG. 37) are associated with thermal applicator 3770. Controller 3780 (not shown) includes a control PCB (not shown) that can be powered by any of the sources of power disclosed above, including battery and optional alternating current input.

Figure 38A:
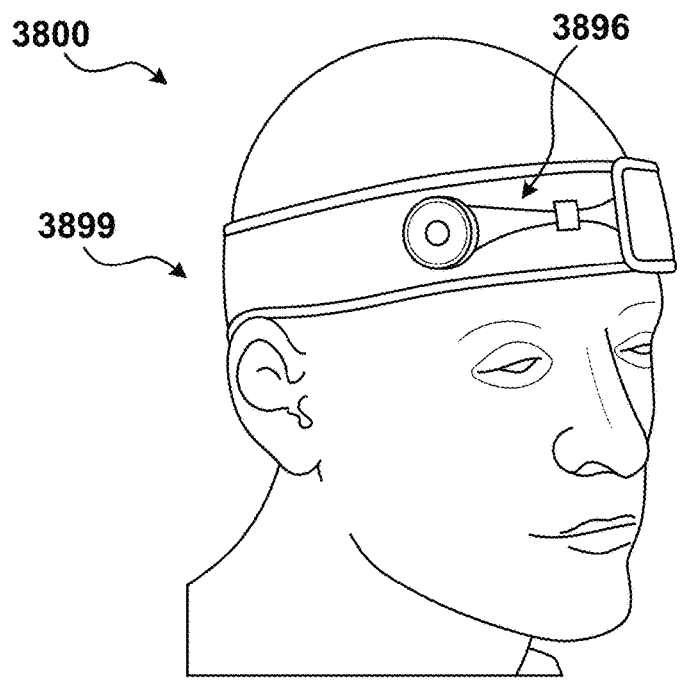
FIGS. 38A-38C are illustrations of the applicator portion of a thermal modulation system for treatment of a head, according to an embodiment
Figure 38B:
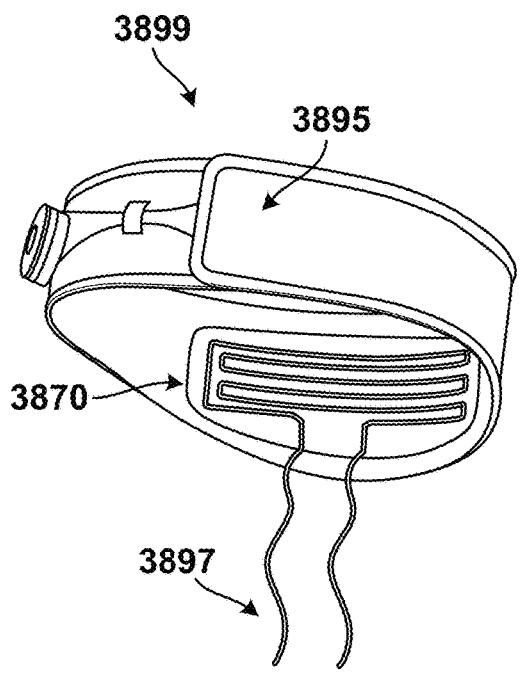
Figure 38C:
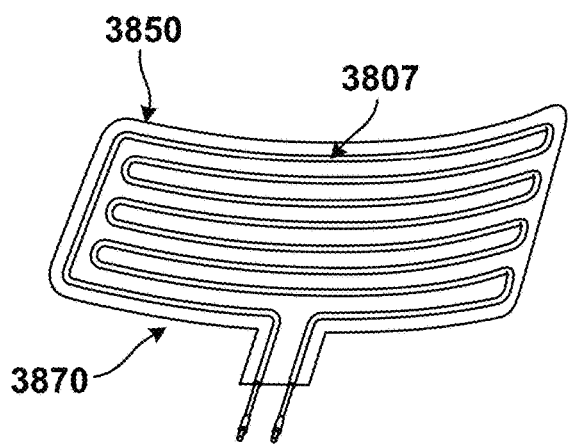

FIGS. 38A-38C illustrate a wearable thermal modulation system 3800 according to another embodiment. The thermal modulation system 3800 is an implementation of a thermal applicator for use in treating a head region, using a fluid loop. The system 3800 is an implementation of the systems shown in FIGS. 10A-12C and 12A-12C and may be similar in certain aspects to the system 3000 of FIGS. 30A-31B (though for the user's head rather than ankle). The system 3800 illustrated in FIGS. 38A-38C can be worn an occipital region or back portion of the head/neck of a patient, to provide thermal modulation therapy, according to an embodiment. The system 3800 includes the applicator portion 3899, a system controller portion (not shown) that can be worn by a user, and a coupling portion 3897 coupling the applicator portion 3899 to the controller portion.

FIG. 38A shows the fastening of the applicator portion 3899 in use and FIG. 38B shows a view of the applicator portion 3899 including the thermal applicator 3870. FIG. 38C shows the thermal applicator 3870 in more detail, showing fluid tubing 3807 that forms portions of the fluid loop 3850 is arranged in serpentine shape and used to circulate temperature modulated fluid to administer thermal modulation therapy to the occipital region of the patient for example targeting the occipital nerve. The tubing 3807 can include an inlet tube and an outlet tube. The inlet can carry fluid treated to be at a desired temperature to deliver the thermal modulation to the patient and the outlet can remove the fluid once the thermal modulation has been administered to be recirculated in the system 3800. In some embodiments, the inlet and the outlet can be on the same side as shown. In some embodiments, the inlet can be on one side and the outlet can be on another side of the applicator portion 3899.

The applicator portion 3899 includes a cuff or band 3895 configured to secure the thermal applicator 3870 in operative position on the head. Cuff 3895 includes a clasp mechanism 3896 with an elastic cable and a post by which a user can releasably secure application portion 3899 to the head, similar to the cuff 3195 in the embodiment of FIGS. 30A-31B. The clasp mechanism 3896 may also be implemented similar to the lacing mechanism shown in the embodiment of FIGS. 34A-34C, and thus may be adjusted, e.g. tightened, by the user to allow a uniform snug fit across the target region, and secure good contact between thermal applicator 3870 and the user's body.

To begin use the user can turn on one or more components (e.g., a controller) of the external thermal modulation system which may initiate pumping of fluid through the fluid loop. The fluid may be pumped through interfaces with one or more thermal energy sources/sinks to be heated or cooled suitably to be circulated through the applicator portion 3899 and the thermal applicator 3870. In some implementations, the applicator portion 3899 and/or the thermal applicator 3870 may include adaptations to permit rapid switching between heating and cooling while administering thermal neural modulation to a patient.

FIGS. 39A-39D illustrate a wearable thermal modulation system 3900 according to another embodiment. The thermal modulation system 3900 is an implementation of a thermal applicator for use in treating a head and/or neck region, using a fluid loop. The system 3900 is similar to system 3800 shown in FIGS. 38A-38C, but also includes an optional full-head coverage adapter that is temporarily or permanently attached or fixed to a decorative head covering 3971 that may be removably attached to the thermal applicator 3970 to provide wardrobe flexibility and minimize the appearance that the user is wearing a medical device. The system 3900 illustrated in FIGS. 39A-39D can be worn an occipital region or back portion of the head/neck of a patient, to provide thermal modulation therapy, according to an embodiment. The system 3900 includes the applicator portion 3999, a system controller portion (not shown) that can be worn by a user, and a coupling portion 3997 coupling the applicator portion 3999 to the controller portion.

FIGS. 38A and 38B show the fastening of the applicator portion 3999 in use and FIGS. 39C and 39D show views of the applicator portion 3999 including the thermal applicator 3970. FIG. 39D shows the thermal applicator 3970 in more detail, showing fluid tubing 3907 that forms portions of the fluid loop 3950 is arranged in serpentine shape and used to circulate temperature modulated fluid to administer thermal modulation (nerve block) therapy for example to the occipital region of the patient targeting block of the occipital nerves. The tubing 3907 can include an inlet tube and an outlet tube. The inlet can carry fluid treated to be at a desired temperature to deliver the thermal modulation to the patient and the outlet can remove the fluid once the thermal modulation has been administered to be recirculated in the system 3900. In some embodiments, the inlet and the outlet can be on the same side as shown. In some embodiments, the inlet can be on one side and the outlet can be on another side of the applicator portion 3999.

The applicator portion 3999 includes a cuff or band 3995 configured to secure the thermal applicator 3970 in operative position on the head. Cuff 3995 may be implemented similar to cuff 3895 described above, with a similar clasp or tension mechanism, or may use other tensioning mechanisms.

Head covering 3971 may be made of breathable, mesh materials or made of cotton, wool, or other warm, thermally insulating materials. It may be releasably attached to cuff or band 3995 by any suitable mechanism, such as cooperating hook and loop fastener portions disposed on head covering 3971 and cuff or band 3995.

To begin use the user can turn on one or more components (e.g., a controller) of the external thermal modulation system which may initiate pumping of fluid through the fluid loop. The fluid may be pumped through interfaces with one or more thermal energy sources/sinks to be heated or cooled suitably to be circulated through the applicator portion 3999 and the thermal applicator 3970. In some implementations, the applicator portion 3999 and/or the thermal applicator 3970 may include adaptations to permit rapid switching between heating and cooling while administering thermal neural modulation to a patient.

Detailed embodiments of the present disclosure have been disclosed herein or purposes of describing and illustrating claimed structures and methods that can be embodied in various forms, and are not intended to be exhaustive in any way, or limited to the disclosed embodiments. Many modifications and variations will be apparent without departing from the scope of the disclosed embodiments. The terminology used herein was chosen to best explain the principles of the one or more embodiments, practical applications, or technical improvements over current technologies, or to enable understanding of the embodiments disclosed herein. As described, details of well-known features and techniques can be omitted to avoid unnecessarily obscuring the embodiments of the present disclosure.

References in the specification to "one embodiment," "an embodiment," "an example embodiment," or the like, indicate that the embodiment described can include one or more particular features, structures, or characteristics, but it shall be understood that such particular features, structures, or characteristics may or may not be common to each and every disclosed embodiment disclosed herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

Parameters, dimensions, materials, and configurations described herein are meant to be examples and that the actual parameters, dimensions, materials, and/or configurations will depend upon the specific application or applications for which the inventive teachings is/are used. It is, therefore, to be understood that the foregoing embodiments are presented by way of example only and that, within the scope of the appended claims and equivalents thereto; and that embodiments can be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

As you herein, the phrase "and/or" should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" phrase, whether related or unrelated to those elements specifically identified. Thus, as a non-limiting example, a reference to "A and/or B", when used in conjunction with open-ended language such as "comprising" or "including" can refer, in one embodiment, to A only (optionally including elements other than B): in another embodiment, to B only (optionally including elements other than A); in yet another embodiment, to both A and B (optionally including other elements); etc.

As used herein, the term, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "about" and/or "approximately" when used in conjunction with values and/or ranges generally refer to those values and/or ranges near to a recited value and/or range. In some instances, the terms "about" and "approximately" may mean within ±10% of the recited value. For example, in some instances, "approximately a diameter of an instrument" may mean within ±10% of the diameter of the instrument. The terms "about" and "approximately" may be used interchangeably. Similarly, the term "substantially" when used in conjunction with physical and/or geometric feature(s), structure(s), characteristic(s), relationship(s), etc. is intended to convey that the feature(s), structure(s), characteristic(s), relationship(s), etc. so defined is/are nominally the feature(s), structure(s), characteristic(s), relationship(s), etc. As one example, a first quantity that is described as being "substantially equal" to a second quantity is intended to convey that, although equality may be desirable, some variance can occur. Such variance can result from manufacturing tolerances, limitations, approximations, and/or other practical considerations. Thus, the term "substantially."

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments described herein.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

The invention claimed is:

1. A method comprising:
delivering thermal energy to a treatment portion of a target nerve in a body of a subject mammal via a thermal applicator disposed in operative relationship with the treatment portion to increase a temperature of the treatment portion to a first temperature above a physiologic temperature of the target nerve, the target nerve being a C-fiber nerve and/or an A-δ fiber nerve, carrying pain signals;
continuing to deliver thermal energy to the treatment portion via the thermal applicator to maintain the temperature of the treatment portion at the first temperature for a first duration sufficient to pre-condition the target nerve;
ceasing delivery of thermal energy to the treatment portion;
the continuing to deliver thermal energy and the ceasing delivery of thermal energy being such that after the ceasing delivery a withdrawal of thermal energy to a second temperature can achieve a blockade of the target nerve, the second temperature being below the physiologic temperature of the target nerve by a first degree, the second temperature being higher than a third temperature that is below the physiologic temperature of the target nerve by a second degree greater than the first degree and required to be achieved, via withdrawal of thermal energy, for a blockade of the target nerve in an absence of the pre-condition,
the first temperature being sufficient to pre-condition the target nerve or initiate a reversible, partial blockade of the target nerve, and insufficient to pre-condition or initiate a reversible, partial blockade of an A-β fiber, that is myelinated and carrying motor signals and having a portion in proximity to the treatment portion of the target nerve;
withdrawing thermal energy from the treatment portion via the thermal applicator to decrease a temperature of the treatment portion to the second temperature below the physiologic temperature of the target nerve; and
continuing to withdraw thermal energy from the treatment portion via the thermal applicator to maintain the temperature of the treatment portion at the second temperature for a second duration sufficient to achieve a reversible blockade of the target nerve, before the target nerve has recovered from the pre-condition or reversible partial blockade, without inducing a blockade of the A-β fiber that is myelinated and carrying motor signals and having the portion in proximity to the treatment portion of the target nerve.

2. The method of claim 1, wherein the first temperature is between about 42° C. and about 45° C.

3. The method of claim 2, wherein the first duration is between about 5 minutes and about 180 minutes.

4. The method of claim 2, wherein the first duration is between about 5 minutes and about 60 minutes.

5. The method of claim 1, wherein the second temperature is between about 15° C. and about 30° C.

6. The method of claim 5, wherein the second duration is between about 5 minutes and about 60 minutes.

7. An apparatus comprising:
a thermal energy source;
a thermal energy sink;
a thermal energy conduit coupled to the thermal energy source and to the thermal energy sink;
a thermal applicator coupled to the thermal energy conduit and configured:
to be applied topically to a skin overlying a treatment portion of a target nerve in a treatment location on a body of a subject mammal, the target nerve being a C-fiber nerve and/or an A-δ fiber nerve, carrying pain and/or other undesired sensory signals, to receive thermal energy from the thermal energy source via the thermal energy conduit and to deliver the thermal energy to the treatment portion of the target nerve, and to receive thermal energy from the treatment portion of the target nerve and convey it to the thermal energy sink via the thermal energy conduit; and a controller operatively coupled to the energy source and the thermal energy sink, and configured:

to cause the energy source to provide energy to the thermal applicator via the energy conduit at a temperature and thermal energy delivery rate sufficient to raise the temperature of the treatment portion of the target nerve to a first temperature above a physiologic temperature and to maintain the first temperature for a first duration sufficient to pre-condition the target nerve, to cease delivery of thermal energy, and then to cause the thermal energy sink to cause thermal energy to be removed from the thermal applicator at a rate sufficient to lower the temperature of the treatment portion of the target nerve to a second temperature, below the physiologic temperature, sufficient to achieve a reversible blockade of the target nerve, the second temperature being below the physiologic temperature by a first degree, the second temperature being higher than a third temperature that is below the physiologic temperature of the target nerve by a second degree greater than the first degree and required to be achieved, via withdrawal of thermal energy, for a blockade of the target nerve in an absence of the pre-condition.

8. The apparatus of claim 7, wherein the thermal energy conduit includes a fluid conduit that is configured to have fluid circulated therethrough to convey thermal energy between the thermal applicator and the thermal energy source and the thermal energy sink.

9. The apparatus of claim 7, wherein the controller is configured to cause the energy source and the thermal energy sink to operate in accordance with the method of claim 1.

10. The apparatus of claim 7, wherein the thermal energy source is a thermoelectric heater.

11. The apparatus of claim 7, wherein the thermal energy sink is a thermoelectric cooler.

12. The method of claim 1, wherein the thermal applicator is applied topically to a skin overlying the treatment portion of the target nerve in the body of the subject mammal.

13. The method of claim 1, wherein at least one of the delivering thermal energy to the treatment portion of the target nerve or the withdrawing thermal energy from the treatment portion of the target nerve is performed using a thermoelectric heater or a thermoelectric cooler, respectively.

* * * * *